(12) United States Patent
Coupland et al.

(10) Patent No.: US 6,887,708 B1
(45) Date of Patent: May 3, 2005

(54) PLANT CONTROL GENES

(75) Inventors: George M. Coupland, Norfolk (GB); Joanna J. Putterill, Auckland (NZ); Sarah G. Fowler, Ann Arbor, MI (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/646,533

(22) PCT Filed: Mar. 19, 1999

(86) PCT No.: PCT/NZ99/00033

§ 371 (c)(1), (2), (4) Date: Oct. 10, 2000

(87) PCT Pub. No.: WO99/49064

PCT Pub. Date: Sep. 30, 1999

(30) Foreign Application Priority Data

Mar. 20, 1998 (NZ) ............................................... 330020

(51) Int. Cl.[7] .......................... C12N 15/82; C12N 5/10; C12N 15/29; A01H 5/00; A01H 5/10
(52) U.S. Cl. .................... 435/468; 435/320.1; 435/419; 536/23.6; 800/290
(58) Field of Search .............................. 435/69.1, 320.1, 435/410, 419, 468; 536/23.6; 800/278, 290, 285, 286, 284, 298

(56) References Cited

FOREIGN PATENT DOCUMENTS

| WO | 91/19806 A | 12/1991 | ........... C12N/15/82 |
|---|---|---|---|
| WO | 96/14414 A | 5/1996 | ........... C12N/15/29 |
| WO | 96/38560 A | 12/1996 | ........... C12N/15/29 |

OTHER PUBLICATIONS

Hayama et al., Nature, 2003, vol. 422, pp. 719–722.*
Fowler et al., EMBO J., 1999, vol. 18, pp. 4679–4688.*
Terryn N. et al.: "Sequence Analysis of a 24–kb Contiguous Genomic Region at the *Arabidopsis thaliana* PFL Locus on Chromosome 1" FEBS LETTERS, vol. 416, 1997, pp. 156–160.
Richardson K et al.: "T–DNA Lagging of a Flowering–Time Gene and Improved Gene Transfer by in Planta Transformation of Arabidopsis" Australian Journal of Plant Physiology, Mar. 1998, vol. 25, No. 1, pp. 125–130.
Eimert K et al: "Monogenic Recessive Mutations Causing Both Late Floral Initiation and Excess Starch Accumulation in *Arabidopsis*" Plant Cell, Oct. 1995, vol. 7, No. 10, pp. 1703–1712. Acad Sinica, Inst Molec Biol, Taipei, Taiwan (Reprint); Acad Sinica, Inst Molec Biol, Taipei, Taiwan; Natl Taiwan Univ, Dept Bot, Taipei 10764, Taiwan.
Araki, T. et al.: "Analysis of the Role of the Late–Flowering Locus, GI, in the Flowering of *Arabidopsis thaliana*" Plant Journal, 1993 vol. 3, No. 2, pp. 231–239. Molecular Genetics Research Laboratory, University of Tokyo, Tokyo, Japan.
Sasaki T.: "Ricer EST AC C72988" EMBL Database, Sep. 1997 Heidelberg.

* cited by examiner

*Primary Examiner*—Ashwin Mehta
(74) *Attorney, Agent, or Firm*—Nixon & Vanderhye P.C.

(57) ABSTRACT

The invention provides nucleic acid isolates comprising nucleotide sequences encoding polypeptides having Gl function, or which are complementary to such sequences. Constructs containing such nucleic acids are useful in transforming plants to control flowering and/or starch accumulation in the transformed plant.

10 Claims, 26 Drawing Sheets

```
  377 TTAAAGTAGATTTTAAAATTAGNTCATGGTTAAAAATAGACAGAATTTTG
      || |||||||||||||| ||||:||||||||||||||||||||||||||
14482 TTTAAGTAGATTTTAAACTTAGCTCATGGTTAAAAATAGACAGAATTTTG

327 GAGTAAATNTGAGTTTAACAAAATTTATTTATTAGGGATTAAAATTAATT
      ||||||||:||||||| ·|||||||||||||||| |||||||||||||||
14532 GAGTAAATCTGAGTTT.ACAAAATTTATTTATTA.GGATTAAAATTAATT

277 AACTTAAATTGGCAAACATTTTTTNTTGGTGATTGTAACATACAATATAN
      |||||||||||||||| |||||:||||||||||||||||||||||||||:
14580 .ACTTAAATTGGCAAACA.TTTTTCTTGGTGATTGTAACATACAATATAC

227 GAATTTGAATTCGGAATTGTGATTCCAAAACAACACTAACATAAANTACC
      |||||||||||| | ||||||||||||||||||||||||||||||:||||
14628 GAATTTGAATTC.GCATTGTGATTCCAAAACAACACTAACATAAACTACC

177 AGTAAACTTTTTTAAAATAAAATTTGTATATATATGCTTAAAAAATGTA
      |||||| |||||||||||||||||| ||||||||||||||||||||||||
14677 AGTAAATTTTTTAAAATAAAATTTCATATATATATGCTTAAAAAATGTA

127 ACAAAAATATGGTAAATTTTTAACCATGGTATGGGTGGAGATGTATGTG
      ||||||||||||||||||||||||||||||||||||||||||||||||||
14727 ACAAAAATATGGTAAATTTTTAACCATGGTATGGGTGGAGATGTATGTG

77 GGATGATGATGGTTATATGGTAATGGCGCATAAAGGTGGTGGCAAAGGCA
      ||||||||||||||||||||||||||||||||||||||||||||||||||
14777 GGATGATGATGGTTATATGGTAATGGCGCATAAAGGTGGTGGCAAAGGCA

27 AGGAAATATCGATGACACGTAAGCAGA   > Beginning of T-DNA sequence
      |||||||||||||||||||||||||||
14827 AGGAAATATCGATGACACGTAAGCAGA 14853
```

FIGURE 1 cDNA1 5' end sequence

GGACCTGTGGCAGCATTTGATTCATACGTTCTTGCTGCTGTTTGTGCTCTTGCCTGTGAG
GTTCAGCTGTATCCTATGATCTCTGGTGGGGGGAACTTTTCCAATTCTGCCGTGGCTGGAACTATTACAAAGCCT
GTAAAGATAAATGGGTCATCTAAAGANTATGGAGCTGGGATTGACTCNGCAATTANTCATACNCGCCGAATTTTG
GCAATCCTANANGCACTCTTTTCATTAAAACCATCTTCTGTGGGGACTCCATGGANTTACAGTTCTANTGANATA
ATTGCTGCGGCCATGGTTGCANCTCATATTTCCNAACTGTTCANACATTC cDNA1 3' end sequence (polyA tail removed)

CATCAAAGTAACTCCAAAACTGCCAAACAAACAGAGAAGAACGGGAATGAATAGTCCTCCTATCGGATTCTTTCA
AACGCCGCCTCAATAGAACTGGGAAAGCCGATATCCAAAACTGTTTAAACTGGGGAAGCTCAACAGCTTGCTTCC
AACAACTATGCCTAACTCAGTTTTTGACACTGCGGCTCGGGGAATCGGCTGTACTATATCCTTGTCCCAATAACG
AGCACCCACTTTTGTTTTTGGTAAATTTTAGTTTTAGACAAAACATTTGGACGTAGACCAAGAAGAATATATATA
TAGTTTGTTGTATGTAATGTTGTAATGATGAGTGACTGACGCAATCACTCCCACCGGCGTTGGATTTGCTCTCGC
TCGGTGTCTTATATAACTCAACCTCTTTCTGTACATTTTAAATGACGAAGTAGCTCA(polyA tail)

FIGURE 4

```
15401  TCTCGATTGA TAGTAGAAGA AAGGTGTTAG TTAGATTGTT CGTTCATCTA
15451  GTTGGGGTTT AGTTTCGGTT CCTGGATGGC TAGTTCATCT TCATCTGAGA
15501  GATGGATCGA TGGTCTTCAG TTCTCTTCCT TGTTATGGCC TCCGCCACGA
15551  GATCCTCAAC AACATAAGGA TCAAGTCGTT GCTTATGTTG AATATTTTGG
15601  TCAATTTACA TCAGAGCAAT TCCCAGATGA CATTGCTGAG GTACTTGATA
15651  CCTAATGAGT TTAATAAGAG TATTCTCTTA GTAGTGACGT TTTGATTCAT
15701  GTATAATTTA TCTGTATCAG TTGGTCCGGC ATCAGTATCC ATCAACTGAG
15751  AAGCGACTTT TAGACGATGT GCTGGGTATG ATCAACATTT ATGATCCACA
15801  CTTCTCTTTT TGTGTGTGAA TGTCTATCTG ATTTTCGTTT TCTGATGAAA
15851  CAGCGATGTT TGTCCTTCAT CATCCGGAGC ATGGTCATGC AGTCATTCTT
15901  CCAATCATTT CATGTCTTAT TGATGGCTCG TTGGTGTACA GCAAGGAAGC
15951  TCATCCGTTT GCCTCTTTCA TATCTTTAGT TTGCCCAAGT AGTGAGGTAT
16001  ATAATAGCTG TCTAGTATCA TGCTTACTGA TTTGGTGTAA CCTATACCAT
16051  TTTGTGCTAA CATGTTCACT ATCCTAACAG AATGACTATT CGGAGCAATG
16101  GGCTTTGGCA TGTGGAGAAA TCCTTCGCAT TTTGACTCAT TACAACCGTC
16151  CCATTTATAA AACTGAGCAG CAAAATGGAG ATACAGAGAG AAATTGTCTG
16201  AGCAAAGCTA CAACTAGTGG TTCTCCGACT TCAGAGCCTA AGGCTGGATC
16251  ACCAACACAG CATGAAAGGA AACCTTTAAG GCCTTTGTCT CCATGGATCA
16301  GTGATATACT ACTTGCTGCT CCTCTTGGTA TAAGAAGTGA CTATTTCCGA
16351  TGGTAAGTAG ACTCTGTTAC TGATGCTTCT ATGTGTTCAT GCGCCGGCCT
16401  CCTTCTTTTA TTTTGGTCTC TCTGCTGAGG TCTATGTATT GAGGTTCTGT
16451  AGTGGATTAA GCTTACTGAC AACTAAAAAT GTTGCTTATT ATTTACAGGT
16501  GTAGTGGTGT AATGGGTAAA TATGCTGCTG GAGAGCTCAA GCCGCCAACC
16551  ATTGGTGAGT TCAAGAATTC CATGTTAATA TCCCCTGGAA CTGGATTTTG
16601  ATGATAATTC TGATCAATAG AGTTGTTCTA TCACTTCGTT CATAAATGTG
16651  TATCCATCAC CTGTGGCTAT AGAATGTGTT TTGAGTTGCT TCCTATAACT
16701  TTCATGTTGT CCTACTTTGG CAGCTTCTCG AGGATCTGGT AAACATCCTC
16751  AACTGATGCC TTCAACCCCA AGATGGGCTG TTGCTAATGG AGCTGGTGTC
16801  ATACTGAGTG TTTGTGATGA TGAAGTTGCT CGATATGAGA CTGCTACGCT
16851  GACAGCGGTC GCTGTCCCTG CACTTCTTCT TCCTCCGCCA ACGACATCCT
16901  TAGATGAGCA TCTAGTTGCT GGCCTTCCAG CTCTTGAACC ATATGCACGT
16951  TTGTTTCATA GGTATTGTTT CTGGGCTTAC CCTTTCAATT AGGGTTTATT
17001  GGTAGTAGTC TGTTGCTAGT TTTAAGGTTG TGCTTCCTCG AATCCCTAGA
17051  TCAGAATTGT TTTCTCACTT TCCTGTTATA CTGTCAGATA CTATGCCATT
17101  GCAACTCCAA GTGCTACGCA GAGACTTCTT CTTGGACTCT TAGAAGCACC
17151  ACCGTCGTGG GCTCCAGATG CACTTGATGC TGCTGTACAG CTTGTGGAAC
17201  TCCTTCGAGC TGCTGAAGAT TATGCATCTG GTGTAAGGGT AAGCGTAATA
17251  TGAATCTCTT AATTACCCTC CAGAAAGCTA ATTGTGTCCC TTGTTATAAA
17301  AAAAGTCAGC TTTGGTATGT CATCAAAGAA ATCAGCTTTG ATCACATTCT
17351  TTTTCTTGGT GCAGCTACCC AGGAACTGGA TGCATTTGCA CTTCTTGCGG
17401  GCTATAGGAA TTGCTATGTC TATGAGGGCA GGTGTTGCTG CTGATGCTGC
17451  AGCCGCTTTG CTTTTCCGCA TACTCTCACA GCCGGCACTG CTTTTTCCTC
17501  CGCTAAGTCA AGTTGAGGGA GTAGAAATTC AGCACGCGCC TATTGGTGGC
17551  TACAGTTCAA ATTACAGAAA ACAGGCATGG TTCCTCTTTA TATTTTTCTG
17601  CTATTCCATC TCTGATATGC GATTGGCATT CTACTAGAAA ATTATATTGA
17651  AACTGACTCA TTTCATCTCA ACAGATAGAA GTTCCTGCAG CAGAAGCAAC
17701  CATTGAAGCC ACTGCCCAAG GAATTGCCTC AATGCTTTGT GCTCATGGTC
17751  CTGAAGTTGA GTGGAGAATT TGCACTATAT GGGAAGCTGC TTATGGTTTG
17801  ATCCCTTTAA ATTCTTCGGC GGTTGATCTT CCCGAAATCA TAGTTGCTAC
17851  CCCACTGCAA CCTCCTATCT TGTCATGAAA TTTATACATT CCACTCCTCA
17901  AAGTACTTGA ATATCTTCCA CGGGGGAGTC CTTCGGAAGC ATGCTTGATG
17951  AAAATATTTG TTGCCACTGT GGAAACAATA CTCAGTAGAA CTTTTCCGCC
18001  TGAATCTTCC AGGGAACTAA CCAGAAAAGC TAGATCGAGT TTTACCACAA
18051  GATCAGCGAC CAAAAATCTT GCTATGTCTG AGCTTCGTGC TATGGTCCAT
18101  GCTCTCTTTT TAGAATCATG CGCTGGTGTG GAATTAGCTT CACGCCTACT
18151  TTTTGTTGTG TTGACTGTAT GTGTTAGCCA TGAAGCACAG TCTAGTGGTA
18201  GCAAGAGACC GAGAAGTGAA TATGCTAGTA CTACTGAAAA TATTGAGGCG
18251  AATCAACCTG TATCTAACAA TCAAACTGCT AACCGTAAAA GTAGGAATGT
```

FIGURE 5A

```
18301  CAAGGGACAG GGACCTGTGG CAGCATTTGA TTCATACGTT CTTGCTGCTG
18351  TTTGTGCTCT TGCCTGTGAG GTTCAGCTGT ATCCTATGAT CTCTGGTGGG
18401  GGGAACTTTT CCAATTCTGC CGTGGCTGGA ACTATTACAA AGCCTGTAAA
18451  GATAAATGGG TCATCTAAAG AGTATGGAGC TGGGATTGAC TCGGCAATTA
18501  GTCATACGCG CCGAATTTTG GCAATCCTAG AGGCACTCTT TTCATTAAAA
18551  CCATCTTCTG TGGGGACTCC ATGGAGTTAC AGTTCTAGTG AGATAGTTGC
18601  TGCGGCCATG GTTGCAGCTC ATATTCCGA  ACTGTTCAGA CGTTCAAAGG
18651  CCTTGACGCA TGCATTGTCT GGGTTGATGA GATGTAAGTG GGATAAGGAA
18701  ATTCATAAAA GAGCATCATC ATTATATAAC CTCATAGATG TTCACAGCAA
18751  AGTTGTTGCC TCCATTGTTG ACAAAGCTGA ACCCTTGGAA GCCTACCTTA
18801  AGAATACACC GGTTCAGAAG GATTCTGTGA CCTGTTTAAA CTGGAAACAA
18851  GAGAACACAT GTGCAAGCAC CACATGCTTT GATACAGCGG TGACATCCGC
18901  CTCAAGGACT GAAATGAATC CAAGAGGAAA CCATAAGTAT GCTAGACATT
18951  CAGATGAAGG CTCAGGGAGA CCCTCAGAGA AGGGTATCAA AGATTTCCTC
19001  TTGGATGCTT CTGATCTTGC GAATTTCCTC ACAGCTGATA GACTCGCAGG
19051  GTTCTATTGT GGTACACAAA AGCTTTTGAG GTCAGTGCTT GCAGAGAAAC
19101  CGGAGCTGTC TTTCTCCGTT GTTTCACTGT TATGGCACAA ACTGATTGCT
19151  GCTCCTGAAA TCCAGCCCAC CGCAGAAAGC ACCTCTGCGC AACAAGGATG
19201  GAGACAGGTA AACCTCAGCA CTTCTATTTC CCAGCTCGCT TACAGTTTCC
19251  TTGGTAGTTC TTTACTAATC CAATTAAGTC GCTCGACTTC ATACACTGAT
19301  CATATTTTTT ATATATCAGG TTGTTGATGC GCTATGCAAT GTCGTATCTG
19351  CAACGCCAGC GAAAGCAGCA GCAGCAGTTG TCCTTCAGGT CCAAATTACT
19401  CTTTGACTTT TTATTTCATT TGTCAGGAAT GCAACACCTG TGTAAAGATT
19451  AAACTGCGGA AAACCTATGG CCTGTGTTAA TGTTTTATAA TGCTTGGTTC
19501  ACTCATTTGA TCTCTCATGA ATTTATAAAA ATTAAGCTTG GAATTTATAT
19551  GCAACACTTG TTTTAATATG CCAAGGATAG GAAATAAGGA AGAAAAAATC
19601  TGTGTAAAAT AATGGCTTGT TTCAAGCTCA TATGTTGAAG GATTTACTCT
19651  AATGCTCTAT TGTCTGAAAT GGTCTTGTGT TATTTACAGG CTGAAAGGGA
19701  GTTGCAGCCT TGGATCGCCA AAGATGATGA AGAAGGCCAA AAAATGTGGA
19751  AAATCAACCA ACGGATAGTC AAAGTGTTGG TGGAACTCAT GCGCAATCAT
19801  GACAGGCCTG AGTCACTGGT GATTCTCGCA AGTGCATCAG ATCTTCTTCT
19851  GCGGGCAACT GATGGAATGC TTGTTGATGG AGAAGCTTGT ACATTACCTC
19901  AACTTGAGGT ACTGCACTGT TATAGATTGC TCTTCAATGC CCTTCTTCGG
19951  GCTAGAGTAA TAATCATTTT CTGATTCCAC TGTATTTTAA ACTTTTGCAG
20001  CTACTTGAAG CCACGGCAAG AGCAATACAG CCGGTGCTAG CTTGGGGGCC
20051  ATCTGGACTA GCAGTGGTCG ACGTTTATC  CAATCTATTG AAGGTAAAAG
20101  CAGAATCGAA CAGAGCCTAT GGTTTCCTGC GTCGATTGTA GATGATCAGT
20151  AGTAGGTCCA GTTACCAAAG TGCTTAACCT TGTTCACATC TTTTTGCTTC
20201  TATGCAGTGT CGTCTACCAG CAACAATACG GTGCCTTTCA CACCCAAGTG
20251  CACACGTACG TGCCTTAAGC ACGTCAGTAC TACGTGATAT CATGAACCAA
20301  AGCTCCATAC CCATCAAAGT AACTCCAAAA CTGCCAACAA CAGAGAAGAA
20351  CGGAATGAAT AGTCCGTCCT ATCGATTCTT CAACGCCGCC TCAATAGACT
20401  GGAAAGCCGA TATCCAAAAC TGTTTAAACT GGGAAGCTCA CAGCTTGCTC
20451  TCCACAACTA TGCCTACTCA GTTCTCGAC  ACTGCGGCTC GGGAACTCGG
20501  CTGTACTATA TCCTTGTCCC AATAACGAGC ACCCACTTTT GTTTTGGTA
20551  AATTTTAGTT CTCTAGACAA AACATTTGGA CGTAGACCAA GAAGAATATA
20601  TATATAGTTT GTTGTATGTA ATGTTGTAAT GATGAGTGAC TGACGCAATC
20651  ACTCCCACCG GCGTTGGATT TGCTCTCGCT CGGTGTCTTA TATAACTCAA
20701  CCTCTTCTCT GTACATTTTA AATGACGAAG TAGCTCAATC TTTTTTTTTG
20751  TGCGTCTGGT GTTTAGTCTT CAGTGGATTC TAAATCGTAA TGTATAGAAG
```

FIGURE 5B

MASSSSSERWIDGLQFSSLLWPPPRDPQQHKDQVVAYVEYFGQF
TSEQFPDDIAELVRHQYPSTEKRLLDDVLAMFVLHHPEHGHAVILPIISCLIDGSLVY
SKEAHPFASFISLVCPSSENDYSEQWALACGEILRILTHYNRPIYKTEQQNGDTERNC
LSKATTSGSPTSEPKAGSPTQHERKPLRPLSPWISDILLAAPLGIRSDYFRWCSGVMG
KYAAGELKPPTIEHPQLMPSTPRWAVANGAGVILSVCDDEVARYETATLTAVAVPALL
LPPPTTSLDEHLVAGLPALEPYARLFHRYYAIATPSATQRLLLGLLEAPPSWAPDALD
AAVQLVELLRAAEDYASGVRLPRNWMHLHFLRAIGIAMSMRAGVAADAAAALLFRILS
QPALLFPPLSQVEGVEIQHAPIGGYSSNYRKQIEVPAAEATIEATAQGIASMLCAHGP
EVEWRICTIWEAAYGLIPLNSSAVDLPEIIVATPLQPPILSWNLYIPLLKVLEYLPRG
SPSEACLMKIFVATVETILSRTFPPESSRELTRKARSSFTTRSATKNLAMSELRAMVH
ALFLESCAGVELASRLLFVVLTVCVSHEAQSSGSKRPRSEYASTTENIEANQPVSNNQ
TANRKSRNVKGQGPVAAFDSYVLAAVCALACEVQLYPMISGGGNFSNSAVAGTITKPV
KINGSSKEYGAGIDSAISHTRRILAILEALFSLKPSSVGTPWSYSSSEIVAAAMVAAH
ISELFRRSKALTHALSGLMRCKWDKEIHKRASSLYNLIDVHSKVVASIVDKAEPLEAY
LKNTPVQKDSVTCLNWKQENTCASTTCFDTAVTSASRTEMNPRGNHKYARHSDEGSGR
PSEKGIKDFLLDASDLANFLTADRLAGFYCGTQKLLRSVLAEKPELSFSVVSLLWHKL
IAAPEIQPTAESTSAQQGWRQVVDALCNVVSATPAKAAAAVVLQAERELQPWIAKDDE
EGQKMWKINQRIVKVLVELMRNHDRPESLVILASASDLLLRATDGMLVDGEACTLPQL
ELLEATARAIQPVLAWGPSGLAVVDGLSNLLKCRLPATIRCLSHPSAHVRALSTSVLR
DIMNQSSIPIKVTPKLPTTEKNGMNSPSYRFFNAASIDWKADIQNCLNWEAHSLLSTT
MPTQFLDTAARELGCTISLSQ

FIGURE 6

```
   1  ATGGCTAGTT CATCTTCATC TGAGAGATGG ATCGATGGTC TTCAGTTCTC
  51  TTCCTTGTTA TGGCCTCCGC CACGAGATCC TCAACAACAT AAGGATCAAG
 101  TCGTTGCTTA TGTTGAATAT TTTGGTCAAT TTACATCAGA GCAATTCCCA
 151  GATGACATTG CTGAGTTGGT CCGGCATCAG TATCCATCAA CTGAGAAGCG
 201  ACTTTTAGAC GATGTGCTGG CGATGTTTGT CCTTCATCAT CCGGAGCATG
 251  GTCATGCAGT CATTCTTCCA ATCATTTCAT GTCTTATTGA TGGCTCGTTG
 301  GTGTACAGCA AGGAAGCTCA TCCGTTTGCC TCTTTCATAT CTTTAGTTTG
 351  CCCAAGTAGT GAGAATGACT ATTCGGAGCA ATGGGCTTTG GCATGTGGAG
 401  AAATCCTTCG CATTTTGACT CATTACAACC GTCCCATTTA TAAAACTGAG
 451  CAGCAAAATG GAGATACAGA GAGAAATTGT CTGAGCAAAG CTACAACTAG
 501  TGGTTCTCCG ACTTCAGAGC CTAAGGCTGG ATCACCAACA CAGCATGAAA
 551  GGAAACCTTT AAGGCCTTTG TCTCCATGGA TCAGTGATAT ACTACTTGCT
 601  GCTCCTCTTG GTATAAGAAG TGACTATTTC CGATGGTGTA GTGGTGTAAT
 651  GGGTAAATAT GCTGCTGGAG AGCTCAAGCC GCCAACCATT GCTTCTCGAG
 701  GATCTGGTAA ACATCCTCAA CTGATGCCTT CAACCCCAAG ATGGGCTGTT
 751  GCTAATGGAG CTGGTGTCAT ACTGAGTGTT TGTGATGATG AAGTTGCTCG
 801  ATATGAGACT GCTACGCTGA CAGCGGTCGC TGTCCCTGCA CTTCTTCTTC
 851  CTCCGCCAAC GACATCCTTA GATGAGCATC TAGTTGCTGG CCTTCCAGCT
 901  CTTGAACCAT ATGCACGTTT GTTTCATAGA TACTATGCCA TTGCAACTCC
 951  AAGTGCTACG CAGAGACTTC TTCTTGGACT CTTAGAAGCA CCACCGTCGT
1001  GGGCTCCAGA TGCACTTGAT GCTGCTGTAC AGCTTGTGGA ACTCCTTCGA
1051  GCTGCTGAAG ATTATGCATC TGGTGTAAGG CTACCCAGGA ACTGGATGCA
1101  TTTGCACTTC TTGCGGGCTA TAGGAATTGC TATGTCTATG AGGGCAGGTG
1151  TTGCTGCTGA TGCTGCAGCC GCTTTGCTTT TCCGCATACT CTCACAGCCG
1201  GCACTGCTTT TTCCTCCGCT AAGTCAAGTT GAGGGAGTAG AAATTCAGCA
1251  CGCGCCTATT GGTGGCTACA GTTCAAATTA CAGAAAACAG ATAGAAGTTC
1301  CTGCAGCAGA AGCAACCATT GAAGCCACTG CCCAAGGAAT TGCCTCAATG
1351  CTTTGTGCTC ATGGTCCTGA AGTTGAGTGG AGAATTTGCA CTATATGGGA
```

FIGURE 8A

```
1401  AGCTGCTTAT GGTTTGATCC CTTTAAATTC TTCGGCGGTT GATCTTCCCG
1451  AAATCATAGT TGCTACCCCA CTGCAACCTC CTATCTTGTC ATGGAATTTA
1501  TACATTCCAC TCCTCAAAGT ACTTGAATAT CTTCCACGGG GGAGTCCTTC
1551  GGAAGCATGC TTGATGAAAA TATTTGTTGC CACTGTGGAA ACAATACTCA
1601  GTAGAACTTT TCCGCCTGAA TCTTCCAGGG AACTAACCAG AAAAGCTAGA
1651  TCGAGTTTTA CCACAAGATC AGCGACCAAA AATCTTGCTA TGTCTGAGCT
1701  TCGTGCTATG GTCCATGCTC TCTTTTTAGA ATCATGCGCT GGTGTGGAAT
1751  TAGCTTCACG CCTACTTTTT GTTGTGTTGA CTGTATGTGT TAGCCATGAA
1801  GCACAGTCTA GTGGTAGCAA GAGACCGAGA AGTGAATATG CTAGTACTAC
1851  TGAAAATATT GAGGCGAATC AACCTGTATC TAACAATCAA ACTGCTAACC
1901  GTAAAAGTAG GAATGTCAAG GGACAGGGAC CTGTGGCAGC ATTTGATTCA
1951  TACGTTCTTG CTGCTGTTTG TGCTCTTGCC TGTGAGGTTC AGCTGTATCC
2001  TATGATCTCT GGTGGGGGGA ACTTTTCCAA TTCTGCCGTG GCTGGAACTA
2051  TTACAAAGCC TGTAAAGATA AATGGGTCAT CTAAAGAGTA TGGAGCTGGG
2101  ATTGACTCGG CAATTAGTCA TACGCGCCGA ATTTTGGCAA TCCTAGAGGC
2151  ACTCTTTTCA TTAAAACCAT CTTCTGTGGG GACTCCATGG AGTTACAGTT
2201  CTAGTGAGAT AGTTGCTGCG GCCATGGTTG CAGCTCATAT TTCCGAACTG
2251  TTCAGACGTT CAAAGGCCTT GACGCATGCA TTGTCTGGGT TGATGAGATG
2301  TAAGTGGGAT AAGGAAATTC ATAAAAGAGC ATCATCATTA TATAACCTCA
2351  TAGATGTTCA CAGCAAAGTT GTTGCCTCCA TTGTTGACAA AGCTGAACCC
2401  TTGGAAGCCT ACCTTAAGAA TACACCGGTT CAGAAGGATT CTGTGACCTG
2451  TTTAAACTGG AAACAAGAGA ACACATGTGC AAGCACCACA TGCTTTGATA
2501  CAGCGGTGAC ATCCGCCTCA AGGACTGAAA TGAATCCAAG AGGAAACCAT
2551  AAGTATGCTA GACATTCAGA TGAAGGCTCA GGGAGACCCT CAGAGAAGGG
2601  TATCAAAGAT TTCCTCTTGG ATGCTTCTGA TCTTGCGAAT TTCCTCACAG
2651  CTGATAGACT CGCAGGGTTC TATTGTGGTA CACAAAAGCT TTTGAGGTCA
2701  GTGCTTGCAG AGAAACCGGA GCTGTCTTTC TCCGTTGTTT CACTGTTATG
2751  GCACAAACTG ATTGCTGCTC CTGAAATCCA GCCCACCGCA GAAAGCACCT
2801  CTGCGCAACA AGGATGGAGA CAGGTTGTTG ATGCGCTATG CAATGTCGTA
```

FIGURE 8B

```
2851  TCTGCAACGC CAGCGAAAGC AGCAGCAGCA GTTGTCCTTC AGGCTGAAAG

2901  GGAGTTGCAG CCTTGGATCG CCAAAGATGA TGAAGAAGGC CAAAAAATGT

2951  GGAAAATCAA CCAACGGATA GTCAAAGTGT TGGTGGAACT CATGCGCAAT

3001  CATGACAGGC CTGAGTCACT GGTGATTCTC GCAAGTGCAT CAGATCTTCT

3051  TCTGCGGGCA ACTGATGGAA TGCTTGTTGA TGGAGAAGCT TGTACATTAC

3101  CTCAACTTGA GCTACTTGAA GCCACGGCAA GAGCAATACA GCCGGTGCTA

3151  GCTTGGGGGC CATCTGGACT AGCAGTGGTC GACGGTTTAT CCAATCTATT

3201  GAAGTGTCGT CTACCAGCAA CAATACGGTG CCTTTCACAC CCAAGTGCAC

3251  ACGTACGTGC CTTAAGCACG TCAGTACTAC GTGATATCAT GAACCAAAGC

3301  TCCATACCCA TCAAAGTAAC TCCAAAACTG CCAACAACAG AGAAGAACGG

3351  AATGAATAGT CCGTCCTATC GATTCTTCAA CGCCGCCTCA ATAGACTGGA

3401  AAGCCGATAT CCAAAACTGT TTAAACTGGG AAGCTCACAG CTTGCTCTCC

3451  ACAACTATGC CTACTCAGTT TCTCGACACT GCGGCTCGGG AACTCGGCTG

3501  TACTATATCC TTGTCCCAAT AA
```

FIGURE 8C

```
  1  MASSSSSERW  IDGLQFSSLL  WPPPRDPQQH  KDQVVAYVEY  FGQFTSEQFP
 51  DDIAELVRHQ  YPSTEKRLLD  DVLAMFVLHH  PEHGHAVILP  IISCLIDGSL
101  VYSKEAHPFA  SFISLVCPSS  ENDYSEQWAL  ACGEILRILT  HYNRPIYKTE
151  QQNGDTERNC  LSKATTSGSP  TSEPKAGSPT  QHERKPLRPL  SPWISDILLA
201  APLGIRSDYF  RWCSGVMGKY  AAGELKPPTI  ASRGSGKHPQ  LMPSTPRWAV
251  ANGAGVILSV  CDDEVARYET  ATLTAVAVPA  LLLPPPTTSL  DEHLVAGLPA
301  LEPYARLFHR  YYAIATPSAT  QRLLLGLLEA  PPSWAPDALD  AAVQLVELLR
351  AAEDYASGVR  LPRNWMHLHF  LRAIGIAMSM  RAGVAADAAA  ALLFRILSQP
401  ALLFPPLSQV  EGVEIQHAPI  GGYSSNYRKQ  IEVPAAEATI  EATAQGIASM
451  LCAHGPEVEW  RICTIWEAAY  GLIPLNSSAV  DLPEIIVATP  LQPPILSWNL
501  YIPLLKVLEY  LPRGSPSEAC  LMKIFVATVE  TILSRTFPPE  SSRELTRKAR
551  SSFTTRSATK  NLAMSELRAM  VHALFLESCA  GVELASRLLF  VVLTVCVSHE
601  AQSSGSKRPR  SEYASTTENI  EANQPVSNNQ  TANRKSRNVK  GQGPVAAFDS
651  YVLAAVCALA  CEVQLYPMIS  GGGNFSNSAV  AGTITKPVKI  NGSSKEYGAG
701  IDSAISHTRR  ILAILEALFS  LKPSSVGTPW  SYSSSEIVAA  AMVAAHISEL
751  FRRSKALTHA  LSGLMRCKWD  KEIHKRASSL  YNLIDVHSKV  VASIVDKAEP
801  LEAYLKNTPV  QKDSVTCLNW  KQENTCASTT  CFDTAVTSAS  RTEMNPRGNH
851  KYARHSDEGS  GRPSEKGIKD  FLLDASDLAN  FLTADRLAGF  YCGTQKLLRS
901  VLAEKPELSF  SVVSLLWHKL  IAAPEIQPTA  ESTSAQQGWR  QVVDALCNVV
951  SATPAKAAAA  VVLQAERELQ  PWIAKDDEEG  QKMWKINQRI  VKVLVELMRN
```

FIGURE 9A

```
1001  HDRPESLVIL  ASASDLLLRA  TDGMLVDGEA  CTLPQLELLE  ATARAIQPVL

1051  AWGPSGLAVV  DGLSNLLKCR  LPATIRCLSH  PSAHVRALST  SVLRDIMNQS

1101  SIPIKVTPKL  PTTEKNGMNS  PSYRFFNAAS  IDWKADIQNC  LNWEAHSLLS

1151  TTMPTQFLDT  AARELGCTIS  LSQ
```

FIGURE 9B

Homology to Rice est C73052 (the predicted GI sequence is shown on the bottom line)

```
  8 QASSCESMEKRANGSPRNEPDRKPLRPLSPWITDILLAAPLGIRSDYFRW  57
    .|..  |                : :|||||||||||.||||||||||||||||
163 KATTSGSPTSEPKAGSPTQHERKPLRPLSPWISDILLAAPLGIRSDYFRW 212

58 CGGVMGKYAAGGELKPPTTAYSRGSGKHPQLMPSTPRWAVANGAGVILSV 107
    | ||||||||  ||||||               .|||||||||||||||||||||
213 CSGVMGKYAA.GELKPPTI.......EHPQLMPSTPRWAVANGAGVILSV 254

108 CDEEVPRY 115
    ||:|| ||
255 CDDEVARY 262
```

Homology to Rice est C72988 (the predicted GI sequence is shown on the bottom line)

```
  1 VSHQALPGGSKRP.....TGSDNHSSEEVTNDSRLTNGRNRCKKRQGPVA  45
    |||:|    |||||      ..:|  . :   ....  | :.|  |  |||||
591 VSHEAQSSGSKRPRSEYASTTENIEANQPVSNNQTANRKSRNVKGQGPVA 640

46 TFDSYVLAAVCALSCELQLFPFISKNGNHSNLKDSIKIVIPGKTTGISNE  95
    |||||||||||||.||.||:| ||  || ||   .  |   |||  |  |
641 AFDSYVLAAVCALACEVQLYPMISGGGNFSNSAVAGTITKPVKINGSSKE 690

96 LHNSISSAILHTRRILGILEALFSLKPSSVGTSWSYSSNEIVAAAMVAAH 145
    |  |||  ||||||  |||||||||||||||||| |||||.|||||||||||
691 YGAGIDSAISHTRRILAILEALFSLKPSSVGTPWSYSSSEIVAAAMVAAH 740

146 VSELFRRS 153
    :|||||||
741 ISELFRRS 748
```

Homology to Rice est D40642 (the predicted GI sequence is shown on the bottom line)

```
   4 QAEKDLQPWIARDDEQGQKMWRVNQRIVKLIAELMRNHDSPEALVILASA   53
     |||::|||||||:|||:|||||::|||||.: |||||| ||.|||||||
 958 QAERELQPWIAKDDEEGQKMWKINQRIVKVLVELMRNHDRPESLVILASA 1007

54 SDLLLRATDGMLVDGEACTLPQLELLEVTARAVHLIVEWGDSGVSVADGL  103
     ||||||||||||||||||||||||||||||||:  :.  || ||..| |||
1008 SDLLLRATDGMLVDGEACTLPQLELLEATARAIQPVLAWGPSGLAVVDGL 1057

104 SNLLKCRLSTTIRCLS  119
     ||||||||  ||||||
1058 SNLLKCRLPATIRCLS 1073
```

FIGURE 10

```
   1  CgGAAGCCAT TGaGGCCACT ATCTCCTTGG ATCACAgACA TATTGcTtGc
  51  TGcACCTCTG GGTATTAgAA GTGACTATtT TAgATGGTGT gGTGgAgTCA
 101  TGGgAAAAtA CgCAgCTGGt GGAgAATTGA AGCCTcCAAC AACTGcTTAC
 151  AGCCGAGGAT CTgggAAGcA CCCacaactT atgcCatcCa cgcccAgaTg
 201  GGCTGcTGcc aATGGagctg GagtTatact aAgtgtctgt gatgagGaAg
 251  tagctcgtTa tgagacagca AAtTTgactg cgGcagctgT tCctgcactt
 301  ctaTtaCctc caccgaCcac accattGgac gAacaTTTGG TtgcGGggcT
 351  CCcTCctcTt GaaCcatatg ctcgcTtGTT tcatAgAtac tatgcAaTtG
 401  ctactCcAag tGcTaCCcAA aggttgcTTT TtGgtcTtcT cgaGgcaCca
 451  CcatcaTGGG CCCcagatgc acTtgatgca goagtACAGC TTGTTGAACT
 501  CCTTAGAGCA GCGGAAGATT ACGATTCTGG CATGCGGCTT CCAAAGAACT
 551  GGATGCATCT TCATTTCCTG CGTGCTATTG GAACTGCAAT GtCAATGAGA
 601  GCTGGtATCG CTGCTGATaC GtCTGCTGcT TTACTTTTCC GAAtACTcTc
 651  CCAAcCGaCA TTACTTTTTC CTcCACtgaG ACATgcCgAA GGaGTTGAaC
 701  TcCATcATGA GcCacTagGT GGCTATGTat catcGtaCAA AAGGCAgcTG
 751  gAAGTtCCtG caTctgAAGC CaCtATTgAT GCCActGCGC AAGGCATtGc
 801  TTCCatgcTA TGTGCTCATG GTCCCGATgt TGAGTGGAGA ATATGtACCA
 851  TCTGGgAggC TgCGTATGGT TTgCTACCCt tgAGTTCATC AGCAGTTGAT
 901  TtGCCTGAAA TTGTTGTAGC tGCTCCACTT CAGCCACctA CTTTGTCATG
 951  GAGCCTATAC TTGCCATTGT TGaAAGTATT TgAGTATTTA CCTCGTGGGA
1001  GTCCATCTGA AGCATGCCTT ATGAGAATTT TTGTGGCAAC AGTTGAAGCT
1051  ATACTGAGAA GAACTTTTCC ATCAGAAACC TCTGAACAAT CCAGGAAACC
1101  AAGAAGTCAA TCTAAGAACC TTGCTGTTGc TGAACTCCGA ACAATgATAC
1151  ATTCACTCTT TGTGGAGTCC TGTGCTTCAA TGGACCTTGC GTCCAgAtta
1201  CtAtTtgtag tAttaaCtGT ttGCgtcAGT CATCAAGccT tGccTgGggg
1251  aAGTaaaagG ccAACTGGTA GTGATAATCA TTCCTCTGAG GAGGTCacaA
1301  atGattcgag ATTAaccaAt GGAAGAAACA GATGTAAGAA GAGACAAGGA
1351  CCAGTTGCTA CATTCGACTC ATACGTTCTA GCAGCCGTTT GTGCCTTATC
1401  TTGTGAGCTC CAGCTGTTCC CTTTTATTTC CAAGAATGGG AACCATTCAA
1451  ATCTGAAGGA CTCCATAAAG ATAGTCATAC CTGGAAAAAC CACTGGTATC
1501  AGTAACGAGC TACACAATAG CATTAGCtCA GCGATTCtTC ATACTCGTAG
```

FIGURE 11A

```
1551 AATACTTGGC ATCTTGGAAG CTCTGTTCTC CTTGAAGCCA TCATCTGTTG
1601 GTACTTCATG GAGTTATAGT TCAAATGAGA TTGTTGCAgC AGCTATGGTT
1651 GCTGCTCATG TTTCTGAGTT ATTTCGTCgA TCCAgGCCAT GCTTAAATGC
1701 ACTGTCTGCG CTgaAGcAAt gcAAGtggGA TGcTGAGATT TCTAcCAGGg
1751 CATCATCCCT TTACCAtTTG ATTGACTTGC ATGGTAAAAC AGTGACCTcC
1801 ATTGtGAACA AAGCTGAGCC TCTAGaAGCT CACCTGACCC TTACACCAGT
1851 AAAAAGGAT GAACCTCCCA TTGAGGAAAA GAACATTAAC TCATCAGATG
1901 GTGGTGCATT GGAAAAAAAG GATGCTTCAA GATCACACAG GAAAAATGGT
1951 TTTGCAAGAC CACTCTTGAA ATGTGCAGAA GATGTTATAC TAAATGGTGA
2001 TGTCGCAAGT ACTTCTGGGA AAGCCATTGC AAGTTTACAG GTGGAAGCTT
2051 CTGATTTGGC AAACTTCCTc ACCATGGacC GAAATGGGGG TtACAGAGGT
2101 TCTCAAACTC TCcTAAGATC TGTACTGTCA GAGAAGCAGG AGCTATGCTT
2151 CTCTGTTGTC TCATTGCTCT GGCAGAAGCT CATTGCATCT CCCGAAATGC
2201 AgATGtCTGC AGAAAGTaCA TCAGCTCATC AGGGtTGGAG AAAGGTTGTG
2251 GATgCgCTTt GTGAcATTGT TTCAgCCTcA CCGACCAAGG CTTCAGCTGC
2301 TATCgTTCtg CAGGCCGAGA AGGACTTGCA GCCCTGGATT GCTCGAGATG
2351 ATGAGCAAGG TCAGAAGATG TGGAGAGTCA ACCAGCGAAT AGTTAAGCTG
2401 ATAGCAGAGC TTATGAGGAA CCACgATAgC cCAgaAgCat TgGTGaTCct
2451 tgcTagtGCT TCAGATCTTC ttCTTcGAGC AACTGATGGA ATGCTTGTTg
2501 ATGGTgAAGC TTGtACtTTa CCaCAATtAG AGCTATTGGa AGTaaCCGcC
2551 aGAgcAGtCc ATcTCATCGT cGAATGGGGA GATTcAGGTg tATCCGtCGC
2601 TgATGGCCTC TCCAATCTGC TGAAGTgCCG TCTATCAACC ACCATCCGCT
2651 GTCTTTCGCA CCCCAGCGCG CATGTCCGTG CACTCAGCAT GTCCGTCCTT
2701 CGCGACATCT TGAACAGCGG ACAAATAAAC TCCAGTAAGC TCATCCAAGG
2751 GGAACACCGG AATGGCATCC AGAGCCCAAC CTACCAGTGC TTGGCAGCAA
2801 GCATCATCAA CTGGCAAgCC GATGTGGAGA GATGCATAGA GTGGAAGCC
2851 CACAGcCGcC GCGCCAcCGG GCTGACgCtC gCCTTCcTCA cCGCggCgAA
2901 GgaGcTCgGc TGCCCACTCA CTTgCTGACA A
```

FIGURE 11B

```
  1  RIPLRPLSPW ITDILLAAPL GIRSDYFRWC GGVMGKYAAG GELKPPTTAY
 51  SRGSGKBPQL MPSTPRWAVA NGAGVILSVC DREVARYETA MLTAAAVPAL
101  LLPPPTTPLD SHLVAGLPPL EPYARLFHRY YAIATDSATQ RLLFGLLEAP
151  PSWAPDALDA AVQLVELLRA AEDYDSGMRL PIQNWMGLHFL RAIGTAMSMR
201  AGIAADTSAA LLFRILSQPT LLFPPLRHAE GVELEHEPLG GYVSSYKROL
251  EVPASEATID ATAQGIASML CAHGPDVEWR ICTIWEAAYG LLPLSSSAVD
301  LPEIVVAAPL QPPTLSWSLY LPLLKVFEYL PRGSPSEACL MRIFVATVEA
351  ILRRTFPSET SEQSRKPRSQ SKNLAVAELR TMIHSLFVES CASMDLASRL
401  LFVVLTVCVS HQALPGGSKR PTGSDNHSSE EVTNDSRLTN GRNRCKKRQG
451  PVATFDSYVL AAVCALSCEL QLFPFISENG NHSMLKDSIK IVIPGKTTGI
501  SNELHNSISS AILHTRRILG ILEALFSLKP SSVGTSWSYS SNEIVAAAMV
551  AAHVSELFRR SRPCLNALSA LKQCKWDAEI STRASSLYHL IDLHGKTVTS
601  IVNKAEPLEA HLTLTPVKKD EPPIEEKNIN SSDGGALEKK DASRSHRKNG
651  FARPLLKCAE DVILNGDVAS TSGKAIASLQ VEASDLANFL TMDRNGGYRG
701  SQTLLRSVLS EKQELCFSVV SLLWQKLIAS PEMQMSAEST SAHQGWRKVV
751  DALCDIVSAS PTKASAAIVL QAEKDLQPWI ARDDEQGQKM WRVNQRIVKL
801  IAELMRNHDS PEALVILASA SDLLLRATDG MLVDGEACTL PQLELLEVTA
851  RAVHLIVEWG DSGVSVADGL SNLLKCRLST TIRCLSHPSA HVRALSMSVL
901  RDILNSGQIN SSKLIQGEHR NGIQSPTYQC LAASIINWQA DVERCIEWEA
951  HSRRATGLTL AFLTAAKELG CPLTC*Q
```

FIGURE 12

```
           Gap Weight:    3.000      Average Match:    0.540
        Length Weight:    0.100      Average Mismatch: -0.396

Quality:  1110.3              Length:     997
                Ratio:   1.136                Gaps:      10
    Percent Similarity:  81.237      Percent Identity:  71.443

1 RKPLRPLSPWITDILLAAPLGIRSDYFRWCGGVMGKYAAGGELKPPTTAY  50
    |||||||||||.|||||||||||||||||||:|||||||| ||||||.|
184 RKPLRPLSPWISDILLAAPLGIRSDYFRWCSGVMGKYAA.GELKPPTIA. 231

51 SRGSGKHPQLMPSTPRWAVANGAGVILSVCDEEVARYETANLTAAAVPAL 100
    ||||||||||||||||||||||||||||||:||||||||.|||.|||||
232 SRGSGKHPQLMPSTPRWAVANGAGVILSVCDDEVARYETATLTAVAVPAL 281

101 LLPPPTTPLDEHLVAGLPPLEPYARLFHRYYAIATPSATQRLLFGLLEAP 150
    |||||||.|||||||||:||||||||||||||||||||||||||:||||||
282 LLPPPTTSLDEHLVAGLPALEPYARLFHRYYAIATPSATQRLLLGLLEAP 331

151 PSWAPDALDAAVQLVELLRAAEDYDSGMRLPKNWMHLHFLRAIGTAMSMR 200
    |||||||||||||||||||||.||:|||:|||||||||||||.|||||
332 PSWAPDALDAAVQLVELLRAAEDYASGVRLPRNWMHLHFLRAIGIAMSMR 381

201 AGIAADTSAALLFRILSQPTLLFPPLEHAEGVELHHEPLGGYVSSYKRQL 250
    ||:|||..|||||||||||.||||||.:.||||::|.|:|||  |.|::|:
382 AGVAADAAAALLFRILSQPALLPPPLSQVEGVEIQHAPIGGYSSNYRKQI 431

251 EVPASEATIDATAQGIASMLCAHGPDVEWRICTIWEAAYGLLPLSSSAVD 300
    ||||.||||:|||||||||||||||:||||||||||||||:||-|||||
432 EVPAAEATIEATAQGIASMLCAHGPEVEWRICTIWEAAYGLIPLNSSAVD 481

301 LPEIVVAAPLQPPTLSWSLYLPLLKVFEYLPRGSPSEACLMRIFVATVEA 350
    ||||:||-|||||.|||-||:||||||||:|||||||||||||||:||||||||-
482 LPEIIVATPLQPPILSWMLYIPLLKVLEYLPRGSPSEACLMKIFVATVST 531

351 ILRRTPPSETSEQ.......SRKPRSQSKNLAVAELRTMIHSLFVESCAS 393
    ||.||||.|.| :       |..||..||||:.|||.|:|.||:||||:
532 ILSRTPPESSRELTRKARSSFTTRSATKNLAMSELRAHVHALFLESCAG 581

394 SMDLASRLLFVVLTVCVSHQALPGGSKRP.....TGSDNHSSEEVTNDSR 438
```

FIGURE 13A

```
         ::|||||||||||||||:|  .:|||||          ...:|  ..:.....:..
  582 VELASRLLFVVLTVCVSHEAQSSGSKRPRSEYASTIENIEANQPVSNNQT 631

439 TNGRNRCKKRQGPVATFDSYVLAAVCALSCELQLFPFISKNGNHSNLKDS 488
         .| :.|  | |||||-||||||:||||| .||:||:|:|| .|| ||  .
  632 ANRKSRNVKGQGPVAAFDSYVLAAVCALACEVQLYPMISGGGNFSNSAVA 681

489 IKIVIPGKTTGISNELHNSISSAILHTRRILGILEALFSLKPSSVGTSWS 538
         .|. |.|.--| |.|.  .:|.||| |||||||:|||||||||||||-||
  682 GTITKPVKINGSSKEYGAGIDSAISHTRRILAILEALFSLKPSSVGTPWS 731

539 YSSNEIVAAAMVAAHVSELFRRSRPCLNALSALKQCKWDAEISTRASSLY 588
         |||-||||||||||:|||||||::  :|||:|..|||| || .||||||
  732 YSSSEIVAAAMVAAHISELFRRSKALTHALSGLMRCKWDKEIHKRASSLY 781

589 HLIDLHGKTVTSIVNKAEPLEAHLTLTPVKKDEPPI....EEKNINSSDG 634
         :|||:|:|.|.|||:||||||.|. |||.||....   :|....|...
  782 NLIDVHSKVVASIVDKAEPLEAYLKNTPVQKDSVTCLNWKQENTCASTTC 831

635 GALEKKDASRSHRKNGFARPLLKCAEDVILNGDVASTSGKAIASLQVEAS 684
         . ...|||....   :|.  |:|  _   ::: :..|:|:|  .: ::||
  832 FDTAVTSASRTEMN...PRGNHKYARHS..DEGSGRPSEKGIEDFLLDAS 876

685 DLANFLTMDRNGG.YRGSQTLLRSVLSEKQELCFSVVSLLWQKLIASPEM 733
         ||)||||  ||  =|  |  |.|.|||||| ||.||.||:|||||||||:||||.||:
  877 DLANFLTADRLAGFYCGTQKLLRSVLAEKPELSFSVVSLLWHKLIAAPEI 926

734 QMSAESTSAHQGWRKVVDALCDIVSASPTKASAAIVLQAEKDLQPWIARD 783
         | -|||||||:||||-||||||::|||.|.||.||:|||||::||||||:|
  927 QPTAESTSAQQGWRQVVDALCNVVSATPAKAAAAVVLQAERELQPWIAKD 976

784 DEQGQKMWRVNQRIVKLIAELMRNHDSPEALVILASASDLLLRATDGMLV 833
         ||:|||||::|||||||:.|||||||-||.||||||||||||||||||||||
  977 DEEGQKMWKINQRIVKVLVELMRNHDRPESLVILASASDLLLRATDGMLV 1026

834 DGEACTLPQLELLEVTARAVHLIVEWGDSGVSVADGLSNLLKCRLSTTIR 883
         |||||||||||||-||||:: ::.||.||:.|.|||||||||||..|||
 1027 DGEACTLPQLELLEATARAIQPVLAWGPSGLAVVDGLSNLLKCRLPATIR 1076

884 CLSHPSAHVRALSMSVLRDILN..SGQINSSKLIQGEHRNGIQSPTYQCL 931
         ||||||||||||| ||||||:|  | .|. .. :....:||:.||.|. :
 1077 CLSHPSAHVRALSTSVLRDIMNQSSIPIKVTPKLPTTEKNGMNSPSYRFF 1126

932 AASIINWQADVERCIEWEAHSRRATGLTLAFL..TAAKELGCPLTC*Q 977
         .|. |:|-||::-|::|||||   .|.:.  .|| |||:||||.:.  |
 1127 NAASIDWKADIQNCLNWEAHSLLSTTMPTQFLDTAARELGCTISLSQ 1173
```

FIGURE 13B

```
MASSSSSERWIDGLQFSSLLWPPPRDPQQH    30
KDQVVAYVEYFGQFTSEQFPDDIAELVRHQ    60
YPSTEKRLLDDVLAMFVLHHPERGHAVILP    90
IISCLIDGSLVYSKEAHPFASFISLVCPSS   120
ENDYSEQWALACGEILRILTHYNRPIYKTE   150
QQNGDTERNCLSKATTSGSPTSEPKAGSPT   180
QHERKPLRPLSPWISDILLAAPLGIRSDYF   210
RWCSGVMGKYAAGELKPPTIESRGSGKHPQ   240
LMPSTPRWAVANGAGVILSVCDDEVARYET   270
ATLTAVAVPALLLPPPTTSLDEHLVAGLPA   300
LEPYARLFHRYYAIATPSATQRLLLGLLEA   330
PPSWAPDALDAAVQLVELLRAAEDYASGVR   360
LPRNWMHLHFLRAIGIAMSMRAGVAADAAA   390
ALLFRILSQPALLFPPLSQVEGVEIQHAPI   420
GGYSSNYRKQIEVPAAEATIEATAQGIASM   450
LCAHGPEVEWRICTIWEAAYGLIPLNSSAV   480
DLPEIIVATPLQPPILSWNLYIPLLKVLEY   510
LPRGSPSEACLMKIFVATVETILSRTFPPE   540
SSRELTRKARSSFTTRSATKNLAMSELRAM   570
VHALFLESCAGVELASRLLFVVLTVCVSHE   600
AQSSGSKRPKSEYASTTENIEANQPVSNNQ   630
TANRKSRNVKGQGPVAAFDSYVLAAVCALA   660
CEVQLYPMISGGGNFSNSAVAGTITKPVKI   690
NGSSKEYGAGIDSAISHTRRILAILEALFS   720
LKPSSVGTPWSYSSSEIVAAAMVAAHISEL   750
FRRSKALTHALSGLMRCKWDKEIHKRASSL   780
YNLIDVHSKVVASIVDKAEPLEAYLKNTPV   810
QKDSVTCLNWKQENTCASTTCFDTAVTSAS   840
RTEMNPRGNHKYARHSDEGSGRPSEKGIKD   870
FLLDASDLANFLTADRLAGFYCGTQKLLRS   900
VLAEKPELSPSVVSLLWHKLIAAPEIQPTA   930
ESTSAQQGWRQVVDALCNVVSATPAKAAAA   960
VVLQAERELQPWIAKDDEEGQKMWKINQRI   990
VKVLVELMRNHDRPESLVILASASDLLLRA  1020
TDGMLVDGEACTLPQLELLEATARAIQPVL  1050
AWGPSGLAVVDGLSNLLKCRLPATIRCLSH  1080
PSAHVRALSTSVLRDIMNQSSIPIKVTPKL  1110
PTTEKNGMNSPSYRFFNAASIDWKADIQNC  1140
LNWEAHSLLSTTMPTQFLDTAARELGCTIS  1170
LSQ*                            1173
```

FIGURE 14

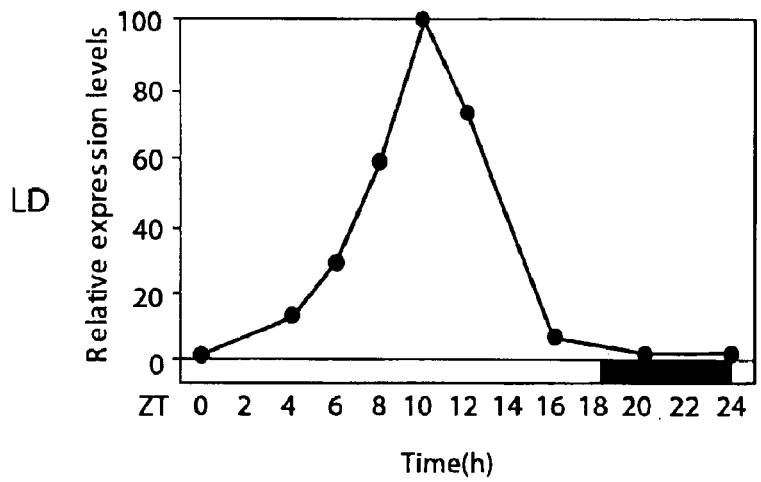
FIGURE 17A1
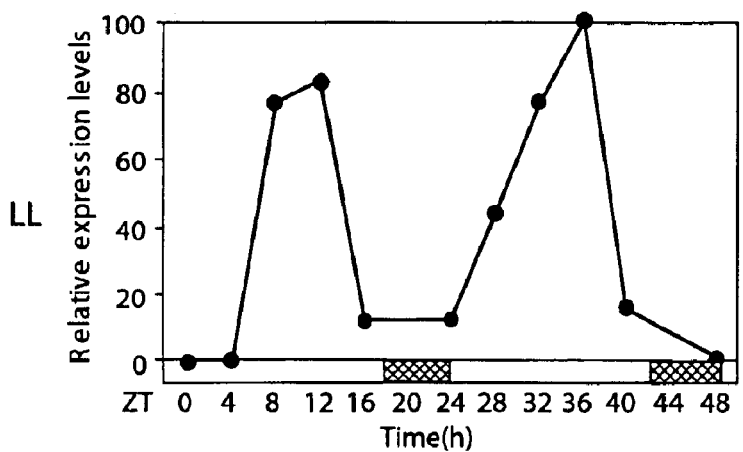
FIGURE 17A2
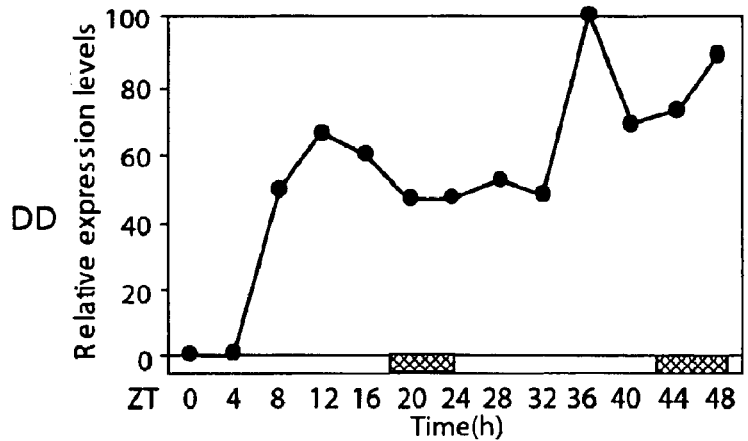
FIGURE 17A3

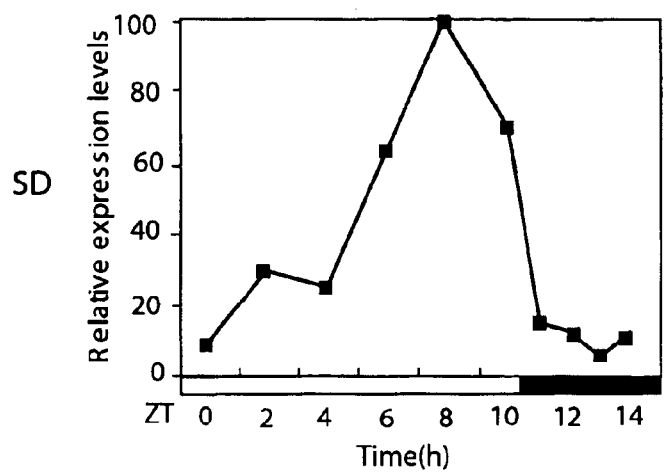
FIGURE 17B1
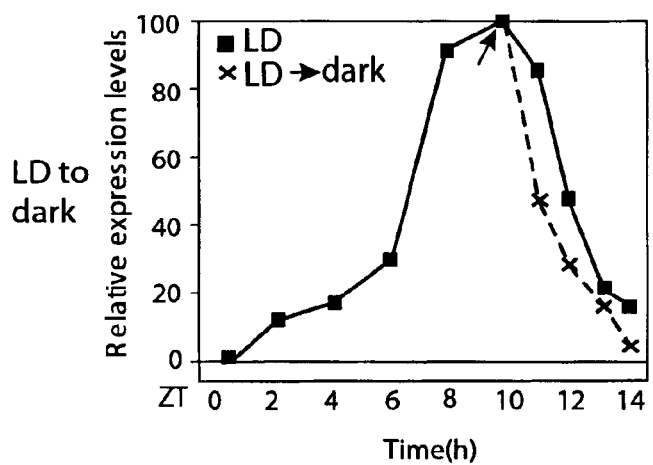
FIGURE 17B2
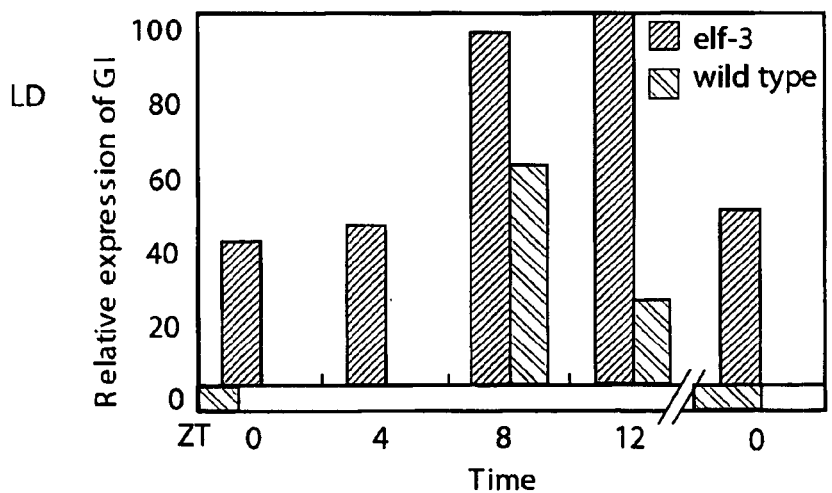
FIGURE 18A

US 6,887,708 B1

PLANT CONTROL GENES

The present application is a 371 U.S. National Phase of PCT/NZ99/00033, filed Mar. 19, 1999.

This invention relates to the genetic control of certain processes in plants and the cloning and expression of genes involved therein. More particularly, the invention relates to the cloning and expression of the GIGANTEA (GI) gene of *Arabidopsis thaliana*, to GI homologues from other species, and to manipulation and use of these GI genes in plants to control flowering and to direct starch accumulation in certain tissues.

BACKGROUND

Efficient flowering in plants is important, particularly when the intended product is the flower or the seed produced therefrom. One aspect of this is the timing of flowering: advancing or retarding the onset of flowering can be useful to farmers and seed producers. An understanding of the genetic mechanisms which influence flowering therefore provides a means for altering the flowering characteristics of the target plant.

Species for which flowering is important to crop production are numerous—essentially all crops which are grown from seed, with important examples being the cereals, rice and maize being probably the most agronomically important in warmer climatic zones, and wheat, barley, oats and rye in more temperate climates. Other important seed products are oil seed rape and canola, sugar beet, maize, sunflower, soyabean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

The so-called GIGANTEA or GI gene of *Arabidopsis thaliana* has been implicated in the response of that plant to photoperiod. However, the GI gene has not been conclusively identified or isolated to date, and its sequence has not been determined. Conclusive identification, isolation and sequencing of the GI gene would therefore be desirable to allow manipulation of the flowering process.

In addition to being able to manipulate flowering time, an ability to control starch accumulation in plants would also be useful.

Starch is synthesised by all higher plants and accumulates to high levels in most plants. Starch plays a crucial role in plant metabolism. It is synthesised in chloroplasts during photosynthesis and then degraded to supply energy for metabolism during the subsequent dark period. This causes fluctuations in starch levels, with the highest starch levels occurring at the end of the light period.

GI mutations cause starch to accumulate in the leaves GI starch accumulation follows wild type fluctuations, but has been shown to be two to three times higher than wild type plants. This accumulation is restricted to photosynthetically active tissues (Eimert et al. 1995).

Again, identification, isolation and sequencing of the GI gene would be desirable to allow manipulation of the starch accumulation process.

It is therefore the object of this invention to go some distance towards meeting the above desiderata, or at least to provide the public with a useful choice.

SUMMARY OF THE INVENTION

The invention has a number of aspects, and specifically contemplates the following:

a nucleic acid isolate comprising a nucleotide sequence encoding a polypeptide with GI function;

nucleic acid as described above wherein said nucleotide sequence is that of the GI gene of *Arabidopsis thaliana* or a GI homologue from another plant species, or a mutant, derivative or allele of the gene or homologue;

nucleic acid as described above wherein said GI nucleotide sequence includes the nucleotides shown in FIG. 4A or 4B;

nucleic acid as described above which comprises or includes the nucleotide sequence shown in FIG. 5, FIG. 8 or FIG. 11;

nucleic acid as described above which encodes the all or part of the amino acid sequence of FIG. 6, FIG. 9 or FIG. 12;

nucleic acid as described above wherein expression of said nucleotide sequence delays flowering in a transgenic plant;

nucleic acid as described above wherein expression of said nucleotide sequence promotes flowering in a transgenic plant;

nucleic acid as described above wherein expression of said nucleotide sequence promotes starch accumulation in the photosynthetically active tissues of a transgenic plant;

a nucleic acid isolate comprising a nucleotide sequence complementary to a coding sequence as described above or a fragment of a said coding sequence;

nucleic acid as described above further comprising a regulatory sequence for sense transcription of said polypeptide;

nucleic acid which is DNA as described above wherein said nucleotide sequence or a fragment thereof is under control of a regulatory sequence for anti-sense transcription of said nucleotide sequence or a fragment thereof;

a nucleic acid vector suitable for transformation of a plant cell and comprising nucleic acid as described above;

a plant cell comprising nucleic acid as described above;

a plant comprising plant cells as described above;

selfed or hybrid progeny or a descendant of a plant as described above, or any part or propagule of such a plant, progeny or descendant, such as seed;

a method of influencing a flowering characteristic of a plant, the method comprising causing or allowing expression of the polypeptide encoded by nucleic acid as described above within cells of the plant;

a method of influencing a flowering characteristic of a plant, the method comprising causing or allowing transcription from nucleic acid as described above within cells of the plant;

a method of influencing a flowering characteristic of a plant, the method comprising causing or allowing anti-sense transcription from nucleic acid as described above within cells of the plant;

a method of promoting starch accumulation in the photosynthetically-active tissues of a transgenic plant, the method comprising causing or allowing expression of the polypeptide encoded by nucleic acid as described above within the plant;

a method of promoting starch accumulation in the photosynthetically-active tissues of a transgenic plant, the method comprising causing or allowing transcription from nucleic acid as described above within the plant;

a method of promoting starch accumulation in the photosynthetically-active tissues of a transgenic plant, the method comprising causing or allowing anti-sense transcription from nucleic acid as described above within cells of the plant;

a method of identifying and cloning GI homologues from plant species other than *Arabidopsis thaliana* which method employs a nucleotide sequence derived from that shown in FIGS. 4A, 4B, 5 or 8; and nucleic acid encoding a GI homologue obtained as described above.

DESCRIPTION OF THE DRAWINGS

In the Figures:

FIG. 1 compares an inverse polymerase chain reaction (IPCR) fragment with clone Y12227. The top line represents the sequence from the IPCR fragment, [SEQ ID NO: 39] and the bottom line represents the sequence from clone Y12227 [SEQ ID NO:43].

FIG. 4 gives the nucleotide sequence of the ends of cDNA1, with FIG. 4A representing the 5' end sequence (SEQ ID NO:1) and FIG. 4B representing the 3' end sequence (SEQ ID NO:2). Position 1 of the 5' end sequence corresponds to nucleotide 18311 of Y12227 and amino acid 637 of gene 5. Position 1 of the 3' end sequence corresponds to nucleotide 20312 of Y12227.

FIGS. 5A and 5B show a nucleic acid sequence (SEQ ID NO:3) encoding one polypeptide with GI function (from *Arabidopsis*).

FIG. 6 is the amino acid sequence (SEQ ID NO:4) of the expressed GI protein encoded by the sequence of FIG. 5 (SEQ ID NO: 3).

FIGS. 8A, 8B and 8C show a further nucleic acid sequence (SEQ ID NO:5) encoding a polypeptide with GI function, (also from *Arabidopsis*).

FIGS. 9A and 9B show the amino acid sequence (SEQ ID NO:6) of the polypeptide encoded by the sequence of FIG. 8 (SEQ ID NO: 5).

FIG. 10 shows the results of homology analyses between the predicted GI sequence of FIG. 5 (SEQ ID NO: 3) and three rice EST's, EST C73052 (SEQ ID NO: 40), EST C72988 (SEQ ID NO: 41), and EST D40642 (SEQ ID NO: 42).

FIG. 11A and 11B give the nucleotide sequence (SEQ ID NO:7) encoding part of a further polypeptide having GI function (from rice).

FIG. 12 gives the amino acid sequence (SEQ ID NO:8) corresponding to the sequence of FIG. 11 (SEQ ID NO: 7).

FIG. 13A and 13B show a line up between portions of an amino acid sequence of a polypeptide having GI function, as between those encoded by *Arabidopsis* and rice GI cDNA's, (SEQ ID NO: 5) and (SEQ ID NO: 7), respectively.

FIG. 14. The predicted amino acid sequence of the GI protein (SEQ ID NO:9). Putative transmembrane domains predicted in the protein by membrane topology prediction programs are underlined.

FIGS. 17A1, 17A2, 17A3, 17B1 and 17B2 show the northern hybridisation analysis of GI expression in different light regimes. Plants were grown in LD or SD conditions until the six leaf stage. Total RNA (10 $\mu$g), was extracted from aerial parts harvested at the times shown and analysed by northern hybridisation using a GI cDNA probe. Results are presented as a proportion of the highest value after normalisation with respect to 25/26s rRNA levels. Horizontal bars under each graph represent the light (white) and dark (black) conditions provided. ZT 0 hr is at lights on. Hatched bars represent subjective night experienced in continuous light (LL) and continuous dark (DD) conditions. FIGS. 17A1, 17A2 and 17A3. Timecourse of GI expression in plants grown in LD (top), LL (middle) and DD (bottom). For the LL and DD experiments, plants were entrained in LD and shifted to LL or DD 24 hours before tissue harvesting was initiated at ZT 0. FIGS. 17B1 and 17B2. Effect of SD and the transition to darkness on GI expression. Plants were grown in SD (top) or LD (bottom). At ZT 10, indicated by the arrow, half of the LD plants were shifted to darkness.

FIGS. 18A, 18B and 18C show the expression of GI in elf3 mutants in LD, SD and LL. elf3 mutant plants were grown in LD or SD conditions until the six leaf stage. Total RNA (10 $\mu$g) was extracted from aerial parts and analysed by northern hybridisation using a GI cDNA probe. Results are presented as a proportion of the highest value after normalisation with respect to 25/26s rRNA levels. Horizontal bars under each graph represent the light (white) and dark (black) conditions provided. ZT 0 hr is at lights on. A. Timecourse of GI expression in LD. B. Timecourse of GI expression in SD. C. Timecourse of GI expression in LL.

DESCRIPTION OF THE INVENTION

Figure 2:
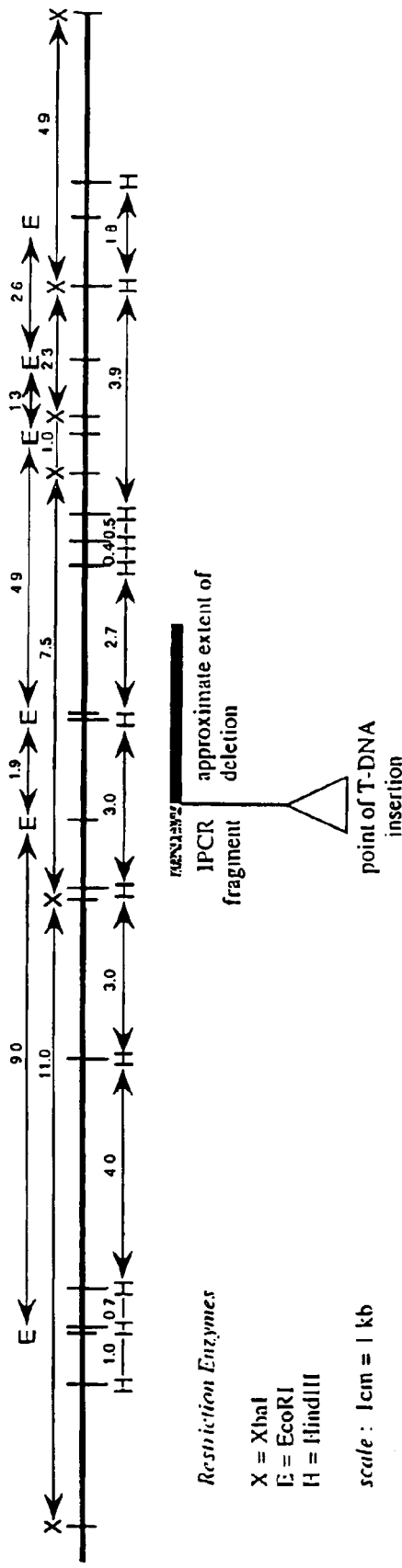
FIG. 2 is a map of the T-DNA insertion site.

As described above, the primary focus of the invention is on the GI gene. By "GI gene" as used herein is meant a nucleic acid molecule comprising a nucleotide sequence encoding a polypeptide with GI function.

A partial nucleic acid sequence for a specific GI gene according to the invention is shown in each of FIGS. 4A and 4B.

A nucleic acid (cDNA) sequence for an *Arabidopsis* GI gene is shown in FIG. 5. The predicted amino acid sequence of the encoded polypeptide, which has GI function, is shown in FIG. 6.

Similarly, FIG. 8 sets out the nucleic acid (cDNA) sequence encoding another polypeptide having GI function, whereas FIG. 9 gives the predicted amino acid sequence of that polypeptide.

Analysis of a full length GI cDNA (4077 bp) related to FIG. 8 revealed that GI has a coding region of 3522 bp with a 5' untranslated region of 318 bp and 217 bp of 3' untranslated region. The full length GI cDNA is predicted to encode a 1173 amino acid protein of 127 Kd FIG. 9).

Web-based membrane topology prediction programmes (Top Pred 2, Von Heijne 1992; PSORT and PSORT2, Nakai and Kanehisa, 1992) predict that the GI polypeptide contains at least four transmembrane domains indicating that it is likely to be a membrane protein.

Variants or homologues of the above sequences also form part of the present invention. Polynucleotide or polypeptide sequences may be aligned, and percentage of identical nucleotides in a specified region may be determined against another sequence, using computer algorithms that are publicly available. Two exemplary algorithms for aligning and identifying the similarity of polynucleotide sequences are the BLASTN and FASTA algorithms. The similarity of polypeptide sequences may be examined using the BLASTP algorithm. Both the BLASTN and BLASTP software are available on the NCBI anonymous FTP server (ncbi.nlm.nih.gov) under \blast\executables\. The BLASTN algorithm version 2.0.4 [Feb. 24, 1998], set to the default parameters described in the documentation and distributed with the algorithm, is preferred for use in the determination of variants according to the present invention. The use of the BLAST family of algorithms, including BLASTN and BLASTP, is described at NCBI's website at URL ncbi.nlm.nih.gov/BLAST/newblast and in the publication of Altschul, Stephen F, et al (1997). "Gapped BLAST and PSI-BLAST: a new generation of protein database search programs", *Nucleic Acids Res.* 25:3389–3402. The computer algorithm FASTA is available on the Internet at the ftp site virginia.edu.pub\fasta\. Version 2.0u4, February 1996, set to the default parameters described in the documentation and distributed with the algorithm, is preferred for use in the determination of variants according to the present invention. The use of the FASTA algorithm is described in the W R Pearson and D. J. Lipman, "Improved Tools for Biological Sequence Analysis," *Proc. Natl. Acad. Sci. USA* 85:2444–2448 (1988) and W. R. Pearson, "Rapid and Sensitive Sequence Comparison with FASTP and FASTA," *Methods in Enzymology* 183:63–98 (1990).

The following running parameters are preferred for determination of alignments and similarities using BLASTN that contribute to E values (as discussed below) and percentage identity: Unix running command: blastall -p blastn -d embldb -e 10-G 1-E 1-r 2-v 50-b 50-1 queryseq -o results; and parameter default values:

-i queryseq -o results; and parameter default values:
-p Program Name [String]
-e Expectation value (E) [Real]
-G Cost to open a gap (zero invokes default behaviour) [Integer]
-E Cost to extend a gap (zero invokes default behaviour) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional
For BLASTP the following running parameters are preferred: blastall -p blastp -d swissprotdb -e 10-G 1-E 1-v 50-b 50-I queryseq -o results
-p Program Name [String]
-d Database [String]
-e Expectation value (E) [Real]
-G Cost to open a gap (zero invokes a default behaviour) [Integer]
-E Cost to extend a gap (zero invokes a default behaviour) [Integer]
-v Number of one-line descriptions (v) [Integer]
-b Number of alignments to show (b) [Integer]
-I Query File [File In]
-o BLAST report Output File [File Out] Optional Homology may be at the nucleotide sequence and/or encoded amino acid sequence level. Preferably, the nucleic acid and/or amino acid sequence shares at least about 60%, or 70%, or 80% homology, most preferably at least about 90%, 95%, 96%, 97%, 98% or 99% homology.

Homology may be over the full-length of the relevant sequence shown herein, or may be over a part of it, preferably over a contiguous sequence of about or greater than about 20, 25, 30, 33, 40, 50, 67, 133, 167, 200, 233, 267, 300, 333, 400 or more amino acids or codons, compared with FIGS. 6 and 9, or 5 and 10, respectively.

A GI homologue (or orthologue) from rice has also been identified. The partial cDNA sequence (EST) for this orthologue is given in FIG. 11, whereas the predicted amino acid sequence is given in FIG. 12. A line up of the relevant domains of the respective nucleotide sequences as between FIGS. 8 and 11 is given in FIG. 13, showing 78.35% similarity and 67.83% identity.

A variant polypeptide in accordance with the present invention may include within the sequence shown in FIG. 6, FIG. 9 or FIG. 12, a single amino acid or 2, 3, 4, 5, 6, 7, 8, or 9 changes, about 10, 15, 20, 30, 40 or 50 changes, or greater than about 50, 60, 70, 80 or 90 changes. In addition, to one or more changes within the amino acid sequence shown, a variant polypeptide may include additional amino acids at the C-terminus and/or N-terminus. Naturally, changes to the nucleic acid which make no difference to the encoded polypeptide (ie. "degeneratively equivalent") are not included.

The activity of a variant polypeptide may be assessed by transformation into a host cell capable of expressing the nucleic acid of the invention. Methodology for such transformation is described in more detail below.

In a further aspect of the invention there is disclosed a method of producing a derivative nucleic acid comprising the step of modifying any of the sequences disclosed above, particularly the sequences of FIG. 5, FIG. 8 or FIG. 11.

Changes may be desirable for a number of reasons. For instance they may introduce or remove restriction endonuclease sites or alter codon usage.

Alternatively changes to a sequence may produce a derivative by way of one or more of addition, insertion, deletion or substitution of one or more nucleotides in the nucleic acid, leading to the addition, insertion, deletion or substitution of one or more amino acids in the encoded polypeptide.

Such changes may modify sites which are required for post translation modification such as cleavage sites in the encoded polypeptide; motifs in the encoded polypeptide for glycosylation, lipoylation, etc. Leader or other targeting sequences (eg. membrane or golgi locating sequences) may be added to the expressed protein to determine its location following expression.

Other desirable mutation may be random or site directed mutagenesis in order to alter the activity (eg. specificity) or stability of the encoded polypeptide. Changes may be by way of conservative variation, ie. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the sidechain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide eg. altered stability or specificity.

In a further aspect of the present invention there is provided a method of identifying and/or cloning a nucleic acid variant from a plant which method employs a GI sequence described above.

In one embodiment, nucleotide sequence information provided herein may be used in a database (eg. of EST's or STS's) search to find homologous sequences, such as those which may become available in due course, and expression products of which can be tested for activity as described below.

In another embodiment the nucleotide sequence information provided herein may be used to design probes and primers for probing or amplification of GI or variants thereof. An oligonucleotide for use in probing or PCR may be about 30 or fewer nucleotides in length (eg. 18, 21 or 24). Generally specific primers are upwards of 14 nucleotides in length. For optimum specificity and cost effectiveness, primers of 16–24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length. Naturally sequences may be based on FIG. 5, FIG. 8 or FIG. 11, or the complement thereof. Small variations may be introduced into the sequence to produce "consensus" or "degenerate" primers if required.

Such probes and primers also form one aspect of the present invention.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27–31, for a review).

In one embodiment, a variant in accordance with the present invention is obtainable by means of a method which includes:

(a) providing a preparation of nucleic acid, eg from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (eg promoters etc) as described hereinafter, (b) providing a probe or primer as discussed above, (c) containing nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (eg DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridisations identified as positive which can be investigated further.

For example, hybridisations may be performed, according to the method of Sambrook et al. (below) using a hybridisation solution comprising: 5×SSC (wherein 'SSC' =1.15 M sodium chloride; 0.15 M sodium citrate; pH 7), 5× Denhardt's reagent, 0.5–10% SDS, 100 μg/ml denatured, fragmented salmon sperm DNA, 0.05% sodium pyrophosphate and up to 50% formamide. Hybridisation is carried out at 37–42° C. for at least six hours. Following hybridisation, filters are washed as follow: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridisation between nucleic acid molecules of a specified sequence homology is (Sambrook et al., 1989): $T_m$=8.15° C.+16.6 Log [Na+]+0.41 (% G+C)–0.63 (% formamide)–600/#bp in duplex.

As an illustration of the above formula, using [Na+]= [0.368] and 50-% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridisation temperature of 42° C. Such a sequence would be considered substantially homologous to the nucleic acid sequence of the present invention.

It is well known in the art to increase stringency of hybridisation gradually until only a few positive clones remain. Other suitable conditions include hybridising at 65° C. in 10% dextran sulphate, 1% SDS, 1 M NaCl, 50 μg/ml denatured salmon sperm DNA followed by two rinses in 2×SSC at room temperature then washing at 65° C. in 1×SSC, 0.1% SDS for medium stringency or 0.1×SSC, 0.1% SDS for high stringency.

In a further embodiment, hybridisation of nucleic acid molecule to a variant may be determined or identified indirectly, eg using a nucleic acid amplification reaction, particularly the polymerase chain reaction (PCR). PCR requires the use of two primers to specifically amplify target nucleic acid, so preferably two nucleic acid molecules with characteristic sequences are employed. Using RACE PCR, only one such primer may be needed (see "PCR protocols; A Guide to Methods and Applications", Eds. Innis et al, Academic Press, New York, (1990)).

The present invention also contemplates a vector which comprises nucleic acid with any one of the provided sequences, preferably a vector from which polypeptide (or at least the functional portion thereof encoded by the nucleic acid sequence can be expressed. The vector is preferably suitable for transformation into a plant cell. The invention further encompasses a host cell transformed with such a vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A vector comprising nucleic acid according to the present invention need not include a promoter or other regulatory sequence, particularly if the vector is to be used to introduce the nucleic acid into cells for recombination into the genome.

Nucleic acid molecules and vectors according to the present invention may be provided isolated from their natural environment, in substantially pure or homogenous form.

Nucleic acid may of course be double- or single-stranded, cDNA or genomic DNA, RNA, wholly or partially synthetic, as appropriate. Synthesis can be automated using equipment such as is commercially available from suppliers such as Perkin Elmer/Applied Biosystems Division (Foster City, Calif., USA) following manufacturers instructions.

The present invention also encompasses methods of making the polypeptide of the invention having GI function by expression from encoding nucleic acid therefor under suitable conditions in suitable host cells. Those skilled in the art are well able to construct vectors and design protocols for expression and recovery of products of recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual: 2<sup>nd</sup>* edition, Sambrook et al. 1989, Cold Spring Harbor Laboratory Press. Regulatory sequences which are endogenous to the target plant are preferred.

Transformation procedures depend on the host used, but are well known.

Also according to the invention there is provided a plant cell having incorporated into its genome a sequence of nucleotides as provided by the present invention, under operative control of a regulatory sequence for control of expression. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

Techniques for stably incorporating vectors into the genome of target cells are well known in the art and include *Agrobacterium tumefaciens* mediated introduction, electroporation, protoplast fusion, injection into reproductive organs, injection into immature embryos, high velocity projectile introduction and the like.

Plants which comprise a plant cell according to the invention are also provided, along with any part or propagule thereof, seed, selfed or hybrid progeny and descendants.

The invention further provides a method of influencing the flowering characteristics of a plant comprising expression of a heterologous GI gene sequence (or mutant, allele, derivative or homologue thereof, as discussed) within cells of the plant. The term "heterologous" indicates that the gene/sequence of nucleotides in question has been introduced into cells of the plant using genetic engineering, ie by human intervention. The gene may be on an extra-genomic vector or incorporated, preferably stably, into the genome. The heterologous gene may replace an endogenous equivalent gene, ic one which normally performs the same or a similar function in control of flowering, or the inserted sequence may be additional to the endogenous gene. An advantage of introduction of a heterologous gene is the ability to place expression of the gene under the control of a promoter of choice, in order to be able to influence gene expression, and therefore flowering, according to preference. Furthermore, mutants and derivatives of the wild-type gene, eg with higher or lower activity than wild-type, may be used in plant of the endogenous gene.

The principal flowering characteristic which may be altered using the present invention is the timing of flowering. Under-expression of the gene product of the GI gene leads to delayed flowering (as suggested by the gi mutant phenotype); over-expression may lead to precocious flowering. This degree of control is useful to ensure synchronous flowering of male and female parent lines in hybrid production, for example. Another use is to advance or retard the flowering in accordance with the dictates of the climate so as to extend or reduce the growing season. This may involve use of anti-sense or sense regulation.

The nucleic acid according to the invention, such as a GI gene or homologue, may be placed under the control of an externally inducible gene promoter to place the timing of flowering under the control of the user. This is advantageous in that flower production, and subsequent events such as seed set, may be timed to meet market demands, for example, in cut flowers or decorative flowering pot plants. Delaying flowering in pot plants is advantageous to lengthen the period available for transport of the product from the producer to the point of sale and lengthening of the flowering period is an obvious advantage to the purchaser.

The term "inducible" as applied to a promoter is well understood by those skilled in the art. In essence, expression under the control of an inducible promoter is switched on or increased in response to an applied stimulus. The nature of the stimulus various between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b); the maize glutathione-S-transferase isoform II (GST-II-27) gene promoter which is activated in response to application of exogenous safener (WO 93/01294, ICI Ltd); the cauliflower meri 5 promoter that is expressed in the vegetable apical meristem as well as several well localised positions in the plant body, eg inner phloem, flower primordia, branching points in root and shoot (Medford, 1992; Medford et al. 1991) and the *Arabidopsis thaliana* LEAFY promoter that is expressed very early in flower development (Weigel et al. 1992).

When introducing a chosen gene construct into a cell, certain considerations must be-taken-into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with a DNA molecule containing the sequence may be produced by standard techniques for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966), electroporation (EP 290395, WO 87/06614) or other forms of direct DNA uptake (DE 4005152, WO 90/12096, U.S. Pat. No. 4,684,611). *Agrobacterium* transformation is widely used by those skilled in the art to transform dicotyledonous species. Although *Agrobacterium* has been reported to be able to transform foreign DNA into some monocotyledonous species (WO 92/14828), microprojectible bombardment, electroporation and direct DNA uptake are preferred where *Agrobacterium* is ineffecicient or ineffective. Alternatively, a combination of different techniques may be employed to enhance the efficiency of the transformation process, eg. bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

In the present invention, over-expression may be achieved by introduction of the nucleotide sequence in a sense orientation. Thus, the present invention provides method of influencing a flowering characteristic of a plant, the method comprising causing or allowing expression of the polypeptide encoded by the nucleotide sequence of nucleic acid according to the invention from that nucleic acid within cells of the plant.

Under-expression of the gene product polypeptide may be achieved using anti-sense technology or "sense regulation". The use of anti-sense genes or partial gene sequences to down-regulate gene expression is now well-established. DNA is placed under the control of a promoter such that transcription of the "anti-sense" strand of the DNA yields RNA which is complementary to normal mRNA transcribed from the "sense" strand of the target gene. For double-stranded DNA this is achieved by placing a coding sequence or a fragment thereof in a "reverse orientation" under the control of a promoter. The complementary anti-sense RNA sequence is thought then to bind with mRNA to form a duplex, inhibiting translation of the endogenous mRNA from the target gene into protein. (See, for example, Rothstein et al. 1987; Smith et al. 1988; Zhang et al. 1992).

Thus, the present invention also provides a method of influencing a flowering characteristic of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. (See for example, van der Krol 1990; Napoli et al. 1990; Zhang et al. 1992).

Thus, the present invention also provides a method of influencing a flowering characteristic of a plant, the method comprising causing or allowing expression from nucleic acid according to the invention within cells of the plant. This may be used to suppress activity of a polypeptide with ability to influence a flowering characteristic. Here the activity of the polypeptide is preferably suppressed as a result of under-expression within the plant cells.

As stated above, the expression pattern of the GI gene may be altered by fusing it to a foreign promoter. For example, International patent application WO 93/01294 of Imperial Chemical Industries Limited describes a chemically inducible gene promoter sequence isolated from a 27 kD subunit of the maize glutathione-S-transferase, isoform II gene (GST-II-27). It has been found that when linked to an exogenous gene and introduced into a plant by transformation, the GST-II-27 promoter provides a means for the external regulation of the expression of that exogenous gene.

The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugerbeet, cotton; cereals such as wheat, barley, rice, maize, sorghum; fruit such as tomatoes, mangoes, peaches, apples, pears, strawberries, bananas and melons; and vegetables such as carrots, lettuce, cabbage and onion. The GST-II-27 promoter is also suitable for use in a variety of tissues, including roots, leaves, stems and reproductive tissues.

Accordingly, the present invention contemplates in a further aspect a gene construct comprising an inducible promoter operatively linked to a nucleotide sequence provided by the present invention, such as the GI gene of *Arabidopsis thaliana*, a homologous gene from another plant species or any variant thereof. This enables control of expression of the gene. The invention also provides plants transformed with said gene construct and methods comprising introduction of such a construct into a plant cell and/or induction of expression of a construct within a plant cell, by application of a suitable stimulus, an effective exogenous inducer. The promoter may be the GST-II-27 gene promoter or any other inducible plant promoter.

Aspects and embodiments of the present invention will now be illustrated, by way of example, with reference to the experimental section. Further aspects and embodiments will be apparent to those skilled in the art. AU documents mentioned in this text are incorporated herein by reference.

EXPERIMENTAL

Part A

Plant Material and Plant Growth Conditions

*Arabidopsis* ecotypes Wassilewslija (Ws), C24 and Landsberg erecta (Ler) were obtained from Lehle Seeds (Round Rock, Tex.). Seeds of gi mutant alleles (gi-1-6) were obtained from the *Arabidopsis* Biological Resource Centre at Ohio University. Seed was cold treated before sowing by placing on wet filter paper at 4° C. for 2–4 days. Seed was sown on a peat:sand growth media or soil, and plants were grown at ~22° C. in the greenhouse (12–16 h light/8–12 h dark). Light extensions were provided as required with mercury vapour growth lamps (Sylvania). Seedlings grown in vitro were cultured at 22° C. in the presence of cool white fluorescent light (16 h light 8 h dark).

Bacterial Strains and Plasmids

The *Agrobacterium* strain GV3101 containing pMP90RK (Koncz and Schell 1986) was used for all plant transformations. The binary vector, pGKB5 (Bouchez et al. 1993), was used for T-DNA tagging experiments. The T-DNA of this vector contains the bar plant selectable-marker gene that confers resistance to the herbicide Basta, and the nptII gene that confers resistance to the antibiotic kanamycin. The T-DNA also carries a GUS reporter gene close to the right T-DNA border for plant promoter trapping. The pGKB5 DNA sequence is available at the internet address nasc.nott.ac.uk:8300/Vol2ii/bouchez.html.

Vacuum Infiltration Transformation

Plasmids were transferred to *Agrobacterium tumefaciens* GV3101 by freeze-thaw transformation (Holsters et al. 1978). *Agrobacterium* transconjugants were selected on YM media Vincent 1985) supplemented with rifampicin, kanamycin (both 50 mg L$^{-1}$), and gentamycin (25 mg L$^{-1}$).

The *Agrobacterium* solution was prepared for vacuum infiltration as described by Bechtold et al. (1993). Overnight *Agrobacterium* cultures were inoculated into LB or YN broth supplemented with the appropriate antibiotics. Three liter cultures were grown overnight to OD$_{600}$=0.8, harvested by centrifugation and resuspended in 1 L of infiltration solution consisting of MS salts with 5% sucrose w/v and 10 $\mu$L$^{-1}$ benzylaminopurine. Silwet L-77 (Lehle Seeds) was added to the infiltration solution at 0.005% v/v where specified. Silwet L-77 is an organosilicane compound (polyalkleneoxide modified heptamethyltrisiloxane) with low phytotoxicity.

*Arabidopsis* transformation was carried out essentially as described by Bechtold et al. (1993) using healthy flowering plants (3–5 weeks old). At this stage, the first siliques were beginning to develop on the primary inflorescence. Twenty to forty plants were uprooted and submerged in 300–500 mL of *Agrobacterium* solution in a 10 L desiccation vessel. Plants were infiltrated for 20 min in a vacuum of 686 mm Hg (using a Javac DSL-150 direct drive, single stage, high vacuum pump), with occasional swirling of the boiling *Agrobacterium*. The vacuum was released slowly over 2–4 min. The plants were repotted and placed in a greenhouse. Plants were covered with plastic for the first 3 days after infiltration to prevent desiccation. Plants were allowed to self fertilise and the resulting T1 seed was collected in bulk from dried siliques.

Selection of Transformant Plants

Screening for transformants was performed in the greenhouse by sowing 200 mg (~10,000) T1 seed on a 320×235 mm perlite base overlaid with sand, and sub-irrigating with 10 mg L$^{-1}$ ammonium glufosinate in the form of Basta herbicide (BASF, 200 mg L$^{-1}$ ammonium glufosinate).

After 10–14 days of selection, transformant plants were transplanted to a peat:sand growth media and grown to maturity in the greenhouse. Transformants were allowed to self fertilise, and T2 seed was collected individually from each T1 plant.

Mutant Screening and Analysis

T2 seed (100–400) of transformant lines was cold treated for 3 days on moist filter paper at 4° C. and sown out in the greenhouse. Plants were screened by eye for late-flowering phenotypes. Flowering time was measured by days to flowering and by counting the number of rosette leaves at flowering (Koornneef et al. 1991). In a screen of 800 transformant lines a transformant was identified that flowered approximately two weeks later than wild-type.

Linkage Analysis by the Kanamycin Resistance Assay

The late-flowering mutant was back-crossed to wild type and mutants from the F2 generation of this cross were tested for linkage between the T-DNA insert and the mutation. Seeds (200–400) were surface sterilized and placed on GM medium agar plates containing 100 mg L$^{-1}$ kanamycin. After 14 days, the seedlings were scored for kanamycin resistance. The ratio of resistant to sensitive seedlings was used to determine whether the parent plant was heterozgous or homozygous for the T-DNA insertion according to Mendelian principles. Linkage tests indicated that the gi gene was likely to be tagged with the T-DNA tag as no recombination events between the T-DNA and the mutation were seen in 120 chromosomes.

Allelism tests

The late-flowering mutant was crossed with 12 *Arabidopsis* late-flowering mutants (ft-1, fve-1, fd-1, fca-1, fpa-1, fy-1; fha-1, fwa-1, fe-1, constans-1, gigantea-3, and luminidependens-3. The flowering-time of the F1 progeny plants from each cross, the flowering-time mutants and wild type ecotypes were then compared. The F1 progeny of the cross to gi-3 flowered late, indicating that the late flowering T-DNA mutant was an allele of the GIGANTEA gene (gi). This was named gi-TDNA.

Inverse Polymerase Chain Reaction (IPCR)

Plant DNA flanking the left border of the T-DNA insertion was isolated by IPCR as described by Long et al. (1993). *Arabidopsis* genomic DNA prepared according to the method of Doyle and Doyle (1990) was digested with a selection of restriction endonucleases. The digested DNA was then ligated and used as the template for IPCR as follows.

IPCR was performed using nested primers (consisting of an external pair; gkb8-5'AGC TGGTAC ATT GCC GTA G3' (SEQ ID NO:10) and gkb9-5'TTT TTG CTT GGA CTA TAA TAC C3' (SEQ ID NO:11) and an internal pair; gkb7-5'TAG ATG AAA GAC TGA GTG CGA T3' (SEQ ID NO:12) and gkb10-5'CTA CM ATT GCC TTT TCT TAT C3' (SEQ ID NO:13);) which contained sequences from the left border of the pGKB5 T-DNA. A 1.4 kilobase IPCR fragment was isolated that contained T-DNA left border sequences and flanking *Arabidopsis* sequences.

The IPCR fragment was found to be identical to *Arabidopsis* genomic sequence which had been sequenced as part of the European Union programme of European Scientist Sequencing *Arabidopsis* (ESSA) (Genbank accession Y12227; Terryn et al 1997) (FIG. 1).

Clone Isolation and Analysis

Figure 3:
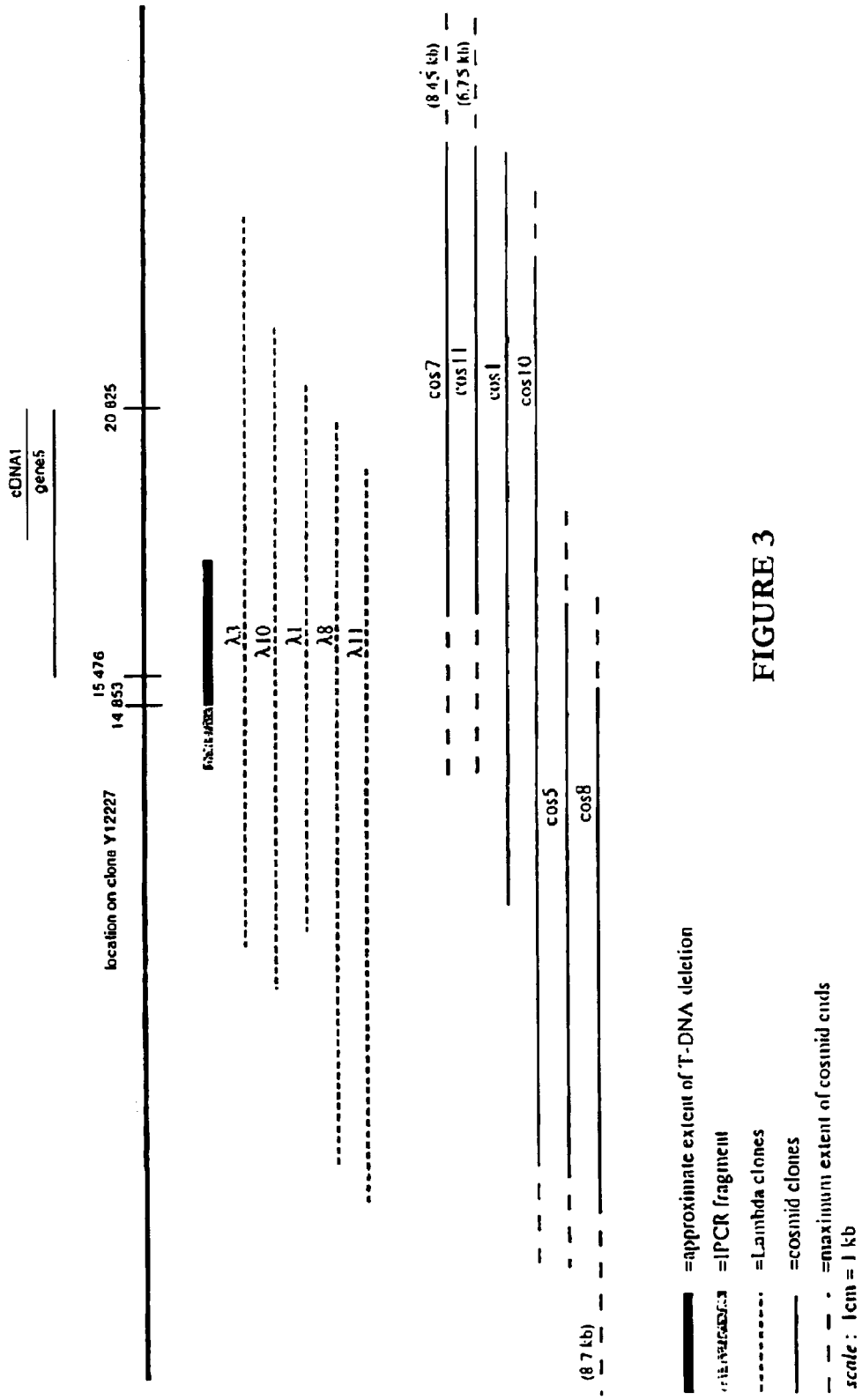
FIG. 3 is a map of the contig and position of cDNA.

The IPCR fragment was used to screen 20,000 clones from an *Arabidopsis* genomic library in λFIX. Five overlapping clones were isolated and restriction mapped. Southern hybridization analysis (Southern, 1975) using fragments from these lambda clones as a probe against wild type and gi-TDNA mutant DNA showed that the T-DNA insertion had caused a deletion of approximately 3 kilobases upon insertion (FIG. 2), with the deletion starting at base 14853 on clone Y12227. Fragments of these clones were used to probe 40,000 clones from a transformation competent cosmid library constructed from lhy mutant DNA (Schaffer, 1997). Eight overlapping cosmid clones were isolated and also restriction mapped. A cosmid contig spanning the region was constructed (FIG. 3). Cosmd 1.1 (~15 kb) was shown to span the entire genomic region affected by the T-DNA insertion. The conclusion was that cosmid 1.1 contains the GI gene.

A 7.5 kb XbaI fragment of cosmid 1.1 which spanned the region of the T-DNA insertion was used to screen 540,000 clones from the λPRL-2 cDNA library (Obtained from ABRC, Ohio State University, USA). Three identical cDNAs were isolated and sequenced from both ends using the the dideoxynucleotide chain terminator method (Sanger et al. 1977). Databases were searched for homology to the cDNA sequences using the University of Wisconsin Genetics Computer Group (GCG) programmes and BLAST (Altschul et al. 1990).

The 5' and 3' end sequences from the longest cDNA clone, (cDNA1) are shown in FIG. 4 (SEQ ID NO: 1) and (SEQ ID NO: 2), respectively.

cDNA1 was found to be a truncated cDNA of the predicted gene 5 from the genomic clone (FIG. 5) (Genbank accession Y12227; Terryn et al 1997) (SEQ ID NO: 3). The position of cDNA1 on predicted gene 5 protein is shown in FIG. 3. Seven genes are predicted in the 24 kb sequence of clone Y12227. The deletion in gi-TDNA specifically deletes part of the predicted gene 5 (FIG. 3). The position of cDNA 1 on the predicted gene 5 protein is shown (FIG. 3).

It was therefore concluded that gene 5 is likely to be the GI gene and to encode a GI protein having the amino acid sequence shown in FIG. 6 (SEQ ID NO: 4). However, it is to be emphasised that this conclusion was not and could not be drawn from the bare sequence information. No association or linkage was drawn by Terryn et al between gene 5 and flowering timing and/or starch accumulation. Further, the sequence was merely predicted to be a gene—it was neither isolated to confirm this nor expressed to identify an encoded protein product.

Confirmatory Mapping Studies

In order to map the position of the GI gene relative to RFLP markers, a gi mutant in the Landsberg erecta ecotype was crossed to wild-type Columbia. The F1 plants were self-fertilised and the F2 generation sown out. DNA was extracted from 800 late-flowering F2 plants that were presumed to be homozygous for the gi mutation.

The work of Araki and Komeda had previously shown that GI mapped to chromosome 1 close to the RFLP marker m235 (Araki and Komeda 1993). All 800 DNA props were tested with a PCR CAPS marker that was available for m235. The vast majority of plants tested were homozygous for the Landsberg erecta polymorphism with m235, which was expected if GI mapped close to m235. However, 13 plants were identified that were heterozygous for Landsberg erecta and Columbia polymorphisms, and were presumed to carry cross-overs between m235 and gi.

Figure 7:
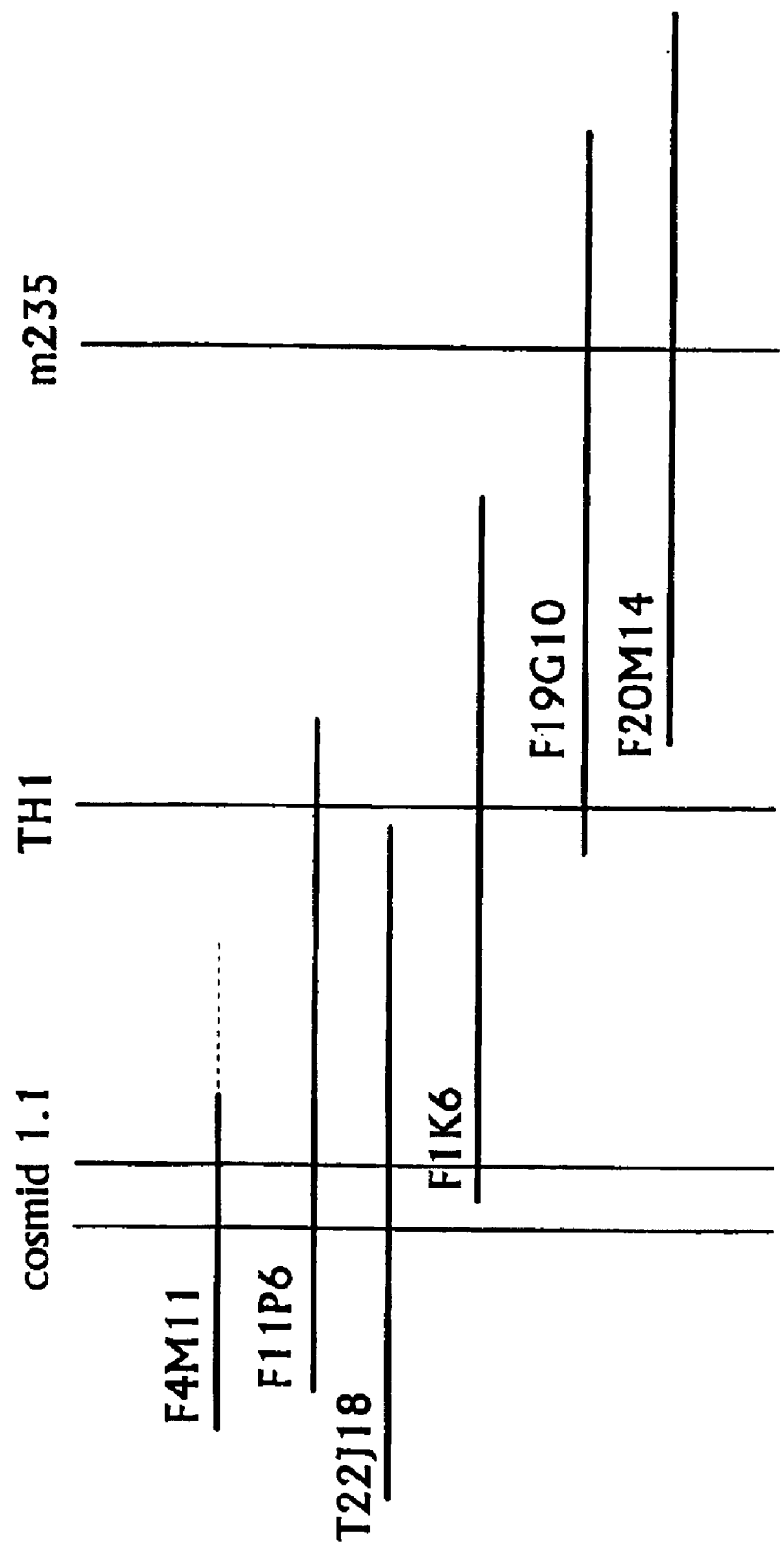
FIG. 7 is a genetic map. The bold horizontal lines show BAC clones of *Arabidopsis* DNA. The vertical lines show the positions of genetic markers on the physical map of BAC clones. M235 and TH1 were positioned relative to GI by genetic mapping. Cosmid 1.1 was isolated by hybridisation to the DNA fragment that is adjacent to the T-DNA in the putatively tagged GI mutant line. Cosmid 1.1 is located in the position expected for GI based on the genetic mapping with TH1 and m235.

These 13 recombinants were then tested with a second CAPS marker. This marker, TH1, was made using the DNA sequence of BAC F19G 10 that was available from the *Arabidopsis* genome sequencing programme. When the 13 recombinants with cross-overs between g1 and m235 were tested with TH1, 8 were found to be homozygous for Landsberg erecta polymorphisms and 5 were heterozygous for Landsberg erecta and Columbia This suggested that GI was close to TH1, and was on the opposite side of TH1 from m235. The physical map of the region is shown in FIG. 7, and the positions of both of these markers are shown.

The cosmid 1.1 was hybridised to the BAC clones that make up the physical map. As shown in the figure this hybridised to BAC clones that also hybridised to TH1 and was on the side of TH1 expected for GL These data are therefore consistent with cosmid 1.1 being located at the position expected for GI.

Analysis of Additional gi Alleles

In order to test for changes to the DNA structure in the 6 classical gi mutant alleles, primers were designed that amplified fragments of DNA around the insertion site of the T-DNA. One pair of primers used were pfl6 forward (GTTCAGACGTTCAAAGGC) (SEQ ID NO:14) and pfl6 reverse (AACTCCAATCCCAAAACC) (SEQ ID NO:15) that amplified a fragment extending from bases 18634 to 21169 in the Terryn sequence. This was used to amplify the fragment from all 6 gi alleles (gi-1 to gi-6) and from Landsberg erecta and Columbia wild-types. The fragments were run out on an agarose gel, but no obvious change to the fragment size was detected in any of the mutants. To test more stringently for changes, this fragment was then cleaved with the restriction enzyme HaeIII, and the resulting fragments separated on an agarose gel. Six fragments were expected in this digestion and these were 16, 820, 266, 70, 242 and 1121 bases long. In the wild-type controls and five of the mutants four fragments were detected on the agarose gel, these were 820, 266, 242 and 1121 bases long, while the 16 and 70 bp fragments were too small to be detected on the gel. However, in allele gi-1 the 242 bp fragment was missing, and was replaced by a fragment that was approximately 300 bp long. The 242 bp fragment and the 70 bp fragment are adjacent to one another in the gene 5 sequence, and this arrangement in gi-1 could have occurred if the mutation had removed the HaeIII site that separates these two fragments, producing a larger fragment. This HaeIII site is located at position 19805 in the Terryn sequence, which in turn is within the predicted exon 11 of gene 5. Therefore gi-1 causes a disruption in the gene 5 sequence, which taken together with the alteration in the T-DNA tagged allele strongly suggests that gene 5 is the GI gene.

Isolation and Sequencing of a Second cDNA from Arabidopsis Encoding a Polypeptide Having GI Function RNA was extracted from *Arabidopsis* seedlings by the method of Logemann et al (1987). This was converted into cDNA as described by Putterill et al (1995). The GI cDNA was then amplified in three fragments by PCR using primers designed from the genomic sequence. The three fragments were amplified with the following primers:

5' fragment with oli26 (TTCGGTTCCTGGATGGCT) (SEQ ID NO:16) and oli2R (TGGTTCAAGAGCTGGAAG) (SEQ ID NO:17);

middle clone with oli28 (TGGAGAGCTCAAGCCGCCAACCAT) (SEQ ID NO:18) and oli30R (CTCTTGCTACCACTAGACTGTGCTTC) (SEQ ID NO:19); and 3' clone with oli29 (CACAGTCTAGTGGTAGCMGAG) (SEQ ID NO:20) and oli7R (GTGGGTGCTCGTTATTGG) (SEQ ID NO:21).

These three fragments were then sequenced using a cycle sequencing kit purchased from Perkin Elmer. The results are shown in FIG. 8 (nucleotide sequence) (SEQ ID No: 5) and FIG. 9 (amino acid sequence) (SEQ ID NO: 6).

As can be seen from FIG. 8, the nucleotide sequence was identical to the sequence of FIG. 5 except that 18 extra bases were contained within the 5' fragment.

Homology to Rice ESTs

The predicted protein sequence of gene 5 (FIG. 6) (SEQ ID NO: 4) was compared to DNA sequences in the Genbank EST database, translated in all 6 open reading frames using BLASTP (Altschul et al., (1990)). Gene 5 showed homology to a number of rice ESTs. These ESTs were homologous to different parts of the protein. Rice EST C73052 showed homology to the amino terminus of the gene (residues 30 to 262). Rice EST C72988 showed homology to residues 591 to 748. Rice EST D40642 showed homology to residues 958 to 1073 (see FIG. 10—81.237% similarity and 71.443% identity).

A Rice cDNA Derived From a Probable Orthologue of GI

The three rice EST's (C73052, C72988, and D40642) discussed above were short fragments of longer cDNAs. To obtain longer sequences, the size of the cDNAs present in each of the ESTs was determined by restriction enzyme digestion. The longest clone was C73052, which contained a cDNA of approximately 3.3 kb.

To derive as long a rice sequence as possible from these three cDNAs, they were sequenced using primers that annealed to the vector sequences on each side of the cDNA insert. The primers used were T7 (5'-AATACGACTCACTATAG) (SEQ ID NO:22), M-13-20 (5'-GTAAAAACGACGGCCAGT) (SEQ ID NO:23) and M13-reverse (5'-AACAGCTATGACCATG) (SEQ ID NO:24). The sequences obtained in this way were then extended using primers that annealed to the rice sequences obtained with the vector primers. The primers used were rice 1-F (5'-CCCACAACTTATGCCATCCAC) (SEQ ID NO:25), rice 2-R (5'-CCTCAGAGGAATGATTATCAC) (SEQ ID NO:26), rice 3-F (5'-GCCATGCTTAAATGCACTGTC) (SEQ ID NO:27) and rice 4-R (5'-TTGTCAGCAAGTGAGTGGG) (SEQ ID NO:28). These four primers were used to sequence clone C73052.

A second set of primers were then made to extend the sequence further.

These were desired to anneal to the ends of the sequences obtained with rice primers rice 1,2,3,4 described above, and were rice 5-F (5'-CAGATGCACTTGATGCAGCAG) (SEQ ID NO:29), rice 6-R (5'-AGCAGCTACAACAATTTCAGC) (SEQ ID NO:30), rice 7-F (5'-GTCAGAAGCAGGAGCTATG) (SEQ ID NO:31) and rice 8-R (5'-TTCACCATCAACAAGCATTCC) (SEQ ID NO:32). To finally complete and confirm the sequence of EST C73052 two further primers were used. These were rice 9-R (5'-CCTTGTCTCTTCTT) (SEQ ID NO:33) and rice 10-F (5'-CTCTGTTCTCCTTGAAGCC) (SEQ ID NO:34).

The sequence of the longest open reading frame extending 2034 bp is shown in FIG. 11 and the predicted protein sequence is shown in FIG. 12 and compared with the *Arabidopsis* protein sequence of GI in FIG. 13.

Strategies to Extend the Rice GI EST

Comparison of the predicted sequence of the protein encoded by the rice EST with the sequence of the predicted *Arabidopsis* GI protein indicates that the rice sequence is not full length. The rice protein is probably approximately 183 amino acids longer than is shown in FIG. 12.

Several strategies could be used to provide a full length cDNA. The most commonly used method is to complete the cDNA by 5' RACE. In this method a full length cDNA can be isolated by using a gene specific primers and a non-specific primer that anneals to a homopolymeric tail added to the 3' end of the single stranded cDNA. Such methods are often called rapid amplification of cDNA ends or RACE (See Boehringer Mannheim Catalogue, 1996, p 143; Boehringer Mannheim 5'/3' RACE kit, Catalogue No. 1734 792).

A 5' RACE method could therefore be used to isolate the 5' end of the rice cDNA. This would require the isolation of RNA from rice plants by standard methods, the synthesis of single strand cDNA (as described by Boehringer Mannheim Catalogue, 1996, p 143; Boehringer Mannheim 5'/3' RACE kit, Catalogue No. 1734 792), the use of terminal transferase to add a homopolymeric A-tail to the 3' end of the cDNA, and amplification of the tailed cDNA by PCR using a specific primer for the rice GI gene close to the end of the existing sequence (5'-CTTCTMTACCCAGAGGTGC) (SEQ ID NO:35) and the oligo dT-anchor primer (as described Boehringer Mannheim Catalogue, 1996, p143; Boehringer Mannheim 5'/3' RACE kit, Catalogue No. 1734 792). The obtained cDNA is further amplified by a second PCR using a nested specific primer for the rice GI gene (5'-GCAATATGTCTGTGATCCAAGG) (SEQ ID NO:36) and the PCR anchor primer (as described Boehringer Mannheim Catalogue, 1996, p143; Boehringer Mannheim 5'/3' RACE kit, Catalogue No. 1734 792). The RACE products can be cloned into an appropriate plasmid vector such as Bluescript for sequencing.

Part B
Plant Material and Growth Conditions

Arabidopsis thaliana L. Heynh (Arabidopsis) wild types were ecotypes Columbia, Landsberg erecta (Ler, obtained from Lehle Seeds, Round Rock, Tex.) and Ws (obtained from the Arabidopsis Biological Resources Centre, Ohio). The GI mutants used were gi-1 and gi-2 (Columbia ecotype, obtained from the Arabidopsis Biological Resources Centre, Ohio), gi-3 to gi-6 (Ler ecotype, obtained from Maarten Koornneef, Wageningen, the Netherlands), gi-11 (T-DNA mutant allele in Ws ecotype; Richardson et al. 1998) and gi-12 (T-DNA mutant allele in Col ecotype, a gift from M. Aukerman and R. Amasino, University of Wisconsin, Wis.). The ARLY FLOWERING 3 (elf3, Columbia ecotype), was obtained from the Arabidopsis Stock Centre and has been described previously (Zagotta et al. 1996). The LATE ELONGATED HYPOCOTYL mutant (LHY, Ler ecotype) was described previously (Schaffer et al. 1998). Seed of transgenic plants over expressing the CIRCADIAN CLOCK ASSOCIATED (CCA1) gene (35S::CCA1) was a gift from Elaine Tobin (UCLA, California) and has been described previously (Wang and Tobin, 1998).

Seeds were placed on moist filter paper at 4 DC for 3 days, planted in soil and germinated in growth cabinets. Plants were grown in Percival AR-32L cabinets providing either continuous light (LL), continuous dark (DD), short days (SD) of 10 h light/14 h dark, or long days (LD) of 18 h light/6 h dark unless otherwise noted. Light intensity of 150–170 $\mu$mol m$^{-2}$ s$^{-1}$ was provided by fluorescent tubes.

Measurement of Flowering Time

Flowering time analysis of gi alleles and wild type was carried out on plants grown in Gallenkamp cabinets either in SD (10 h light/14 h dark) or in LD (10 h light+8 hr day extension/6 h dark) as described in Putterill et al. 1995. Flowering time was measured by number of leaves when floral buds were visible at the centre of the rosette.

Detection of mRNA by Northern Hybridisation Analysis

RNA was extracted from plant tissue as described in Stiekema et al. (1988). Total RNA (10 $\mu$g) was electrophoresed on agarose gels and transferred to Boehringer Mannheim positively charged nylon membrane as described in Fourney et al. (1988). RNA was bound to the membrane using a UV Stratalinker (Stratagene). The GI probe used in northern hybridisation analysis was a 1817 bp cDNA fragment from the 3' half of the GI cDNA (2235–4051 on G cDNA). This probe is specific for the GI transcript as it does not detect any transcript in gi-11 mutant plants which carry a deletion of the 5' end of the gene and promoter. GI DNA probes were radio-labelled by priming with random octamers (Gibco BRL). The radio-labelled DNA was hybridised to the northern blot membranes in hybridisation buffer for 18 h at 65° C. and then washed at moderate stringency using two washes of 0.5 or 1×SSC, 0.1% SDS at 65 CC.

The LHY probe used in northern hybridisation analysis was the full length LHY cDNA Genbank accession AJ006404. LHY DNA probes were radio-labelled and hybridised to northern blot membranes as described above.

After northern hybridisation, nylon membranes were exposed to a Fujifilm BAS-MP imaging plate at room temperature. The image was visualised using a Fujifilm FLA-2000 phosphorimager running Imagereader version 1.3E software. The expression levels were quantitated using the MacBAS version 2.5 program and background hybridisation levels subtracted. Expression levels were normalised against the signal obtained by hybridising the blot with an asparagus 25/26s rDNA probe. The normalised values were then expressed as a proportion of the highest value obtained and graphed.

Detection of mRNA by RT-PCR

First strand cDNA synthesis on 10 ug of total RNA was primed using the dT$_{17}$ adapter primer as described by Frohman et al. 1988. For CO detection, the first strand product was used in PCR containing a primer CO$_{53}$ 5'-acgccatcagcgagttcc corresponding to position 295–311 bp located 295–311 bp downstream of the translation start of CO (Genbank) and co oli9 primer 5'-aaatgtatgc-gttatggttaatgg spanning the single intron of CO where the position of the intron is indicated by a -. The specificity of the PCR for CO sequences was analysed by including total RNA from the co-8 allele( ) which is deleted for the region encompassed by the primers amplified. No PCR products were detectable in the co-8 RT-PCR reaction unpublished results). Amplification of ubiquitin mRNA was used as a control to ensure that equal amounts of first strand cDNA were added to each PCR reaction. The primers used to amplify ubiquitin cDNA were UB01 5'-ctaccgtgatcaagatgcac and G702 (Frohman et al. 1988). PCR was terminated while the amplification was occurring exponentially as previously described (Putterill et al. 1995). Amplification of CO was carried out for 25 cycles and of ubiquitin for 20 cycles. The PCR products were analysed by southern hybridisation using either a full length CO probe or an ubiquitin probe.

Detection of GI Protein by Western Analysis

Two GI peptide sequences were synthesised. These were T P K L P T T E K N G M N S P S Y R F F N (SEQ ID N at a peak of hydrophilicity at amino acid 1106 (close to a strong SS-turn-predictor of potential B cell epitopes) and E R E L Q P W I A K D D E E G Q K M W K(SEQ ID NO:38) at amino acid 971.

Effect of gi Mutations on the Predicted GI Protein and on Flowering Time

To confirm the molecular identity of the GI gene, the corresponding gene from six classical gi mutant alleles (gi-1 to gi-6) was sequenced. The gene was amplified by PCR from genomic DNA of the mutant alleles in three overlapping fragments which were sequenced directly. Alterations in the predicted GI sequence were identified in all six alleles, confirming the identity of the GI gene.

Figure 15:
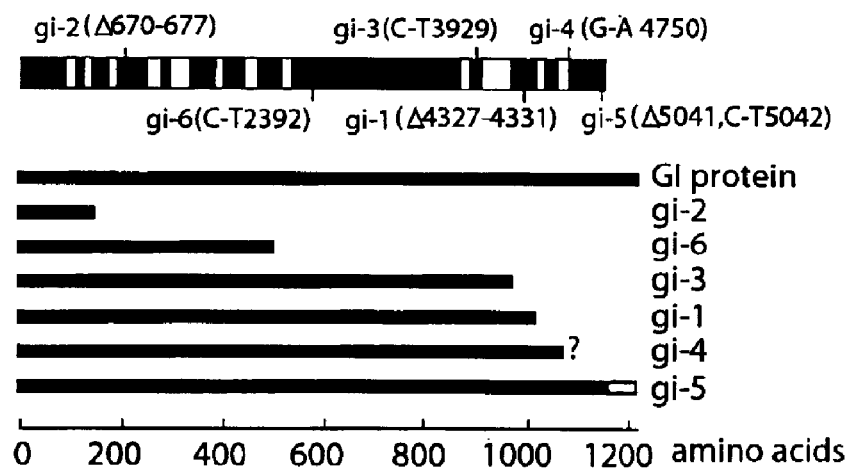
FIG. 15 shows the effect of gi mutations on the GI protein and on flowering time. Effect of the gi mutations on the GI protein. The position of the mutations in gi-1 to gi-6 on the transcribed region of the GI gene (top). The positions of the gi mutations correspond to the genomic sequence of the GI gene with position 1 at the A of the translation start codon. Exons in the transcribed region are in black and introns are in white. Sequence deletions are indicated by a triangle. The size and structure of the predicted gi mutant proteins are compared. In gi-4, a mutation in the 3' splice acceptor site of intron 12 is expected to cause aberrant splicing of the intron with unknown effects on the C-terminal end of the protein (?). In gi-5, the last eight amino acids of the predicted GI protein are altered and 27 amino acids are added to the carboxyl terminus of the GI protein (light grey bar).

Four of the six gi mutant alleles are predicted to encode truncated GI proteins (FIG. 15B). The most extreme of these is the X-ray induced gi-2 allele where an eight bp deletion (670–677 downstream of the ATG) causes a frameshift. This introduces a stop codon which shortens the predicted 1173 aa GI protein by 1029 amino acids. A transition (C to T, 2392 bp downstream of the ATO) in the EMS-induced gi-6 allele, results in a stop codon which truncates the predicted GI protein by 681 amino acids. The gi-3 allele is also EMS induced and has a C to T transition (3929 bp downstream of the ATG) causing a stop codon. This shortens the predicted GI protein 210 amino acids. A five bp deletion (4327–4331 bp downstream of the ATG) in the gi-1 allele X-ray induced) causes a stop codon immediately downstream that results in truncation of the GI protein by 171 amino acids.

Of the remaining two alleles, the EMS allele gi-4 has a mutation in the 3' splice acceptor site of intron 12 of the GI gene (4150 bp downstream of the ATG). The change from AG to AA is expected to result in aberrant splicing of intron 12 from the GI transcript. Finally, X-ray allele gi-5 has a point mutation and a single base deletion in exon 13 of the GI gene (5141 and 5042 bp downstream of the ATG). This causes a frameshift which is predicted to both change the last eight amino acids and add 27 amino acids to the carboxyl terminus of the GI protein (FIG. 15B).

Figure 16:
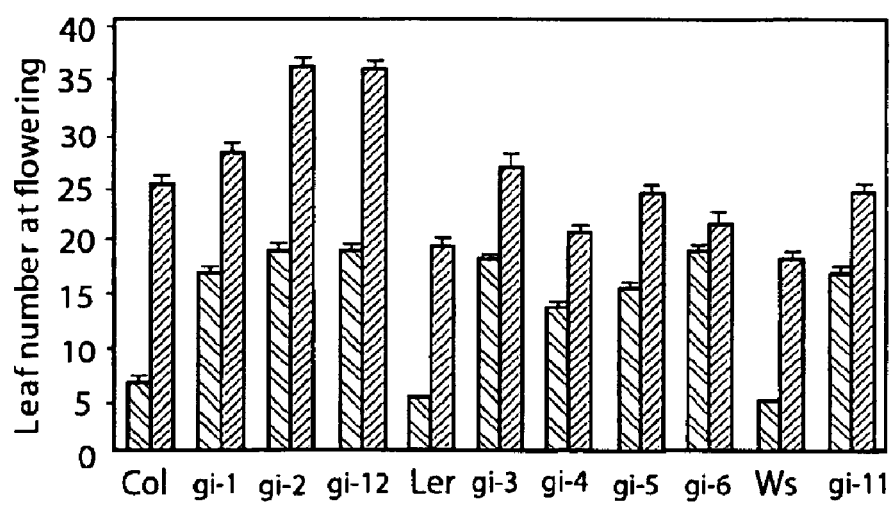
FIG. 16 shows the flowering time of wild type and gi mutants under LD and SD conditions. The genotype tested is shown along the horizontal axis and the leaf number at flowering is plotted on the vertical axis. Black bars show flowering time in LD conditions and grey bars are those under SD conditions.

To determine the functional importance of different domains of the GI protein, we compared the effect of the six classical gi mutant alleles (gi-1 to gi-6) on *Arabidopsis* flowering time. The T-DNA mutant alleles (gi-11 and gi-12) were also included in the experiment. gi-11 was known to be a null mutation. The 5' half of the GI gene is deleted in gi-11 and no GI transcript was detected (S. Fowler and J. Putterill, unpublished results). The mutants and their corresponding wild type plants were grown in LD and SD conditions and scored for numbers of leaves visible at flowering (FIG. 16).

The flowering time experiment showed that the null allele gi-11 delayed, but did not abolish flowering, indicating that the GI gene promotes flowering, but is not essential for it to occur. Of the classical alleles, the mutation with the most severe effect on the GI protein, gi-2 was the latest flowering while gi-4 (splice site mutation at the last intron exon boundary at the 3' end of the GI gene) was the earliest flowering. However, the differences in flowering time between these alleles were relatively slight strongly suggesting that the carboxyl terminus of the GI protein is functionally important in flowering.

The gi mutations in the Ler and Ws ecotypes caused late flowering and flowered with much reduced daylength sensitivity compared to wild type plants, as previously reported for gi mutants (Redei, 1962; Koornneef et al. 1991, Araki and Komeda, 1993). However, the mutant plants all flowered slightly later than wild type in short days. This result is consistent with the main function of GI being to promote flowering in long days, but indicates that GI also has some role in flowering in short days in the experimental conditions. In addition, the severe gi-2 and gi-12 Col mutants responded quite strongly to daylength (FIG. 16) which is inconsistent with previous reports where gi-2 was found to be daylength insensitive (Araki and Komeda, 1993). It is not clear what the reasons are for the differences in the results between the two experiments, but it, may be due to light quality differences in growth conditions. gi mutants have previously been shown to have impaired light perception or response as they can have elongated hypocotyls compared to wild type in a range of light regimes (Araki and Komeda, 1993; K. Lee and G. Coupland, unpublished results).

GI Transcript Levels are Regulated by the Circadian Clock and the Transition to Darkness To determine where and when in the plant GI might exert its effect on flowering, GI expression was analysed through development by northern hybridisation analysis. An initial experiment using northern blots with RNA extracted from plants harvested at the beginning of the day failed to detect GI transcript. Subsequently, northern analysis of RNA extracted from plants collected through LD indicated that GI transcript levels cycled, with a peak of expression about half way through the light period (data not shown). In a second experiment, plant material was collected every 2–4 hours over a 24 hour period in LD. Northern hybridisation analysis confirmed that GI transcript levels cycled, with the highest level 10 h into the light (Zeitgeber 10, ZT 10) and the lowest level at the beginning of the day (ZT 0, FIG. 17).

To determine if the rhythmic cycling of GI transcript levels was under the control of the circadian clock, plants entrained in LD were transferred to continuous light photoperiods (LL) for 24 h and then assayed for GI expression every 4–8 over a 48 h period. Under LL, GI transcript levels continued to cycle indicating that they were controlled by the circadian clock (FIG. 17). Plants were also transferred to continuous dark photoperiods (DD) and GI transcript levels analysed. In DD, GI transcript continued to cycle, but the amplitude was reduced and moderate GI expression was detected at all the timepoints analysed (data not shown).

Transcript levels of the flowering time gene CO are lower in SD than in LD and this correlates with delayed flowering seen in SD in wild type plants. To determine if GI transcript levels were also lower in SD than in LD, plant material was collected every 2–4 hours over a 24 hour period in SD. Northern hybridisation analysis showed that GI transcript levels cycled in SD with the highest level 8 h into the light (ZT 8, FIG. 17). The peak of GI expression in SD was 2 h earlier than in LD, but was a similar or higher level as in LD days. The rapid reduction in GI expression in SD coincided with the onset of darkness at ZT 10. Similar results were obtained in a second experiment (data not shown).

To test whether GI transcript levels were down-regulated by the transition to darkness in SD, plants growing in LD were exposed to darkness at ZT 10 and assayed every hour, for four more hours. GI transcript levels at ZT 11 in the plants in darkness were reduced to – half the level of control LD plants, indicating that they are regulated by the transition to darkness (FIG. 17). Similar results were obtained in a second experiment (data not shown).

This result raises the possibility that the timing of peak GI expression may be important for rapid flowering of wild type plants in LD.

Figure 18B:
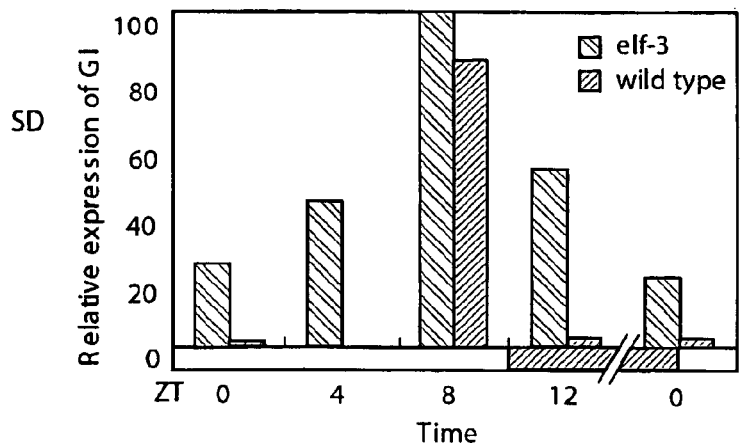
Figure 18C:
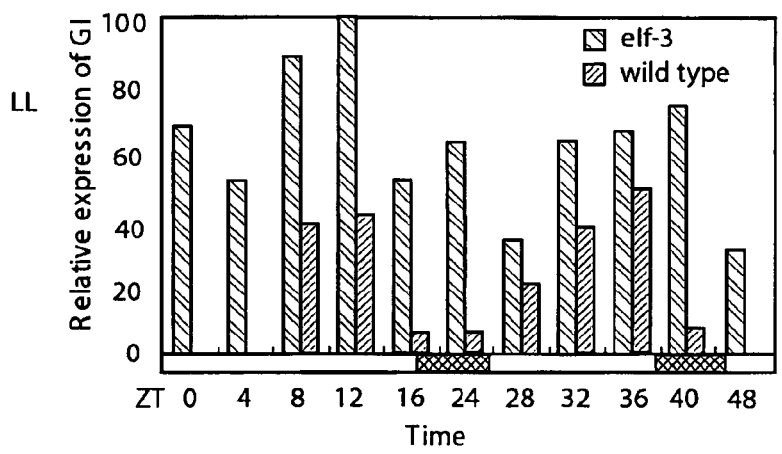

The Early Flowering *Arabidopsis* elf3 Mutants Show Ectopic over Expression of GI in Long and Short Day Photoperiods The effect of the elf3 mutation on GI transcript levels in LD and SD was assayed every 4 h over a 24 h period (FIG. 18). In elf3 mutants, unlike wild-type plants, GI transcript was detected at all timepoints analysed including the beginning of the light period (ZT 0) and after the transition to darkness in SD (ZT 10). GI transcript levels were also higher in elf3 mutants than in wild type at all timepoints. GI transcript levels cycled in elf3 mutants in LD and SD, but with much reduced amplitude.

This result indicates that early flowering of in SD correlates with the presence of GI transcript even after the transition to darkness.

Effect of *Arabidopsis* Circadian Mutations on GI Expression

To further investigate how the circadian clock controls GI expression, the effect of three circadian genes from the long day on the free running rhythmn of GI expression was analysed. elf3 and lhy mutant plants and 35S::CCA1 transgenic plants were grown in LD, transferred to LL for 24 h and then assayed for GI expression every 4–8 h over a 48 h period.

Figure 19:
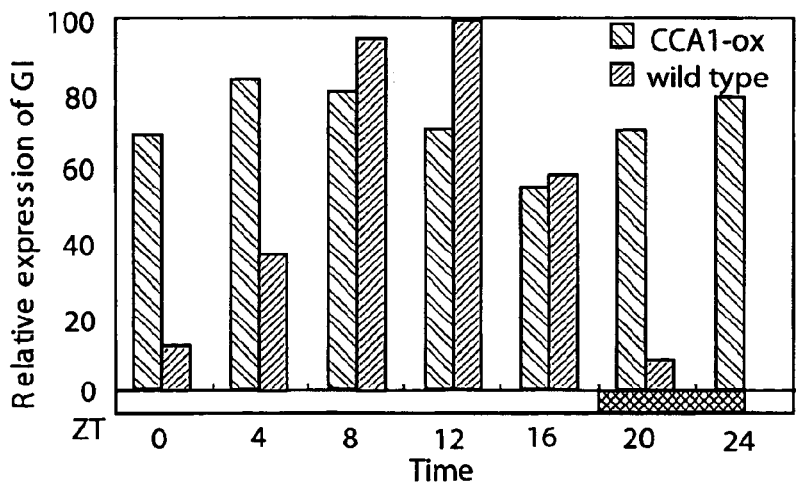
FIG. 19 shows the effect of the CCA1-OX transgene on GI expression. Plants were grown in LD or SD conditions until the six leaf stage and shifted to continuous light 24 hours before tissue harvesting was initiated at ZT 0. Hatched bars represent subjective night. Total RNA (10 $\mu$g) was extracted from aerial parts. GI transcript levels were analysed by northern hybridisation using a GI cDNA probe. Results are presented as a proportion of the highest value after normalisation with respect to 25/26s rRNA levels.
Figure 20A:
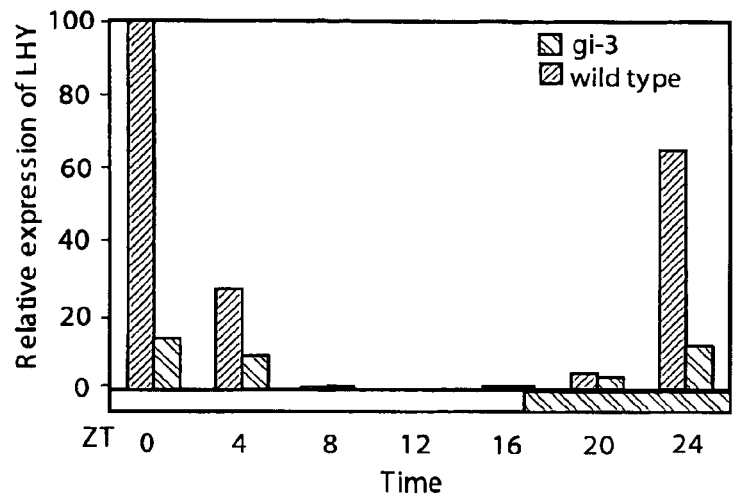
FIGS. 20A, 20B, 20C and 20D show the expression of LHY, CCA1, CAB and CO in gi mutants. gi-3 mutant plants were grown in LD conditions until the six leaf stage. Horizontal bars under each graph represent the light (white) and dark (black) conditions provided. ZT 0 hr is at lights on. Total RNA (10 µg) was extracted from aerial parts. A. LHY transcript levels were analysed by northern hybridisation using a LHY cDNA probe. Results are presented as a proportion of the highest value after normalisation with respect to 25/26s rRNA levels. B. CCA1 transcript levels were analysed by northern hybridisation using a CCA1 genomic probe. Results are presented as a proportion of the highest value after normalisation with respect to 25/26s rRNA levels. C. CAB transcript levels levels were analysed by northern hybridisation using a CAB genomic probe. Results are presented as a proportion of the highest value after normalisation with respect to 25/26s rRNA levels. D. CO transcript levels were analysed by RT-PCR at two timepoints ZT 0 hr and ZT 12. Results are presented as a proportion of the highest value after normalisation with respect to UBQ mRNA levels.
Figure 20B:
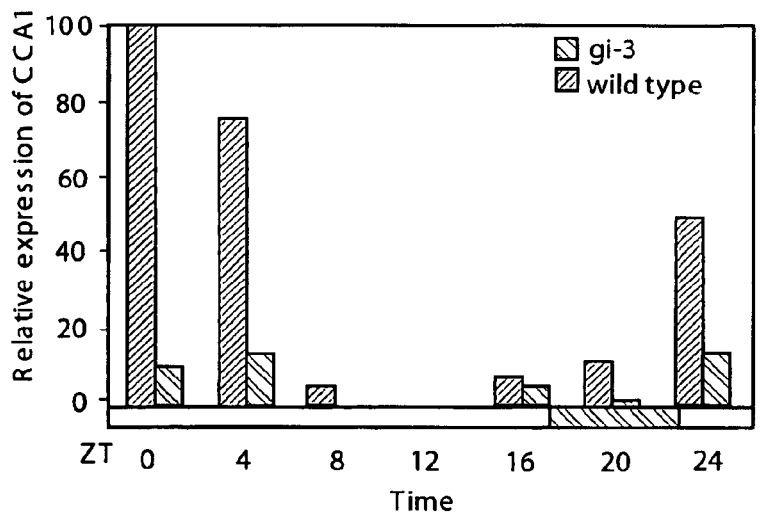
Figure 20C:
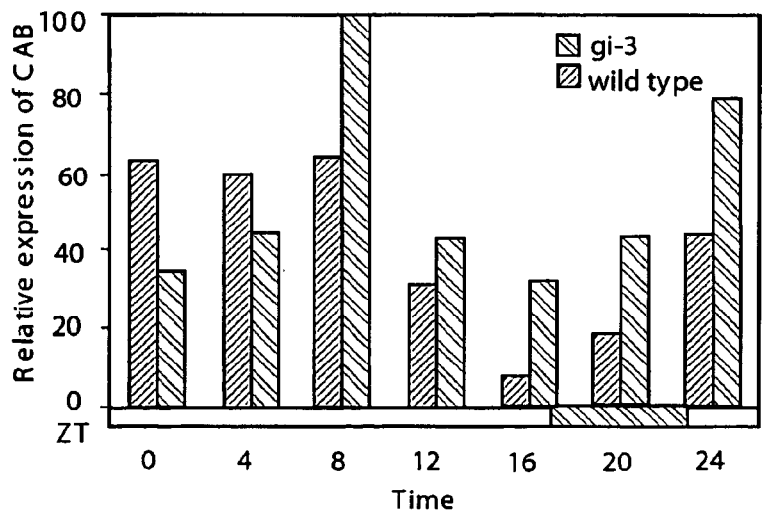
Figure 20D:
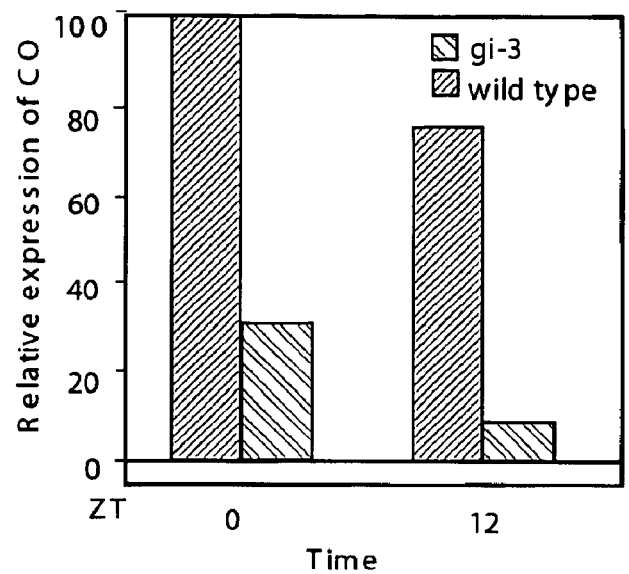

In elf3 and 35S::CCA1 plants in LL, the rhythmic pattern of GI expression was disrupted. GI was detected in at all the timepoints analysed and was present at higher levels in elf3 mutants than in wild type (FIG. 19). GI transcript levels fluctuated in elf3 mutant plants. This result indicated that the circadian rhythmn of GI expression in the light is regulated via elf3 and CCA1.

Surprisingly, in lhy mutants, GI transcript levels continued to cycle in LL. This result indicated that circadian clock regulation of GO transcript levels occurs independently of the LHY gene. GI expression is the only circadian rhythmn tested to date that is not disrupted in lhy plants.

The GI Mutation Lowers the Expression of Two Genes, LHY and CO, in the Long Day Pathway The expression analysis described above showed that the LHY gene did not appear to regulate GI expression. Hence LHY expression in gi mutant plants in LD and SD was analysed. The gi mutation led to a 5–6 fold reduction in peak LHY transcript levels in LD. A similar result was obtained in gi mutants grown in SD. LHY transcript levels continued to cycle in LD and SD conditions in gi mutant plants as observed previously in wild-type plants (Schaffer et al. 1998). These expression results indicate that GI may lie upstream of the LHY gene in the long day pathway, rather than downstream as predicted by current models.

The level of CO transcript correlates well with *Arabidopsis* flowering time. Plants grown in SD have lower levels of CO transcript than plants grown in LD (Putterill et al. 1995) and ectopic over-expression of CO dramatically accelerates flowering in both LD and SD (Simon et al. 1996, Coupland, 1997). The level of CO expression in gi mutant plants was measured in LD every 4 h over a 24 h period by RT-PCR (FIG. 20). The gi-3 mutation led to a 3–6 fold reduction in CO transcript levels at all timepoints analysed compared to wild type plants. This result suggests that GI may promote flowering in LD via up regulation of expression of the CO gene.

GI is Expressed Throughout Plant Development

Figure 21:
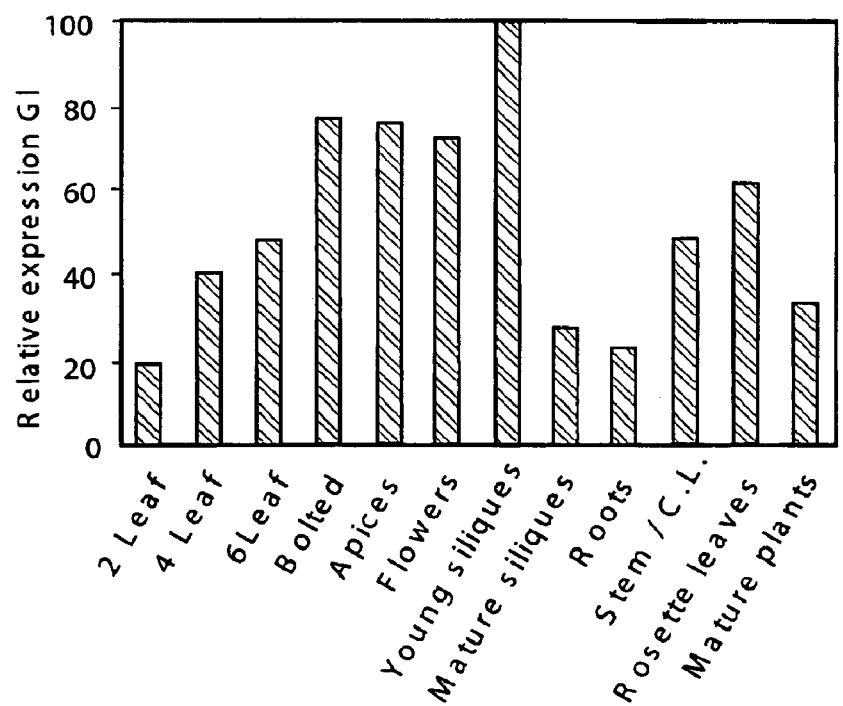
FIG. 21 shows the northern hybridisation analysis of GI expression throughout development. Total RNA was extracted from the aerial parts of LD grown plants at the stages shown (from two leaf stage to mature plant). Mature plants had siliques which were fully expanded but still green. RNA was also extracted from specific organs of mature plants as indicated. RNA (10 µg) was hybridised to a GI cDNA probe and the hybridisation signals were normalised and graphed.

The expression of GI transcript during plant development was analysed by northern hybridisation (FIG. 21). Plants were grown in LD and samples were harvested 8 h into the light period (ZT 8). GI transcript was detected at all the stages of plant development tested, from seedlings at the two leaf stage to mature plants with developed siliques. GI transcript levels were analysed in individual organs and tissues from mature plants. GI was detected in all of the tissues tested, with the highest level of GI expression in inflorescence apices, young flowers and young siliques and the lowest level in mature siliques and roots. The tissues with maximal GI expression are undergoing cell division which may indicate that GI is concentrated in regions of cell proliferation. However, this remains to be confirmed by in situ hybridisation experiments.

Discussion

Positioning GI in the Long Day Pathway to Flowering in *Arabidopsis*

Several genes in the *Arabidopsis* long day promotion pathway, including ELF3, LHY and CCA1 affect both photoperiodic control of flowering and circadian clock function. The above work shows that the ELF3 gene, which is predicted to provide light input signals into the clock, and CCA1 which is likely to be part of the clock itself, are both required for circadian regulation of GI transcript levels. These results suggest that GI lies downstream of ELF3 and CCA1 in the long day pathway.

In contrast, the lhy mutation which abolishes several different circadian rhythmns in plants including clock controlled gene expression, does not influence circadian regulation of GI expression. This result indicates that LHY may not regulate long day flowering via GI as previously thought. Other evidence supports the idea that GI may be upstream of LHY in the long day pathway. The results herein show that LHY expression is greatly reduced in gi mutant background. However it is not yet clear how LHY transcript levels per se correspond to flowering time, as under-expression of LHY is associated both with late daylength-insensitive flowering in the gi mutant and early daylength-insensitive flowering in the elf3 mutant (Schaffer et al. 1998).

The results also show that the expression of the CO gene is reduced in the gi mutant background in LD. This confirms that GI is likely to lie upstream of the CO gene in the pathway and to promote flowering at least in part via up regulating the levels of CO activity.

Possible Role for the GI Gene in Photoperiodic Flowering

Our gene expression analyses position the GI gene in the *Arabidopsis* long day promotion pathway downstream of CCA1 and upstream of LHY and CO. GI appears to promote flowering in LD at least in part via up regulating CO expression. High ectopic expression of GI in elf3 mutants and in 35S::GI transgenic plants causes early flowering. However, high GI expression does not always correlate with early flowering. For example, wild-type plants grown in SD have high levels of GI expression, yet still show delayed flowering. Hence, we think that the timing of GI expression during day night cycles may be important for flowering. For example, in SD, the transition to darkness (at ZT 10) is associated with a dramatic reduction in GI expression at subsequent timepoints, compared to plants grown in LD and this might be responsible for the delayed flowering seen in SD. It is possible that the GI gene may influence photoperiodic flowering by being part of the daylength signalling or response mechanism in *Arabidopsis*.

Part C

Construction of a Plasmid to Enable the Over-Expression of GI in Plants and its Introduction into *Arabidopsis*

A GI cDNA was assembled from the fragments that were used for sequencing and are described in A above. The 5' region amplified with primers oli26 and oli2R was blunt-ended, cleaved with HindIII and ligated into pGIT-GIN cleaved with HindIII and SmaI. The middle section of the cDNA, amplified with primers oli28 and oli30R, was ligated to Bluescript plasmid cleaved with SacI and XbaI. The 5' fragment and the middle fragment were then ligated together with the plant binary vector pGREEN in a three way ligation. The plasmid containing the 5' fragment was cleaved with KpnI and SacI, the plasmid containing the middle fragment was cleaved with SacI and XbaI and pGREEN was cleaved with KpnI and XbaI. The resulting plasmid contained the 5' fragment ligated to the middle fragment at the SacI site and this longer fragment inserted into pGREEN between the KpnI and XbaI sites. The polyA sequence from the 35S gene of Cauliflower Mosaic Virus was inserted downstream of the GI cDNA fragment. The 3' clone amplified with oli29 and oli7R was cleaved with SpeI and SmaI and cloned into Bluescript. This fragment was then removed as a SpeI-EcoRI fragment and inserted into the GI cDNA plasmid cleaved with XbaI and EcoRI. The final plasmid contains the GI cDNA encoding the entire GI protein between the 35S promoter and the 35S poly A sequence in the binary vector pGREEN that carries a kanamycin resistance gene.

This plasmid was used to introduce the 35S: GI fusion into *Arabidopsis* plants using the transformation method of Clough and Bent (1998) (Plant Journal, Vol 16, pp. 735–743).

Effect of Over-Expression of the GI Gene in *Arabidopsis*

The pGREEN vector carrying 35S:GI described in the previous section was used for transformation of *Arabidopsis* plants.

The GI transgene was introduced into *Arabidopsis* plants by infiltrating plants with the *Agrobacterium* culture. Both wild-types and gi-3 mutants were used in the transformation. The progeny of infiltrated plants were germinated on kanamycin-containing medium and resistant plants selected.

These transformed T1 plants were scored for flowering time by counting the number of leaves they produced before flowering. Control wild-type plants formed 10–12 leaves under these conditions.

Thirty T1 wild-type plants into which 35S:GI had been introduced were scored. They produced the following flowering times:

| No. of transformants | Leaf No. |
| --- | --- |
| 4 | 7 |
| 10 | 8 |
| 5 | 9 |
| 3 | 10 |
| 8 | More than 10 |

A proportion of these transformants (for example those forming only 7 or 8 leaves) flowered significantly earlier than wild-type plants (10–12 leaves), indicating that over-expression of GI can promote early flowering.

Thirty-six transformants were also made in the gi-3 mutant background. These flowered with the following leaf numbers:

| No. of transformants | Leaf No. |
| --- | --- |
| 4 | 7 |
| 10 | 8 |
| 8 | 9 |
| 2 | 10 |
| 12 | More than 10 |

This indicates that over-expression of the GI cDNA can complement the GI mutation, and therefore that the cDNA described is functional. Furthermore, it again demonstrates that over-expression of the cDNA causes even earlier flowering than that of wild-type plants in a proportion of transformants, and therefore that GI over-expression can be used to manipulate flowering time.

Introduction of Plasmid into Plants other than *Arabidopsis*

The pGREEN vector described above is introduced into the following crops employing the following techniques:

Oil seed rape

*Agrobacterium*-mediated transformation using the approach of Kazan et al (1997)

Canola

*Agrobacterium*-mediated transformation using the approach of Kazan et al (1997)

Rice

Particle gun (biolistics) approach of Christou et al (1991) or *Agrobacterium*-mediated transfer as described by Hiei et al (1994).

INDUSTRIAL APPLICATION

Thus, the present invention provides, for the first time, isolated nucleic acid encoding polypeptides having GI function. This in turn leads to numerous applications in practice, primarily in the manipulation of flowering and/or starch accumulation in plants.

Specific applications of the invention in manipulating flowering are as follows:

Promotion of GI Activity to Cause Early Flowering.

Mutations that reduce GI activity cause late flowering under inductive long day conditions, indicating GI involvement in promoting flowering under long days. This suggests that flowering could be manipulated by using foreign promoters to alter the expression of the gene.

Causing Early Flowering Under Non-Inductive Conditions.

Manipulation of GI transcript levels under non-inductive conditions may lead to early, or regulated, flowering. Promoter fusions enable expression of GI mRNA at a higher level than that found in wild-type plants under non-inductive conditions.

Use of CaMV35S or meri 5 fusions should lead to early flowering while use of GSTII fusions should lead to regulated flowering.

Causing Early Flowering Under Inductive Conditions.

The level of the GI product may be increased by introduction of promoter, eg CaMV3SS or meri 5, fusions. Inducible promoters, such as GSTII, may be used to regulate flowering, eg by first creating a GI mutant of a particular species and then introducing an inducible promoter-GI fusion capable of complementation of the mutation in a regulated fashion.

Inhibition of GI Activity to Cause Late Flowering.

gi mutations cause late flowering of *Arabidopsis*. Transgenic approaches may be used to reduce GI activity and thereby delay or prevent flowering in a range of plant species. A variety of strategies may be employed.

Expression of Sense or Anti-Sense RNAs.

In several cases the activity of endogenous plant genes has been reduced by the expression of homologous antisense RNA from a transgene, as discussed above. Similarly, the expression of sense transcripts from a transgene may reduce the activity of the corresponding endogenous copy of the gene, as discussed above. Expression of a GI antisense or sense RNA should reduce activity of the endogenous gene and cause late flowering.

Expression of Modified Versions of the GI Protein

In the case of GI modification of the gene in vitro and expression of modified versions of the protein may lead to dominant inhibition of the endogenous, intact protein and thereby delay flowering. This may be accomplished in various ways, including the following.

Specific applications of the invention in manipulating starch are as follows:

Promotion of Starch Accumulation and/or Characteristics

A similar approach to control and expression of the GI gene in plants can be taken where promotion of starch accumulation in photosynthetically active tissues (such as the leaves) of a transgenic plant is the intended result.

The higher accumulation of starch in gi mutants may have commercial opportunities. For example, GI could be used to inactivate the gene in other species, with, for example, anti sense or co-suppression technologies. This may then cause starch to accumulate in plant species with large leaves, making it easier to harvest the starch. By introducing other transgenes it may also be possible to manipulate the chemistry of the starch, to make forms which are of high commercial value.

Increasing Forage Value

Another aspect of increasing the starch content of leaves is that it may enhance the energy value of animal forage eg pasture grasses, forage maize, alfalfa, etc). When carbohydrate (energy) is provided as starch it is more stable than as the water soluble carbohydrates. These water soluble carbohydrates may necessitate drying or may wash through in an ensiling process. Furthermore, the resulting fresh forage requires less handling and other input (eg drying).

Other implications and applications of the invention will be apparent to those persons skilled in the art. It will also be appreciated that the invention is not limited by the specific description provided, but instead that modifications may be made (eg. in terms of vector systems, transformation protocols, plant promoters, etc.) without departing from the scope of protection.

REFERENCES

Altschul, S. F., Gish, W., Miller, W., Myers E. W. and Lipman, D. J. (1990). Basic alignment search tool. *J. Mol. Biol.* 215:403–410.

Araki, T., Kobayashi, Y., Kaya, H. and Iwabuchi, M. (1998). The flowering-time gene FT and regulation of flowering in *Arabidopsis*. *J. Plant Res.*, 111, 277–281.

Araki, T. and Komeda, Y. (1993). Analysis of the role of the late flowering locus, GI, in the flowering of *Arabidopsis thaliana*, Plant J. 3:231–239.

Bechtold, N., Ellis, J. and Pelletier G. (1993) In planta Agrobacterium mediated gene transfer by infiltration of adult *Arabidopsis thaliana* plants. *Comptes Rendus des seances de l' Acadamie des Sciences. Sciences de la vie* 316:1194–1199.

Benfey et al., *EMBO J.* 9: 1677–1684 (1990a).

Benfey et al., *EMBO J.* 9: 1685–1696 (1990b).

Bouchez, D., Camilleri, C., and Caboche M. (1993). A binary vector based on Basta reistance for in planta transformation of *Arabidopsis thaliana*. *Comptes Rendus des seances de l'Acadamie des Sciences. Sciences de la vie* 316:1188–1193.

Christou, P., Ford, T. L., Kofron, M. 11991). Production of transgenic rice (*Oryza sativa* L.) plants from agronomically important indica and japonica varieties via electric discharge particle acceleration of exogenous DNA into immature zygotic embryos. Bio/technology 9:957–962.

Colasanti, J. and Sundaresan, V. (1997). Long distance signals for flowering: genetic evidence that the maize INDETERMINATE gene regulates a floral stimulus. *Flowering Newsletter*, 24, 4–9.

Coupland, G. (1997). Regulation of flowering by photoperiod in *Arabidopsis*. *Plant Cell Environ,* 20, 785–789.

Doyle, J. J. and Doyle, J. L. (1990). Isolation of plant DNA from fresh tissue. *Focus* 12:13–14.

Eimert, K., Wang, S-M., Lue, W-L., Cheng, J. (1995) Monogenic recessive mutation cause both late floral initiation and excess starch accumulation in *Arabidopsis*. Plant Cell. 7:1703–1712.

Fourney, R. M., Miyakoshi, J., Day, R. S. and Paterson, M. C. (1998) Northern blotting: efficient RNA staining and transfer. *Focus,* 10, 5–7.

Frohman, M. A., Dush, M. K. and Martin, G. R. (1988) Rapid production of full-length cDNAs from rare transcripts: amplification using a single gene-specific oligonucleotide primer. *Proc. Natl. Acad Sci USA,* 85, 8998–9002.

Guo, H., Yang, H., Mockler, T. C. and Lin, C. (1998) Regulation of flowering time by *Arabidopsis* photoreceptors. *Science,* 279, 1360–1363.

Hicks, K. A., Millar, A. J., Carre, I. A., Somers, D. E., Straume, M., Meeks Wagner, D. R. and Kay, S. A. (1996) Conditional circadian dysfunction of the *Arabidopsis* early-flowering 3 mutant. *Science,* 274, 790–792.

Hiei, Y., Ohta, S., Komari, T. and Kumashiro, T. (1994). Efficient transformation of rice (*Oryza sativa* L.) mediated by *Agrocbacterium* and sequence analysis of the boundaries of the T-DNA. Plant J. 6:271–282.

Hollis, C. A. (1999) Characterising GIGANTEA; an *Arabidopsis* gene that regulates flowering-time. University of Auckland.

Holsters, M., de Waele, D., Depicker, A., Messens, E., Van Montagu, M., and Schell, J. (1978) Transfection and transformation of *A. tumefaciens. Molecular and General Genetics* 163:181–187.

Johnson, E., Bradley, M., Harberd, N. P. and Whitelam, G. C. (1994) Photoresponses of light-grown phyA mutants of *Arabidopsis*:: Phytochrome A is required for the perception of daylength extensions. *Plant Physiol.,* 105, 141–149.

Kazan, K., Curtis, M. D., Goulter, K. C., Manners, J. M. (1997). *Agrobacterium tumefaciens*—mediated transformation of double haploid canola (*Brassica napus*) lines. Aust. *J. Plant Physiol.* 24:97–102.

Kieber, J. J., Rothenberg, M., Roman, G., Feldmann, K. A. and Ecker, J. R. (1993) CTR1, a negative regulator of the ethylene response pathway in *Arabidopsis*, encodes a member of the Raf family of protein kinases. *Cell,* 72, 427–441.

Koncz, C. and Schell, J. (1986). The promoter of T-L DNA Gene 5 controls the tissue-specific expression of chimeric genes carried by a novel type of Agrobacterium binary vector. *Molecular and General Genetics* 204:383–396.

Koornneef, M., Alonso-Blanco, C., Blankestijn-de Vries, H., Hanhare, C. J. and Peeters, A. J. M. (1998b) Genetic interactions among late-flowering mutants of *Arabidopsis. Genetics,* 148.

Koornneef, M., Alonso-Blanco, C., Peeters, A. J. M. and Soppe, W. (1998a) Genetic control of flowering time in *Arabidopsis. Annu. Rev. Plant Physiol. Plant Mol. Biol.,* 49, 345–370.

Koornneef, M., Hanhart, C. J. and van der Veen, J. H. (1991). A genetic and physiological analysis of late flowering mutants in *Arabidopsis thaliana. Molecular and General Genetics* 229:57–66.

Kurepa, J., Smalle, J., Van Montagu, M. and Inez, D. (1998) Oxidative stress tolerance and longevity in *Arabidopsis*: the late-flowering mutant gigantea is tolerant to paraquat. *Plant J.,* 14, 759–764.

Levy, Y. L. and Dean, C. (1998) The transition to flowering. *Plant Cell,* 10, 1973–1990.

Lin, C., Ahmad, M., Chan, A. R. and Cashmore, A. R. (1996) CRY2: a second member of the *Arabidopsis* cryptochrome family. *Plant Physiol.,* 110, 1047-.

Logemann, J., Schell, J and Willmitzer, L. (1987). Improved method for isolation of RNA from plant tissues. *Anal. Biochem.* 141, 329–336.

Long, D., Martin, M., Sundber, E., Swinburne, J., Puangsomlee, P. and Coupland, G. (1993) The maize transposable element system Ac/Ds as a mutagen in *arabidopsis*: Identification of an albino mutation induced by Ds insertion. *Proc. Natl. Acad Sci. USA* 90:10370–10374.

Medford, J. I. (1992). Vegetative Apical Meristens. *Plant Cell* 4, 1029–1039.

Medford et al., (1991). *Plant Cell* 3, 359–370.

Medford, J. I., Behringer, F. J., Callos, J. D., Feldmann, K. A. Normal and abnormal development in the *Arabidopsis* vegetative shoot apex. *Plant Cell* 4 (6) (1992) 631–543.

Millar, A. J. and Kay, S. A. (1996) Integration of circadian and phototransduction pathways in the network controlling CAB transcription in *Arabidopsis. Proc. Natl. Acad Sci. USA,* 93, 15491–15496.

Nakai, K. and Kanehisa, M. (1992) A knowledge base for predicting protein localisation sites in eukaryotic cells. *Genomics*, 14.

Napoli et al, (1990). The Plant Cell 2, 279–289.

Newman, T., Bruijin, F. J. d., Green, P., Keegstra, K., Kende, H., McIntosh, L., Ohlrogge, J., Raikhel, N., Somerville, S., Thomashow, M., Retzel, E. and Somerville, C. (1994) A summary of methods for accessing results from large-scale partial sequencing of anonymous *Arabidopsis* cDNAs. Plant Physiol., 106, 1241–1255.

Nilsson, O., Lee, I., Blázquez, M. A. and Weigel, D. (1998) Flowering-time genes modulate the response to LEAFY activity. *Genetics*, 150, 403–410.

Piñeiro, M. and Coupland, G. (1998) The control of flowering time and floral identity in *Arabidopsis*. *Plant Physiol.*, 36, 517–568.

Putterill, J., Robson, F., Lee, K., Simon, R. and Coupland, G. (1995) The CONSTANS gene of *Arabidopsis* promotes flowering and encodes a protein showing similarities to zinc finger transcription factors. *Cell*, 80, 847–857.

Rédei, G. P. (1962) Supervital mutants of *Arabidopsis*. *Genetics*, 47, 443–460.

Richardson, K., Fowler, S., Pullen, C., Skelton, C., Morris, B. and Putterill, J. (1998) T-DNA tagging of a flowering-time gene and improved gene transfer by in planta transformation of *Arabidopsis*. *Aust. J. Plant Physiol.*, 25, 125–130.

Rothstein et al., (1987) *Proc Natl. Acad. Sci. USA* 84:8439–8443.

Sambrook et al., (1989) *Molecular Cloning: A Laboratory Manual.* (Cold Spring Harbour, N. Y.: Cold Spring Harbour Laboratory).

Sanger, F., Nicklen, S. and Coulsen, A. R (1977). DNA sequencing with chain terminating ihibitors. Proc. Natl. Acad. Sci USA. 74:5463–5467.

Saunders, D. S. (1977) *An Introduction to Biological Rhythms*. Blackie and Son Limited, Glasgow and London.

Schaffer, R. (1997) LHY, a gene that regulates flowering and hypocotyl elongation of *Arabidopsis*. PhD thesis . University of East Anglia.

Schaffer, R., Ramsay, N., Samach, A., Corden, S., Putterill, J., Carré, I. and Coupland, G. (1998) The late elongated hypocotyl mutation of *Arabidopsis* disrupts circadian rhythms and the photoperiodic control of flowering. *Cell*, 93, 1219–1229.

Simon, R., Igeno, M. I. and Coupland, G. (1996) Activation of floral meristem identity genes in *Arabidopsis*. *Nature*, 384, 59–62.

Smith et al., (1988) *Nature* 334:724–726.

Somers, D. E., Webb, A. A. R., Pearson, M. and Kay, S. A. (1998) The short-period mutant, toc1-1, alters circadian clock regulation of multiple outputs throughout development in *Arabidopsis thaliana*. *Development*, 125, 485–494.

Southern, E. M. (1975). Detection of specific sequences among DNA fragments separated by gel electorphoresis. J. Mol. Biol. 98:503–517.

Stiekema, W. J., Heidekamp, F., Dirkse, W. G., van Beckum, J., de Haan, P., Ten Bosch, C. and Louwerse, J. D. (1998) Molecular cloning and analysis of four potato tuber mRNAs. *Plant Mol. Biol.*, 11, 255–269.

Terryn, N., Neyt, P., De Clereq, R., De Keyser, A., Van Den Daele, H., Ardiles, W., Déhais, P., Rouzé, P., Gielen, J., Villarroel, R. and Montafu, M. V. (1997) Sequence analysis of a 24-kb contiguous genomic region at the *Arabidopsis thaliana* PFL locus on chromosome 1. *FEBS Let*, 416, 156–160.

van der Krol et al., (1990) *The Plant Cell* 2:291–299.

Vincent, J. (1985) A manual for the practical study of root nodule bacteria. *ISP Handbook No.* 15.

Von Heijne, G. (1992) Membrane protein structure prediction, hydrophobicity analysis and the positive-inside rule. *J. Mol. Biol.*, 225.

Voytas, D. F., Konieczny, A., Cummings, M. P. and Ausubel, F. M. (1990) The structure, distribution and evolution of the Ta1 retrotransposable element family of *Arabidopsis thaliana Genetics*, 126, 713–722.

Wang, Z. Y. and Tobin, E. M. (1998) Constitutive expression of the CIRCADIAN CLOCK ASSOCIATED (CCA1) gene disrupts circadian rhythms and suppresses its own expression. *Cell*, 93, 1–20.

Weigel et al., (1992) *Cell* 69:843–859.

Weller, J. L., Reid, J. B., Taylor, S. A. and Murfet, I. C. (1997) The genetic control of flowering in pea. *Trend Plant Sci.*, 2, 412–418.

Zagotta, X. T., Hicks, K. A., Jacobs, C., Young, J. C., Harngarter, R. P. and Meeks Wagner, D. R. (1996) The *Arabidopsis* ELF3 gene regulates vegetative photomorphogenesis and the photoperiodic induction of flowering. *Plant J.*, 10, 691–702.

Zhang et al., (1992) *The Plant Cell* 4:1575–1588.

---

What we claim is:

1. An isolated polynucleotide selected from the group consisting of:
   (a) a polynucleotide consisting essentially of a nucleotide sequence that is at least 95% sequence identical, as determined by the BLAST algorithm under default parameters, to the full length sequence of SEQ ID NO: 5; wherein the polynucleotide encodes a polypeptide having GI function;
   (b) a polynucleotide consisting essentially of a sequence encoding the polypeptide of SEQ ID NO:6; and
   (c) SEQ ID NO: 5; and
   (d) a polynucleotide which is complimentary to the polynucleotide of (a), (b), or (c).

2. A recombinant expression cassette, comprising the polynucleotide of claim 1, wherein the polynucleotide is operably linked, in sense or anti-sense orientation, to a promoter.

3. A bacterial or plant host cell comprising the expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut and cocoa.

8. A transgenic seed from the transgenic plant of claim 4.

9. A method of promoting flowering of a plant, comprising:

a) introducing into a plant cell of said plant a recombinant expression cassette comprising the polynucleotide of claim 1 operably linked to a promoter and b) culturing the plant and expressing said polynucleotide; wherein the flowering time in said plant is promoted.

10. A method of promoting flowering of a plant, comprising:

a) introducing into a plant cell of said plant a recombinant expression cassette comprising the polynucleotide of claim 1 operably linked to a promoter;

b) culturing the plant cell under plant cell growing conditions; and c) regenerating a plant from said plant cell; and expressing said polynucleotide, wherein the flowering time in said plant is promoted.

* * * * *

SEQUENCE LISTING

```
<160> NUMBER OF SEQ ID NOS: 43

<210> SEQ ID NO 1
<211> LENGTH: 335
<212> TYPE: DNA
<213> ORGANISM: Arabidopsis sp.
<220> FEATURE:
<221> NAME/KEY: misc_feature
<222> LOCATION: (162)..(162)
<223> OTHER INFORMATION: Unsure (n = a, g, c, or t)
<220> FEATURE:
<221> NAME/KEY: misc_feature
<222> LOCATION: (183)..(183)
<223> OTHER INFORMATION: Unsure (n = a, g, c, or t)
<220> FEATURE:
<221> NAME/KEY: misc_feature
<222> LOCATION: (191)..(191)
<223> OTHER INFORMATION: Unsure (n = a, g, c, or t)
```

```
<220> FEATURE:
<221> NAME/KEY: misc_feature
<222> LOCATION: (198)..(198)
<223> OTHER INFORMATION: Unsure (n = a, g, c, or t)
<220> FEATURE:
<221> NAME/KEY: misc_feature
<222> LOCATION: (220)..(220)
<223> OTHER INFORMATION: Unsure (n = a, g, c, or t)
<220> FEATURE:
<221> NAME/KEY: misc_feature
<222> LOCATION: (222)..(222)
<223> OTHER INFORMATION: Unsure (n = a, g, c, or t)
<220> FEATURE:
<221> NAME/KEY: misc_feature
<222> LOCATION: (266)..(266)
<223> OTHER INFORMATION: Unsure (n = a, g, c, or t)
<220> FEATURE:
<221> NAME/KEY: misc_feature
<222> LOCATION: (278)..(278)
<223> OTHER INFORMATION: Unsure (n = a, g, c, or t)
<220> FEATURE:
<221> NAME/KEY: misc_feature
<222> LOCATION: (282)..(282)
<223> OTHER INFORMATION: Unsure (n = a, g, c, or t)
<220> FEATURE:
<221> NAME/KEY: misc_feature
<222> LOCATION: (307)..(307)
<223> OTHER INFORMATION: Unsure (n = a, g, c, or t)
<220> FEATURE:
<221> NAME/KEY: misc_feature
<222> LOCATION: (319)..(319)
<223> OTHER INFORMATION: Unsure (n = a, g, c, or t)
<220> FEATURE:
<221> NAME/KEY: misc_feature
<222> LOCATION: (329)..(329)
<223> OTHER INFORMATION: Unsure (n = a, g, c, or t)

<400> SEQUENCE: 1
ggacctgtgg cagcatttga ttcatacgtt cttgctgctg tttgtgctct tgcctgtgag      60
gttcagctgt atcctatgat ctctggtggg gggaactttt ccaattctgc cgtggctgga     120
actattacaa agcctgtaaa gataaatggg tcatctaaag antatggagc tgggattgac     180
tcngcaatta ntcatacncg ccgaattttg gcaatcctan angcactctt ttcattaaaa     240
ccatcttctg tggggactcc atgganttac agttctantg anataattgc tgcggccatg     300
gttgcanctc atatttccna actgttcana cattc                                335

<210> SEQ ID NO 2
<211> LENGTH: 432
<212> TYPE: DNA
<213> ORGANISM: Arabidopsis sp.

<400> SEQUENCE: 2
catcaaagta actccaaaac tgccaaacaa acagagaaga acgggaatga atagtcctcc      60
tatcggattc tttcaaacgc cgcctcaata gaactgggaa agccgatatc caaaactgtt     120
taaactgggg aagctcaaca gcttgcttcc aacaactatg cctaactcag ttttgacac      180 tgcggctcgg ggaatcggct gtactatatc cttgtcccaa taacgagcac ccactttgt      240 ttttggtaaa tttagttttt agacaaaaca tttggacgta gaccaagaag aatatatata     300
tagtttgttg tatgtaatgt tgtaatgatg agtgactgac gcaatcactc ccaccggcgt     360
tggatttgct ctcgctcggt gtcttatata actcaacctc tttctgtaca ttttaaatga     420
cgaagtagct ca                                                         432

<210> SEQ ID NO 3
<211> LENGTH: 5400
<212> TYPE: DNA
```

<213> ORGANISM: Arabidopsis sp.

<400> SEQUENCE: 3

| | | | | |
|---|---|---|---|---|
| tctcgattga | tagtagaaga | aaggtgttag | ttagattgtt | cgttcatcta | gttggggttt | 60 |
| agtttcggtt | cctggatggc | tagttcatct | tcatctgaga | gatggatcga | tggtcttcag | 120 |
| ttctcttcct | tgttatggcc | tccgccacga | gatcctcaac | aacataagga | tcaagtcgtt | 180 |
| gcttatgttg | aatattttgg | tcaatttaca | tcagagcaat | tcccagatga | cattgctgag | 240 |
| gtacttgata | cctaatgagt | ttaataagag | tattctctta | gtagtgacgt | tttgattcat | 300 |
| gtataattta | tctgtatcag | ttggtccggc | atcagtatcc | atcaactgag | aagcgacttt | 360 |
| tagacgatgt | gctgggtatg | atcaacattt | atgatccaca | cttctctttt | tgtgtgtgaa | 420 |
| tgtctatctg | attttcgttt | tctgatgaaa | cagcgatgtt | tgtccttcat | catccggagc | 480 |
| atggtcatgc | agtcattctt | ccaatcattt | catgtcttat | tgatggctcg | ttggtgtaca | 540 |
| gcaaggaagc | tcatccgttt | gcctctttca | tatctttagt | ttgcccaagt | agtgaggtat | 600 |
| ataatagctg | tctagtatca | tgcttactga | tttggtgtaa | cctataccat | tttgtgctaa | 660 |
| catgttcact | atcctaacag | aatgactatt | cggagcaatg | ggctttggca | tgtggagaaa | 720 |
| tccttcgcat | tttgactcat | tacaaccgtc | ccatttataa | aactgagcag | caaaatggag | 780 |
| atacagagag | aaattgtctg | agcaaagcta | caactagtgg | ttctccgact | tcagagccta | 840 |
| aggctggatc | accaacacag | catgaaagga | aacctttaag | gcctttgtct | ccatggatca | 900 |
| gtgatatact | acttgctgct | cctcttggta | taagaagtga | ctatttccga | tggtaagtag | 960 |
| actctgttac | tgatgcttct | atgtgttcat | gcgccggcct | ccttctttta | ttttggtctc | 1020 |
| tctgctgagg | tctatgtatt | gaggttctgt | agtggattaa | gcttactgac | aactaaaaat | 1080 |
| gttgcttatt | atttacaggt | gtagtggtgt | aatgggtaaa | tatgctgctg | agagctcaa | 1140 |
| gccgccaacc | attggtgagt | tcaagaattc | catgttaata | tcccctggaa | ctggattttg | 1200 |
| atgataattc | tgatcaatag | agttgttcta | tcacttcgtt | cataaatgtg | tatccatcac | 1260 |
| ctgtggctat | agaatgtgtt | ttgagttgct | tcctataact | ttcatgttgt | cctactttgg | 1320 |
| cagcttctcg | aggatctggt | aaacatcctc | aactgatgcc | ttcaaccccca | agatgggctg | 1380 |
| ttgctaatgg | agctggtgtc | atactgagtg | tttgtgatga | tgaagttgct | cgatatgaga | 1440 |
| ctgctacgct | gacagcggtc | gctgtccctg | cacttcttct | tcctccgcca | acgacatcct | 1500 |
| tagatgagca | tctagttgct | ggccttccag | ctcttgaacc | atatgcacgt | ttgtttcata | 1560 |
| ggtattgttt | ctgggcttac | cctttcaatt | agggtttatt | ggtagtagtc | tgttgctagt | 1620 |
| tttaaggttg | tgcttcctcg | aatccctaga | tcagaattgt | tttctcactt | tcctgttata | 1680 |
| ctgtcagata | ctatgccatt | gcaactccaa | gtgctacgca | gagacttctt | cttggactct | 1740 |
| tagaagcacc | accgtcgtgg | gctccagatg | cacttgatgc | tgctgtacag | cttgtggaac | 1800 |
| tccttcgagc | tgctgaagat | tatgcatctg | gtgtaaggga | aagcgtaata | tgaatctctt | 1860 |
| aattaccctc | cagaaagcta | attgtgtccc | ttgttataaa | aaagtcagc | tttggtatgt | 1920 |
| catcaaagaa | atcagctttg | atcacattct | tttcttggt | gcagctaccc | aggaactgga | 1980 |
| tgcatttgca | cttcttgcgg | gctataggaa | ttgctatgtc | tatgagggca | ggtgttgctg | 2040 |
| ctgatgctgc | agccgctttg | cttttccgca | tactctcaca | gccggcactg | cttttttcctc | 2100 |
| cgctaagtca | agttgaggga | gtagaaattc | agcacgcgcc | tattggtggc | tacagttcaa | 2160 |
| attacagaaa | acaggcatgg | ttcctctttta | tatttttctg | ctattccatc | tctgatatgc | 2220 |
| gattggcatt | ctactagaaa | attatattga | aactgactca | tttcatctca | acagatagaa | 2280 |

-continued

```
gttcctgcag cagaagcaac cattgaagcc actgcccaag gaattgcctc aatgctttgt    2340
gctcatggtc ctgaagttga gtggagaatt tgcactatat gggaagctgc ttatggtttg    2400
atccctttaa attcttcggc ggttgatctt cccgaaatca tagttgctac cccactgcaa    2460
cctcctatct tgtcatggaa tttatacatt ccactcctca aagtacttga atatcttcca    2520
cgggggagtc cttcggaagc atgcttgatg aaaatatttg ttgccactgt ggaaacaata    2580
ctcagtagaa cttttccgcc tgaatcttcc agggaactaa ccagaaaagc tagatcgagt    2640
tttaccacaa gatcagcgac caaaaatctt gctatgtctg agcttcgtgc tatggtccat    2700
gctctctttt tagaatcatg cgctggtgtg aattagctt cacgcctact ttttgttgtg    2760
ttgactgtat gtgttagcca tgaagcacag tctagtggta gcaagagacc gagaagtgaa    2820
tatgctagta ctactgaaaa tattgaggcg aatcaacctg tatctaacaa tcaaactgct    2880
aaccgtaaaa gtaggaatgt caagggacag ggacctgtgg cagcatttga ttcatacgtt    2940
cttgctgctg tttgtgctct tgcctgtgag gttcagctgt atcctatgat ctctggtggg    3000
gggaacttt ccaattctgc cgtggctgga actattacaa agcctgtaaa gataaatggg    3060
tcatctaaag agtatggagc tgggattgac tcggcaatta gtcatacgcg ccgaattttg    3120
gcaatcctag aggcactctt ttcattaaaa ccatcttctg tggggactcc atggagttac    3180
agttctagtg agatagttgc tgcggccatg gttgcagctc atatttccga actgttcaga    3240
cgttcaaagg ccttgacgca tgcattgtct gggttgatga gatgtaagtg ggataaggaa    3300
attcataaaa gagcatcatc attatataac ctcatagatg ttcacagcaa agttgttgcc    3360
tccattgttg acaaagctga acccttggaa gcctaccta agaatacacc ggttcagaag    3420
gattctgtga cctgttaaa ctggaaacaa gagaacacat gtgcaagcac cacatgcttt    3480
gatacagcgg tgacatccgc ctcaaggact gaaatgaatc caagaggaaa ccataagtat    3540
gctagacatt cagatgaagg ctcagggaga ccctcagaga agggtatcaa agatttcctc    3600
ttggatgctt ctgatcttgc gaatttcctc acagctgata gactcgcagg gttctattgt    3660
ggtacacaaa agcttttgag gtcagtgctt cagagaaac cggagctgtc tttctccgtt    3720
gtttcactgt tatggcacaa actgattgct gctcctgaaa tccagcccac cgcagaaagc    3780
acctctgcgc aacaaggatg gagacaggta aacctcagca cttctatttc ccagctcgct    3840
tacagtttcc ttggtagttc tttactaatc caattaagtc gctcgacttc atacactgat    3900
catatttttt atatatcagg ttgttgatgc gctatgcaat gtcgtatctg caacgccagc    3960
gaaagcagca gcagcagttg tccttcaggt ccaaattact ctttgacttt ttatttcatt    4020
tgtcaggaat gcaacacctg tgtaaagatt aaactgcgga aaacctatgg cctgtgttaa    4080
tgttttataa tgcttggttc actcattttga tctctcatga atttataaaa attaagcttg    4140
gaatttatat gcaacacttg ttttaatatg ccaaggatag gaaataagga agaaaaaatc    4200
tgtgtaaaat aatggcttgt ttcaagctca tatgttgaag gatttactct aatgctctat    4260
tgtctgaaat ggtcttgtgt tatttacagg ctgaaaggga gttgcagcct tggatcgcca    4320
aagatgatga agaaggccaa aaaatgtgga aaatcaacca acggatagtc aaagtgttgg    4380
tggaactcat gcgcaatcat gacaggcctg agtcactggt gattctcgca agtgcatcag    4440
atcttcttct gcgggcaact gatggaatgc ttgttgatgg agaagcttgt acattacctc    4500
aacttgaggt actgcactgt tatagattgc tcttcaatgc ccttcttcgg gctagagtaa    4560
taatcatttt ctgattccac tgtatttaa acttttgcag ctacttgaag ccacggcaag    4620
```

-continued

```
agcaatacag ccggtgctag cttgggggcc atctggacta gcagtggtcg acggtttatc    4680
caatctattg aaggtaaaag cagaatcgaa cagagcctat ggtttcctgc gtcgattgta    4740
gatgatcagt agtaggtcca gttaccaaag tgcttaacct tgttcacatc tttttgcttc    4800
tatgcagtgt cgtctaccag caacaatacg gtgcctttca cacccaagtg cacacgtacg    4860
tgccttaagc acgtcagtac tacgtgatat catgaaccaa agctccatac ccatcaaagt    4920
aactccaaaa ctgccaacaa cagagaagaa cggaatgaat agtccgtcct atcgattctt    4980
caacgccgcc tcaatagact ggaaagccga tatccaaaac tgtttaaact gggaagctca    5040
cagcttgctc tccacaacta tgcctactca gtttctcgac actgcggctc gggaactcgg    5100
ctgtactata tccttgtccc aataacgagc acccactttt gttttggta aattttagtt     5160 ctctagacaa acatttgga cgtagaccaa gaagaatata tatatagttt gttgtatgta     5220
atgttgtaat gatgagtgac tgacgcaatc actcccaccg gcgttggatt tgctctcgct    5280
cggtgtctta tataactcaa cctcttctct gtacatttta aatgacgaag tagctcaatc    5340
tttttttttg tgcgtctggt gtttagtctt cagtggattc taaatcgtaa tgtatagaag    5400
```

<210> SEQ ID NO 4
<211> LENGTH: 1167
<212> TYPE: PRT
<213> ORGANISM: Arabidopsis sp.

<400> SEQUENCE: 4

```
Met Ala Ser Ser Ser Ser Glu Arg Trp Ile Asp Gly Leu Gln Phe
1               5                   10                  15

Ser Ser Leu Leu Trp Pro Pro Arg Asp Pro Gln Gln His Lys Asp
                20                  25                  30

Gln Val Val Ala Tyr Val Glu Tyr Phe Gly Gln Phe Thr Ser Glu Gln
            35                  40                  45

Phe Pro Asp Asp Ile Ala Glu Leu Val Arg His Gln Tyr Pro Ser Thr
50                  55                  60

Glu Lys Arg Leu Leu Asp Asp Val Leu Ala Met Phe Val Leu His His
65                  70                  75                  80

Pro Glu His Gly His Ala Val Ile Leu Pro Ile Ile Ser Cys Leu Ile
                85                  90                  95

Asp Gly Ser Leu Val Tyr Ser Lys Glu Ala His Pro Phe Ala Ser Phe
            100                 105                 110

Ile Ser Leu Val Cys Pro Ser Ser Glu Asn Asp Tyr Ser Glu Gln Trp
        115                 120                 125

Ala Leu Ala Cys Gly Glu Ile Leu Arg Ile Leu Thr His Tyr Asn Arg
    130                 135                 140

Pro Ile Tyr Lys Thr Glu Gln Gln Asn Gly Asp Thr Glu Arg Asn Cys
145                 150                 155                 160

Leu Ser Lys Ala Thr Thr Ser Gly Ser Pro Thr Ser Glu Pro Lys Ala
                165                 170                 175

Gly Ser Pro Thr Gln His Glu Arg Lys Pro Leu Arg Pro Leu Ser Pro
            180                 185                 190

Trp Ile Ser Asp Ile Leu Leu Ala Ala Pro Leu Gly Ile Arg Ser Asp
        195                 200                 205

Tyr Phe Arg Trp Cys Ser Gly Val Met Gly Lys Tyr Ala Ala Gly Glu
    210                 215                 220

Leu Lys Pro Pro Thr Ile Glu His Pro Gln Leu Met Pro Ser Thr Pro
225                 230                 235                 240
```

-continued

```
Arg Trp Ala Val Ala Asn Gly Ala Gly Val Ile Leu Ser Val Cys Asp
                245                 250                 255
Asp Glu Val Ala Arg Tyr Glu Thr Ala Thr Leu Thr Ala Val Ala Val
            260                 265                 270
Pro Ala Leu Leu Leu Pro Pro Thr Thr Ser Leu Asp Glu His Leu
        275                 280                 285
Val Ala Gly Leu Pro Ala Leu Glu Pro Tyr Ala Arg Leu Phe His Arg
    290                 295                 300
Tyr Tyr Ala Ile Ala Thr Pro Ser Ala Thr Gln Arg Leu Leu Leu Gly
305                 310                 315                 320
Leu Leu Glu Ala Pro Pro Ser Trp Ala Pro Asp Ala Leu Asp Ala Ala
                325                 330                 335
Val Gln Leu Val Glu Leu Leu Arg Ala Ala Glu Asp Tyr Ala Ser Gly
            340                 345                 350
Val Arg Leu Pro Arg Asn Trp Met His Leu His Phe Leu Arg Ala Ile
        355                 360                 365
Gly Ile Ala Met Ser Met Arg Ala Gly Val Ala Ala Asp Ala Ala Ala
    370                 375                 380
Ala Leu Leu Phe Arg Ile Leu Ser Gln Pro Ala Leu Leu Phe Pro Pro
385                 390                 395                 400
Leu Ser Gln Val Glu Gly Val Glu Ile Gln His Ala Pro Ile Gly Gly
                405                 410                 415
Tyr Ser Ser Asn Tyr Arg Arg Gln Ile Glu Val Pro Ala Ala Glu Ala
            420                 425                 430
Thr Ile Glu Ala Thr Ala Gln Gly Ile Ala Ser Met Leu Cys Ala His
        435                 440                 445
Gly Pro Glu Val Glu Trp Arg Ile Cys Thr Ile Trp Glu Ala Ala Tyr
    450                 455                 460
Gly Leu Ile Pro Leu Asn Ser Ser Ala Val Asp Leu Pro Glu Ile Ile
465                 470                 475                 480
Val Ala Thr Pro Leu Gln Pro Pro Ile Leu Ser Trp Asn Leu Tyr Ile
                485                 490                 495
Pro Leu Leu Lys Val Leu Glu Tyr Leu Pro Arg Gly Ser Pro Ser Glu
            500                 505                 510
Ala Cys Leu Met Lys Ile Phe Val Ala Thr Val Glu Thr Ile Leu Ser
        515                 520                 525
Arg Thr Phe Pro Pro Glu Ser Ser Arg Glu Leu Thr Arg Lys Ala Arg
    530                 535                 540
Ser Ser Phe Thr Thr Arg Ser Ala Thr Lys Asn Leu Ala Met Ser Glu
545                 550                 555                 560
Leu Arg Ala Met Val His Ala Leu Phe Leu Glu Ser Cys Ala Gly Val
                565                 570                 575
Glu Leu Ala Ser Arg Leu Leu Phe Val Val Leu Thr Val Cys Val Ser
            580                 585                 590
His Glu Ala Gln Ser Ser Gly Ser Lys Arg Pro Arg Ser Glu Tyr Ala
        595                 600                 605
Ser Thr Thr Glu Asn Ile Glu Ala Asn Gln Pro Val Ser Asn Asn Gln
    610                 615                 620
Thr Ala Asn Arg Lys Ser Arg Asn Val Lys Gly Gln Gly Pro Val Ala
625                 630                 635                 640
Ala Phe Asp Ser Tyr Val Leu Ala Ala Val Cys Ala Leu Ala Cys Glu
                645                 650                 655
Val Gln Leu Tyr Pro Met Ile Ser Gly Gly Gly Asn Phe Ser Asn Ser
```

-continued

```
                660                 665                 670
Ala Val Ala Gly Thr Ile Thr Lys Pro Val Lys Ile Asn Gly Ser Ser
            675                 680                 685
Lys Glu Tyr Gly Ala Gly Ile Asp Ser Ala Ile Ser His Thr Arg Arg
            690                 695                 700
Ile Leu Ala Ile Leu Glu Ala Leu Phe Ser Leu Lys Pro Ser Ser Val
705                 710                 715                 720
Gly Thr Pro Trp Ser Tyr Ser Ser Glu Ile Val Ala Ala Met
                    725                 730                 735
Val Ala Ala His Ile Ser Glu Leu Phe Arg Arg Ser Lys Ala Leu Thr
            740                 745                 750
His Ala Leu Ser Gly Leu Met Arg Cys Lys Trp Asp Lys Glu Ile His
            755                 760                 765
Lys Arg Ala Ser Ser Leu Tyr Asn Leu Ile Asp Val His Ser Lys Val
            770                 775                 780
Val Ala Ser Ile Val Asp Lys Ala Glu Pro Leu Glu Ala Tyr Leu Lys
785                 790                 795                 800
Asn Thr Pro Val Gln Lys Asp Ser Val Thr Cys Leu Asn Trp Lys Gln
                    805                 810                 815
Glu Asn Thr Cys Ala Ser Thr Thr Cys Phe Asp Thr Ala Val Thr Ser
            820                 825                 830
Ala Ser Arg Thr Glu Met Asn Pro Arg Gly Asn His Lys Tyr Ala Arg
            835                 840                 845
His Ser Asp Glu Gly Ser Gly Arg Pro Ser Glu Lys Gly Ile Lys Asp
            850                 855                 860
Phe Leu Leu Asp Ala Ser Asp Leu Ala Asn Phe Leu Thr Ala Asp Arg
865                 870                 875                 880
Leu Ala Gly Phe Tyr Cys Gly Thr Gln Lys Leu Leu Arg Ser Val Leu
                    885                 890                 895
Ala Glu Lys Pro Glu Leu Ser Phe Ser Val Val Ser Leu Leu Trp His
            900                 905                 910
Lys Leu Ile Ala Ala Pro Glu Ile Gln Pro Thr Ala Glu Ser Thr Ser
            915                 920                 925
Ala Gln Gln Gly Trp Arg Gln Val Val Asp Ala Leu Cys Asn Val Val
            930                 935                 940
Ser Ala Thr Pro Ala Lys Ala Ala Ala Val Val Leu Gln Ala Glu
945                 950                 955                 960
Arg Glu Leu Gln Pro Trp Ile Ala Lys Asp Asp Glu Glu Gly Gln Lys
                    965                 970                 975
Met Trp Lys Ile Asn Gln Arg Ile Val Lys Val Leu Val Glu Leu Met
            980                 985                 990
Arg Asn His Asp Arg Pro Glu Ser Leu Val Ile Leu Ala Ser Ala Ser
            995                 1000                1005
Asp Leu Leu Leu Arg Ala Thr Asp Gly Met Leu Val Asp Gly Glu
            1010                1015                1020
Ala Cys Thr Leu Pro Gln Leu Glu Leu Leu Glu Ala Thr Ala Arg
            1025                1030                1035
Ala Ile Gln Pro Val Leu Ala Trp Gly Pro Ser Gly Leu Ala Val
            1040                1045                1050
Val Asp Gly Leu Ser Asn Leu Leu Lys Cys Arg Leu Pro Ala Thr
            1055                1060                1065
Ile Arg Cys Leu Ser His Pro Ser Ala His Val Arg Ala Leu Ser
            1070                1075                1080
```

-continued

```
Thr Ser Val Leu Arg Asp Ile Met Asn Gln Ser Ser Ile Pro Ile
    1085                1090                1095

Lys Val Thr Pro Lys Leu Pro Thr Thr Glu Lys Asn Gly Met Asn
    1100                1105                1110

Ser Pro Ser Tyr Arg Phe Phe Asn Ala Ala Ser Ile Asp Trp Lys
    1115                1120                1125

Ala Asp Ile Gln Asn Cys Leu Asn Trp Glu Ala His Ser Leu Leu
    1130                1135                1140

Ser Thr Thr Met Pro Thr Gln Phe Leu Asp Thr Ala Ala Arg Glu
    1145                1150                1155

Leu Gly Cys Thr Ile Ser Leu Ser Gln
    1160                1165
```

<210> SEQ ID NO 5
<211> LENGTH: 3522
<212> TYPE: DNA
<213> ORGANISM: Arabidopsis sp.

<400> SEQUENCE: 5

| | |
|---|---|
| atggctagtt catcttcatc tgagagatgg atcgatggtc ttcagttctc ttccttgtta | 60 |
| tggcctccgc cacgagatcc tcaacaacat aaggatcaag tcgttgctta tgttgaatat | 120 |
| tttggtcaat ttacatcaga gcaattccca gatgacattg ctgagttggt ccggcatcag | 180 |
| tatccatcaa ctgagaagcg acttttagac gatgtgctgg cgatgtttgt ccttcatcat | 240 |
| ccggagcatg gtcatgcagt cattcttcca atcatttcat gtcttattga tggctcgttg | 300 |
| gtgtacagca aggaagctca tccgtttgcc tctttcatat ctttagtttg cccaagtagt | 360 |
| gagaatgact attcggagca atgggctttg catgtggag aaatccttcg cattttgact | 420 |
| cattacaacc gtcccatttta taaaactgag cagcaaaatg agatacaga gagaaattgt | 480 |
| ctgagcaaag ctacaactag tggttctccg acttcagagc ctaaggctgg atcaccaaca | 540 |
| cagcatgaaa ggaaaccttt aaggcctttg tctccatgga tcagtgatat actacttgct | 600 |
| gctcctcttg gtataagaag tgactatttc cgatggtgta gtggtgtaat gggtaaaatat | 660 |
| gctgctggag agctcaagcc gccaaccatt gcttctcgag atctggtaa acatcctcaa | 720 |
| ctgatgcctt caaccccaag atgggctgtt gctaatggag ctggtgtcat actgagtgtt | 780 |
| tgtgatgatg aagttgctcg atatgagact gctacgctga cagcggtcgc tgtccctgca | 840 |
| cttcttcttc ctccgccaac gacatcctta gatgagcatc tagttgctgg ccttccagct | 900 |
| cttgaaccat atgcacgttt gtttcataga tactatgcca ttgcaactcc aagtgctacg | 960 |
| cagagacttc ttcttggact cttagaagca ccaccgtcgt gggctccaga tgcacttgat | 1020 |
| gctgctgtac agcttgtgga actccttcga gctgctgaag attatgcatc tggtgtaagg | 1080 |
| ctacccagga actggatgca tttgcacttc ttgcgggcta taggaattgc tatgtctatg | 1140 |
| agggcaggtg ttgctgctga tgctgcagcc gctttgcttt tccgcatact ctcacagccg | 1200 |
| gcactgcttt ttcctccgct aagtcaagtt gagggagtag aaattcagca cgcgcctatt | 1260 |
| ggtggctaca gttcaaatta cagaaaacag atagaagttc ctgcagcaga agcaaccatt | 1320 |
| gaagccactg cccaaggaat tgcctcaatg cttgtgctc atggtcctga agttgagtgg | 1380 |
| agaatttgca ctatatggga agctgcttat ggtttgatcc ctttaaattc ttcggcggtt | 1440 |
| gatcttcccg aaatcatagt tgctacccca ctgcaacctc ctatcttgtc atggaattta | 1500 |
| tacattccac tcctcaaagt acttgaatat cttccacggg ggagtccttc ggaagcatgc | 1560 |

-continued

```
ttgatgaaaa tatttgttgc cactgtggaa acaatactca gtagaacttt tccgcctgaa    1620
tcttccaggg aactaaccag aaaagctaga tcgagtttta ccacaagatc agcgaccaaa    1680
aatcttgcta tgtctgagct tcgtgctatg gtccatgctc tcttttaga atcatgcgct    1740
ggtgtggaat tagcttcacg cctactttt gttgtgttga ctgtatgtgt tagccatgaa    1800
gcacagtcta gtggtagcaa gagaccgaga agtgaatatg ctagtactac tgaaaatatt    1860
gaggcgaatc aacctgtatc taacaatcaa actgctaacc gtaaaagtag gaatgtcaag    1920
ggacagggac ctgtggcagc atttgattca tacgttcttg ctgctgtttg tgctcttgcc    1980
tgtgaggttc agctgtatcc tatgatctct ggtgggggga acttttccaa ttctgccgtg    2040
gctggaacta ttacaaagcc tgtaaagata aatgggtcat ctaaagagta tggagctggg    2100
attgactcgg caattagtca tacgcgccga attttggcaa tcctagaggc actcttttca    2160
ttaaaaccat cttctgtggg gactccatgg agttacagtt ctagtgagat agttgctgcg    2220
gccatggttg cagctcatat ttccgaactg ttcagacgtt caaaggcctt gacgcatgca    2280
tgtctgggt tgatgagatg taagtgggat aaggaaattc ataaagagc atcatcatta    2340
tataacctca tagatgttca cagcaaagtt gttgcctcca ttgttgacaa agctgaaccc    2400
ttggaagcct accttaagaa tacaccggtt cagaaggatt ctgtgacctg tttaaactgg    2460
aaacaagaga acacatgtgc aagcaccaca tgctttgata cagcggtgac atccgcctca    2520
aggactgaaa tgaatccaag aggaaaccat aagtatgcta gacattcaga tgaaggctca    2580
gggagaccct cagagaaggg tatcaaagat ttcctcttgg atgcttctga tcttgcgaat    2640
tcctcacag ctgatagact cgcagggttc tattgtggta cacaaaagct tttgaggtca    2700
gtgcttgcag agaaaccgga gctgtctttc tccgttgttt cactgttatg cacaaactg    2760
attgctgctc ctgaaatcca gcccaccgca gaaagcacct ctgcgcaaca aggatggaga    2820
caggttgttg atgcgctatg caatgtcgta tctgcaacgc cagcgaaagc agcagcagca    2880
gttgtccttc aggctgaaag ggagttgcag ccttggatcg ccaaagatga tgaagaaggc    2940
caaaaaatgt ggaaaatcaa ccaacggata gtcaaagtgt tggtggaact catgcgcaat    3000
catgacaggc ctgagtcact ggtgattctc gcaagtgcat cagatcttct tctgcgggca    3060
actgatggaa tgcttgttga tggagaagct tgtacattac ctcaacttga gctacttgaa    3120
gccacggcaa gagcaataca gccggtgcta gcttggggc catctggact agcagtggtc    3180
gacggtttat ccaatctatt gaagtgtcgt ctaccagcaa caatacgtg cctttcacac    3240
ccaagtgcac acgtacgtgc cttaagcacg tcagtactac gtgatatcat gaaccaaagc    3300
tccatacca tcaaagtaac tccaaaactg ccaacaacag agaagaacgg aatgaatagt    3360
ccgtcctatc gattcttcaa cgccgcctca atagactgga aagccgatat ccaaaactgt    3420
ttaaactggg aagctcacag cttgctctcc acaactatgc ctactcagtt tctcgacact    3480
gcggctcggg aactcggctg tactatatcc ttgtcccaat aa                       3522
```

<210> SEQ ID NO 6
<211> LENGTH: 1173
<212> TYPE: PRT
<213> ORGANISM: Arabidopsis sp.

<400> SEQUENCE: 6

Met Ala Ser Ser Ser Ser Glu Arg Trp Ile Asp Gly Leu Gln Phe
1               5                   10                  15

Ser Ser Leu Leu Trp Pro Pro Arg Asp Pro Gln Gln His Lys Asp
            20                  25                  30

-continued

```
Gln Val Val Ala Tyr Val Glu Tyr Phe Gly Gln Phe Thr Ser Glu Gln
         35                  40                  45
Phe Pro Asp Asp Ile Ala Glu Leu Val Arg His Gln Tyr Pro Ser Thr
 50                  55                  60
Glu Lys Arg Leu Leu Asp Asp Val Leu Ala Met Phe Val Leu His His
 65                  70                  75                  80
Pro Glu His Gly His Ala Val Ile Leu Pro Ile Ile Ser Cys Leu Ile
                 85                  90                  95
Asp Gly Ser Leu Val Tyr Ser Lys Glu Ala His Pro Phe Ala Ser Phe
                100                 105                 110
Ile Ser Leu Val Cys Pro Ser Ser Glu Asn Asp Tyr Ser Glu Gln Trp
                115                 120                 125
Ala Leu Ala Cys Gly Glu Ile Leu Arg Ile Leu Thr His Tyr Asn Arg
                130                 135                 140
Pro Ile Tyr Lys Thr Glu Gln Gln Asn Gly Asp Thr Glu Arg Asn Cys
145                 150                 155                 160
Leu Ser Lys Ala Thr Thr Ser Gly Ser Pro Thr Ser Glu Pro Lys Ala
                165                 170                 175
Gly Ser Pro Thr Gln His Glu Arg Lys Pro Leu Arg Pro Leu Ser Pro
                180                 185                 190
Trp Ile Ser Asp Ile Leu Leu Ala Ala Pro Leu Gly Ile Arg Ser Asp
                195                 200                 205
Tyr Phe Arg Trp Cys Ser Gly Val Met Gly Lys Tyr Ala Ala Gly Glu
                210                 215                 220
Leu Lys Pro Pro Thr Ile Ala Ser Arg Gly Ser Gly Lys His Pro Gln
225                 230                 235                 240
Leu Met Pro Ser Thr Pro Arg Trp Ala Val Ala Asn Gly Ala Gly Val
                245                 250                 255
Ile Leu Ser Val Cys Asp Asp Glu Val Ala Arg Tyr Glu Thr Ala Thr
                260                 265                 270
Leu Thr Ala Val Ala Val Pro Ala Leu Leu Leu Pro Pro Pro Thr Thr
                275                 280                 285
Ser Leu Asp Glu His Leu Val Ala Gly Leu Pro Ala Leu Glu Pro Tyr
290                 295                 300
Ala Arg Leu Phe His Arg Tyr Tyr Ala Ile Ala Thr Pro Ser Ala Thr
305                 310                 315                 320
Gln Arg Leu Leu Leu Gly Leu Leu Glu Ala Pro Pro Ser Trp Ala Pro
                325                 330                 335
Asp Ala Leu Asp Ala Ala Val Gln Leu Val Glu Leu Leu Arg Ala Ala
                340                 345                 350
Glu Asp Tyr Ala Ser Gly Val Arg Leu Pro Arg Asn Trp Met His Leu
                355                 360                 365
His Phe Leu Arg Ala Ile Gly Ile Ala Met Ser Met Arg Ala Gly Val
                370                 375                 380
Ala Ala Asp Ala Ala Ala Leu Leu Phe Arg Ile Leu Ser Gln Pro
385                 390                 395                 400
Ala Leu Leu Phe Pro Pro Leu Ser Gln Val Glu Gly Val Glu Ile Gln
                405                 410                 415
His Ala Pro Ile Gly Gly Tyr Ser Ser Asn Tyr Arg Lys Gln Ile Glu
                420                 425                 430
Val Pro Ala Ala Glu Ala Thr Ile Glu Ala Thr Ala Gln Gly Ile Ala
                435                 440                 445
```

```
Ser Met Leu Cys Ala His Gly Pro Glu Val Glu Trp Arg Ile Cys Thr
    450                 455                 460
Ile Trp Glu Ala Ala Tyr Gly Leu Ile Pro Leu Asn Ser Ser Ala Val
465                 470                 475                 480
Asp Leu Pro Glu Ile Ile Val Ala Thr Pro Leu Gln Pro Pro Ile Leu
                    485                 490                 495
Ser Trp Asn Leu Tyr Ile Pro Leu Leu Lys Val Leu Glu Tyr Leu Pro
            500                 505                 510
Arg Gly Ser Pro Ser Glu Ala Cys Leu Met Lys Ile Phe Val Ala Thr
        515                 520                 525
Val Glu Thr Ile Leu Ser Arg Thr Phe Pro Pro Glu Ser Ser Arg Glu
    530                 535                 540
Leu Thr Arg Lys Ala Arg Ser Ser Phe Thr Thr Arg Ser Ala Thr Lys
545                 550                 555                 560
Asn Leu Ala Met Ser Glu Leu Arg Ala Met Val His Ala Leu Phe Leu
                    565                 570                 575
Glu Ser Cys Ala Gly Val Glu Leu Ala Ser Arg Leu Leu Phe Val Val
            580                 585                 590
Leu Thr Val Cys Val Ser His Glu Ala Gln Ser Ser Gly Ser Lys Arg
        595                 600                 605
Pro Arg Ser Glu Tyr Ala Ser Thr Thr Glu Asn Ile Glu Ala Asn Gln
    610                 615                 620
Pro Val Ser Asn Asn Gln Thr Ala Asn Arg Lys Ser Arg Asn Val Lys
625                 630                 635                 640
Gly Gln Gly Pro Val Ala Ala Phe Asp Ser Tyr Val Leu Ala Ala Val
                    645                 650                 655
Cys Ala Leu Ala Cys Glu Val Gln Leu Tyr Pro Met Ile Ser Gly Gly
            660                 665                 670
Gly Asn Phe Ser Asn Ser Ala Val Ala Gly Thr Ile Thr Lys Pro Val
        675                 680                 685
Lys Ile Asn Gly Ser Ser Lys Glu Tyr Gly Ala Gly Ile Asp Ser Ala
    690                 695                 700
Ile Ser His Thr Arg Arg Ile Leu Ala Ile Leu Glu Ala Leu Phe Ser
705                 710                 715                 720
Leu Lys Pro Ser Ser Val Gly Thr Pro Trp Ser Tyr Ser Ser Ser Glu
                    725                 730                 735
Ile Val Ala Ala Ala Met Val Ala Ala His Ile Ser Glu Leu Phe Arg
            740                 745                 750
Arg Ser Lys Ala Leu Thr His Ala Leu Ser Gly Leu Met Arg Cys Lys
        755                 760                 765
Trp Asp Lys Glu Ile His Lys Arg Ala Ser Ser Leu Tyr Asn Leu Ile
    770                 775                 780
Asp Val His Ser Lys Val Val Ala Ser Ile Val Asp Lys Ala Glu Pro
785                 790                 795                 800
Leu Glu Ala Tyr Leu Lys Asn Thr Pro Val Gln Lys Asp Ser Val Thr
                    805                 810                 815
Cys Leu Asn Trp Lys Gln Glu Asn Thr Cys Ala Ser Thr Thr Cys Phe
            820                 825                 830
Asp Thr Ala Val Thr Ser Ala Ser Arg Thr Glu Met Asn Pro Arg Gly
        835                 840                 845
Asn His Lys Tyr Ala Arg His Ser Asp Glu Gly Ser Gly Arg Pro Ser
    850                 855                 860
Glu Lys Gly Ile Lys Asp Phe Leu Leu Asp Ala Ser Asp Leu Ala Asn
```

```
                865                 870                 875                 880
Phe Leu Thr Ala Asp Arg Leu Ala Gly Phe Tyr Cys Gly Thr Gln Lys
                    885                 890                 895
Leu Leu Arg Ser Val Leu Ala Glu Lys Pro Glu Leu Ser Phe Ser Val
                900                 905                 910
Val Ser Leu Leu Trp His Lys Leu Ile Ala Ala Pro Glu Ile Gln Pro
            915                 920                 925
Thr Ala Glu Ser Thr Ser Ala Gln Gln Gly Trp Arg Gln Val Val Asp
        930                 935                 940
Ala Leu Cys Asn Val Val Ser Ala Thr Pro Ala Lys Ala Ala Ala
945                 950                 955                 960
Val Val Leu Gln Ala Glu Arg Glu Leu Gln Pro Trp Ile Ala Lys Asp
                965                 970                 975
Asp Glu Glu Gly Gln Lys Met Trp Lys Ile Asn Gln Arg Ile Val Lys
            980                 985                 990
Val Leu Val Glu Leu Met Arg Asn   His Asp Arg Pro Glu  Ser Leu Val
                995                 1000                1005
Ile Leu  Ala Ser Ala Ser Asp  Leu Leu Leu Arg Ala  Thr Asp Gly
    1010                1015                1020
Met Leu  Val Asp Gly Glu Ala  Cys Thr Leu Pro Gln  Leu Glu Leu
    1025                1030                1035
Leu Glu  Ala Thr Ala Arg Ala  Ile Gln Pro Val Leu  Ala Trp Gly
    1040                1045                1050
Pro Ser  Gly Leu Ala Val Val  Asp Gly Leu Ser Asn  Leu Leu Lys
    1055                1060                1065
Cys Arg  Leu Pro Ala Thr Ile  Arg Cys Leu Ser His  Pro Ser Ala
    1070                1075                1080
His Val  Arg Ala Leu Ser Thr  Ser Val Leu Arg Asp  Ile Met Asn
    1085                1090                1095
Gln Ser  Ser Ile Pro Ile Lys  Val Thr Pro Lys Leu  Pro Thr Thr
    1100                1105                1110
Glu Lys  Asn Gly Met Asn Ser  Pro Ser Tyr Arg Phe  Phe Asn Ala
    1115                1120                1125
Ala Ser  Ile Asp Trp Lys Ala  Asp Ile Gln Asn Cys  Leu Asn Trp
    1130                1135                1140
Glu Ala  His Ser Leu Leu Ser  Thr Thr Met Pro Thr  Gln Phe Leu
    1145                1150                1155
Asp Thr  Ala Ala Arg Glu Leu  Gly Cys Thr Ile Ser  Leu Ser Gln
    1160                1165                1170

<210> SEQ ID NO 7
<211> LENGTH: 2931
<212> TYPE: DNA
<213> ORGANISM: Rice

<400> SEQUENCE: 7
cggaagccat tgaggccact atctccttgg atcacagaca tattgcttgc tgcacctctg      60
ggtattagaa gtgactattt tagatggtgt ggtggagtca tgggaaaata cgcagctggt     120
ggagaattga agcctccaac aactgcttac agccgaggat ctgggaagca cccacaactt     180
atgccatcca cgcccagatg ggctgctgcc aatggagctg gagttatact aagtgtctgt     240
gatgaggaag tagctcgtta tgagacagca aatttgactg cggcagctgt tcctgcactt     300
ctattacctc caccgaccac accattggac gaacatttgg ttgcgggggct ccctcctctt     360
```

```
gaaccatatg ctcgcttgtt tcatagatac tatgcaattg ctactccaag tgctacccaa      420
aggttgcttt ttggtcttct cgaggcacca ccaccatggg ccccagatgc acttgatgca      480
gcagtacagc ttgttgaact ccttagagca gcggaagatt acgattctgg catgcggctt      540
ccaaagaact ggatgcatct tcatttcctg cgtgctattg gaactgcaat gtcaatgaga      600
gctggtatcg ctgctgatac gtctgctgct ttacttttcc gaatactctc ccaaccgaca      660 ttacttttc ctccactgac acatgccgaa ggagttgaac tccatcatga gccactaggt       720
ggctatgtat catcgtacaa aaggcagctg gaagttcctg catctgaagc cactattgat      780 gccactcgc aaggcattgc ttccatgcta tgtgctcatg gtcccgatgt tgagtggaga       840
atatgtacca tctgggaggc tgcgtatggt ttgctaccct tgagttcatc agcagttgat      900
ttgcctgaaa ttgttgtagc tgctccactt cagccaccta ctttgtcatg gagcctatac      960
ttgccattgt tgaaagtatt tgagtattta cctcgtggga gtccatctga agcatgcctt      1020
atgagaattt ttgtggcaac agttgaagct atactgagaa gaactttttcc atcagaaacc    1080 tctgaacaat ccaggaaacc aagaagtcaa tctaagaacc ttgctgttgc tgaactccga     1140
acaatgatac attcactctt tgtggagtcc tgtgcttcaa tggaccttgc gtccagatta     1200
ctatttgtag tattaactgt ttgcgtcagt catcaagctt tgcctggggg aagtaaaagg     1260
ccaactggta gtgataatca ttcctctgag gaggtcacaa atgattcgag attaaccaac     1320
ggaagaaaca gatgtaagaa gagacaagga ccagttgcta cattcgactc atacgttcta     1380
gcagccgttt gtgccttatc ttgtgagctc cagctgttcc cttttatttc caagaatggg     1440
aaccattcaa atctgaagga ctccataaag atagtcatac ctggaaaaac cactggtatc     1500
agtaacgagc tacacaatag cattagctca gcgattcttc atactcgtag aatacttggc     1560
atcttggaag ctctgttctc cttgaagcca tcatctgttg gtacttcatg gagttatagt     1620
tcaaatgaga ttgttgcagc agctatggtt gctgctcatg tttctgagtt atttcgtcga     1680
tccaggccat gcttaaatgc actgtctgcg ctgaagcaat gcaagtggga tgctgagatt     1740
tctaccaggg catcatccct ttaccatttg attgacttgc atggtaaaac agtgacctcc     1800
attgtgaaca aagctgagcc tctagaagct cacctgaccc ttacaccagt aaaaaaggat     1860
gaacctccca ttgaggaaaa gaacattaac tcatcagatg gtggtgcatt ggaaaaaaag     1920
gatgcttcaa gatcacacag gaaaaatggt tttgcaagac cactcttgaa atgtgcagaa     1980
gatgttatac taaatggtga tgtcgcaagt acttctggga aagccattgc aagtttacag     2040
gtggaagctt ctgatttggc aaacttcctc accatggacc gaaatggggg ttacagaggt     2100
tctcaaactc tcctaagatc tgtactgtca gagaagcagg agctatgctt ctctgttgtc     2160
tcattgctct ggcagaagct cattgcatct cccgaaatgc agatgtctgc agaaagtaca     2220
tcagctcatc agggttggag aaaggttgtg gatgcgcttt gtgacattgt ttcagcctca     2280
ccgaccaagg cttcagctgc tatcgttctg caggccgaga aggacttgca gccctggatt     2340
gctcgagatg atgagcaagg tcagaagatg tggagagtca accagcgaat agttaagctg     2400
atagcagagc ttatgaggaa ccacgatagc ccagaagcat ggtgatcct tgctagtgct      2460 tcagatcttc cccttcgagc aactgatgga atgcttgttg atggtgaagc ttgcaccta     2520 ccacaattag agctattgga agtaaccgcc agagcagtcc atctcatcgt cgaatgggga     2580
gattcaggtg tatccgtcgc tgatggcctc tccaatctgc tgaagtgccg tctatcaacc     2640
accatccgct gtctttcgca ccccagcgcg catgtccgtg cactcagcat gtccgtcctt     2700
cgcgacatct tgaacagcgg acaaataaac tccagtaagc tcatccaagg ggaacaccgg     2760
```

```
aatggcatcc agagcccaac ctaccagtgc ttggcagcaa gcatcatcaa ctggcacgcc    2820
gatgtggaga gatgcataga gtgggaagcc cacagccgcc gcgccaccgg gctgacgctc    2880
gccttcctca ccgcggcgaa ggagctcggc tgcccactca cttgctgaca a             2931
```

<210> SEQ ID NO 8
<211> LENGTH: 975
<212> TYPE: PRT
<213> ORGANISM: Rice

<400> SEQUENCE: 8

```
Arg Lys Pro Leu Arg Pro Leu Ser Pro Trp Ile Thr Asp Ile Leu Leu
1               5                   10                  15

Ala Ala Pro Leu Gly Ile Arg Ser Asp Tyr Phe Arg Trp Cys Gly Gly
            20                  25                  30

Val Met Gly Lys Tyr Ala Ala Gly Gly Glu Leu Lys Arg Pro Thr Thr
        35                  40                  45

Ala Tyr Ser Arg Gly Ser Gly Lys His Pro Gln Leu Met Pro Ser Thr
    50                  55                  60

Pro Arg Trp Ala Val Ala Asn Gly Ala Gly Val Ile Leu Ser Val Cys
65                  70                  75                  80

Asp Glu Glu Val Ala Arg Tyr Glu Thr Ala Asn Leu Thr Ala Ala
                85                  90                  95

Val Pro Ala Leu Leu Leu Pro Pro Ile Thr Pro Leu Asp Glu His
            100                 105                 110

Leu Val Ala Gly Leu Pro Pro Leu Glu Pro Tyr Ala Arg Leu Phe His
        115                 120                 125

Arg Tyr Tyr Ala Ile Ala Thr Pro Ser Ala Thr Gln Arg Leu Leu Phe
    130                 135                 140

Gly Leu Leu Glu Ala Pro Pro Ser Trp Ala Pro Asp Ala Leu Asp Ala
145                 150                 155                 160

Ala Val Gln Leu Val Glu Leu Leu Arg Ala Ala Glu Asp Tyr Asp Ser
                165                 170                 175

Gly Met Arg Leu Pro Lys Asn Trp Met His Leu His Phe Leu Arg Ala
            180                 185                 190

Ile Gly Thr Ala Met Ser Met Arg Ala Gly Ile Ala Ala Asp Thr Ser
        195                 200                 205

Ala Ala Leu Leu Phe Arg Ile Leu Ser Gln Pro Thr Leu Leu Phe Pro
    210                 215                 220

Pro Leu Arg His Ala Glu Gly Val Glu Leu His His Glu Pro Leu Gly
225                 230                 235                 240

Gly Tyr Val Ser Ser Tyr Lys Arg Gln Leu Glu Val Pro Ala Ser Glu
                245                 250                 255

Ala Thr Ile Asp Ala Thr Ala Gln Gly Ile Ala Ser Met Leu Cys Ala
            260                 265                 270

His Gly Pro Asp Val Glu Trp Arg Ile Cys Thr Ile Trp Glu Ala Ala
        275                 280                 285

Tyr Gly Leu Leu Pro Leu Ser Ser Ala Val Asp Leu Pro Glu Ile
    290                 295                 300

Val Val Ala Ala Pro Leu Gln Pro Pro Thr Leu Ser Trp Ser Leu Tyr
305                 310                 315                 320

Leu Pro Leu Leu Lys Val Phe Glu Tyr Leu Pro Arg Gly Ser Pro Ser
                325                 330                 335

Glu Ala Cys Leu Met Arg Ile Phe Val Ala Thr Val Glu Ala Ile Leu
```

```
                    340             345             350
Arg Arg Thr Phe Pro Ser Glu Thr Ser Glu Gln Ser Arg Lys Pro Arg
            355                 360                 365
Ser Gln Ser Lys Asn Leu Ala Val Ala Glu Leu Arg Thr Met Ile His
            370                 375                 380
Ser Leu Phe Val Glu Ser Cys Ala Ser Met Asp Leu Ala Ser Arg Leu
385                 390                 395                 400
Leu Phe Val Val Leu Thr Val Cys Val Ser His Gln Ala Leu Pro Gly
                    405                 410                 415
Gly Ser Lys Arg Pro Thr Gly Ser Asp Asn His Ser Ser Glu Glu Val
            420                 425                 430
Thr Asn Asp Ser Arg Leu Thr Asn Gly Arg Asn Arg Cys Lys Lys Arg
            435                 440                 445
Gln Gly Pro Val Ala Thr Phe Asp Ser Tyr Val Leu Ala Ala Val Cys
            450                 455                 460
Ala Leu Ser Cys Glu Leu Gln Leu Phe Pro Phe Ile Ser Lys Asn Gly
465                 470                 475                 480
Asn His Ser Asn Leu Lys Asp Ser Ile Lys Ile Val Ile Pro Gly Lys
            485                 490                 495
Thr Thr Gly Ile Ser Asn Glu Leu His Asn Ser Ile Ser Ser Ala Ile
            500                 505                 510
Leu His Thr Arg Arg Ile Leu Gly Ile Leu Glu Ala Leu Phe Ser Leu
            515                 520                 525
Lys Pro Ser Ser Val Gly Thr Ser Trp Ser Tyr Ser Ser Asn Glu Ile
            530                 535                 540
Val Ala Ala Met Val Ala Ala His Val Ser Glu Leu Phe Arg Arg
545                 550                 555                 560
Ser Arg Pro Cys Leu Asn Ala Leu Ser Ala Leu Lys Gln Cys Lys Trp
            565                 570                 575
Asp Ala Glu Ile Ser Thr Arg Ala Ser Ser Leu Tyr His Leu Ile Asp
            580                 585                 590
Leu His Gly Lys Thr Val Thr Ser Ile Val Asn Lys Ala Glu Pro Leu
            595                 600                 605
Glu Ala His Leu Thr Leu Thr Pro Val Lys Lys Asp Glu Pro Pro Ile
            610                 615                 620
Glu Glu Lys Asn Ile Asn Ser Ser Asp Gly Gly Ala Leu Glu Lys Lys
625                 630                 635                 640
Asp Ala Ser Arg Ser His Arg Lys Asn Gly Phe Ala Arg Pro Leu Leu
            645                 650                 655
Lys Cys Ala Glu Asp Val Ile Leu Asn Gly Asp Val Ala Ser Thr Ser
            660                 665                 670
Gly Lys Ala Ile Ala Ser Leu Gln Val Glu Ala Ser Asp Leu Ala Asn
            675                 680                 685
Phe Leu Thr Met Asp Arg Asn Gly Gly Tyr Arg Gly Ser Gln Thr Leu
            690                 695                 700
Leu Arg Ser Val Leu Ser Glu Lys Gln Glu Leu Cys Phe Ser Val Val
705                 710                 715                 720
Ser Leu Leu Trp Gln Lys Leu Ile Ala Ser Pro Glu Met Gln Met Ser
            725                 730                 735
Ala Glu Ser Thr Ser Ala His Gln Gly Trp Arg Lys Val Val Asp Ala
            740                 745                 750
Leu Cys Asp Ile Val Ser Ala Ser Pro Thr Lys Ala Ser Ala Ala Ile
            755                 760                 765
```

-continued

```
Val Leu Gln Ala Glu Lys Asp Leu Gln Pro Trp Ile Ala Arg Asp Asp
        770                 775                 780
Glu Gln Gly Gln Lys Met Trp Arg Val Asn Gln Arg Ile Val Lys Leu
785                 790                 795                 800
Ile Ala Glu Leu Met Arg Asn His Asp Ser Pro Glu Ala Leu Val Ile
                    805                 810                 815
Leu Ala Ser Ala Ser Asp Leu Leu Arg Ala Thr Asp Gly Met Leu
                820                 825                 830
Val Asp Gly Glu Ala Cys Thr Leu Pro Gln Leu Glu Leu Leu Glu Val
                835                 840                 845
Thr Ala Arg Ala Val His Leu Ile Val Glu Trp Gly Asp Ser Gly Val
850                 855                 860
Ser Val Ala Asp Gly Leu Ser Asn Leu Leu Lys Cys Arg Leu Ser Thr
865                 870                 875                 880
Thr Ile Arg Cys Leu Ser His Pro Ser Ala His Val Arg Ala Leu Ser
                885                 890                 895
Met Ser Val Leu Arg Asp Ile Leu Asn Ser Gly Gln Ile Asn Ser Ser
                900                 905                 910
Lys Leu Ile Gln Gly Glu His Arg Asn Gly Ile Gln Ser Pro Thr Tyr
                915                 920                 925
Gln Cys Leu Ala Ala Ser Ile Ile Asn Trp Gln Ala Asp Val Glu Arg
930                 935                 940
Cys Ile Glu Trp Glu Ala His Ser Arg Arg Ala Thr Gly Leu Thr Leu
945                 950                 955                 960
Ala Phe Leu Thr Ala Ala Lys Glu Leu Gly Cys Pro Leu Thr Cys
                965                 970                 975

<210> SEQ ID NO 9
<211> LENGTH: 1173
<212> TYPE: PRT
<213> ORGANISM: Arabidopsis sp.

<400> SEQUENCE: 9

Met Ala Ser Ser Ser Ser Glu Arg Trp Ile Asp Gly Leu Gln Phe
1               5                   10                  15
Ser Ser Leu Leu Trp Pro Pro Arg Asp Pro Gln Gln His Lys Asp
                20                  25                  30
Gln Val Val Ala Tyr Val Glu Tyr Phe Gly Gln Phe Thr Ser Glu Gln
            35                  40                  45
Phe Pro Asp Asp Ile Ala Glu Leu Val Arg His Gln Tyr Pro Ser Thr
    50                  55                  60
Glu Lys Arg Leu Leu Asp Asp Val Leu Ala Met Phe Val Leu His His
65                  70                  75                  80
Pro Glu His Gly His Ala Val Ile Leu Pro Ile Ser Cys Leu Ile
                85                  90                  95
Asp Gly Ser Leu Val Tyr Ser Lys Glu Ala His Pro Phe Ala Ser Phe
                100                 105                 110
Ile Ser Leu Val Cys Pro Ser Ser Glu Asn Asp Tyr Ser Glu Gln Trp
            115                 120                 125
Ala Leu Ala Cys Gly Glu Ile Leu Arg Ile Leu Thr His Tyr Asn Arg
130                 135                 140
Pro Ile Tyr Lys Thr Glu Gln Gln Asn Gly Asp Thr Glu Arg Asn Cys
145                 150                 155                 160
Leu Ser Lys Ala Thr Thr Ser Gly Ser Pro Thr Ser Glu Pro Lys Ala
```

-continued

```
                    165                 170                 175
Gly Ser Pro Thr Gln His Glu Arg Lys Pro Leu Arg Pro Leu Ser Pro
                180                 185                 190
Trp Ile Ser Asp Ile Leu Leu Ala Ala Pro Leu Gly Ile Arg Ser Asp
                195                 200                 205
Tyr Phe Arg Trp Cys Ser Gly Val Met Gly Lys Tyr Ala Ala Gly Glu
            210                 215                 220
Leu Lys Pro Pro Thr Ile Glu Ser Arg Gly Ser Gly Lys His Pro Gln
225                 230                 235                 240
Leu Met Pro Ser Thr Pro Arg Trp Ala Val Ala Asn Gly Ala Gly Val
                245                 250                 255
Ile Leu Ser Val Cys Asp Asp Glu Val Ala Arg Tyr Glu Thr Ala Thr
                260                 265                 270
Leu Thr Ala Val Ala Val Pro Ala Leu Leu Pro Pro Pro Thr Thr
                275                 280                 285
Ser Leu Asp Glu His Leu Val Ala Gly Leu Pro Ala Leu Glu Pro Tyr
            290                 295                 300
Ala Arg Leu Phe His Arg Tyr Tyr Ala Ile Ala Thr Pro Ser Ala Thr
305                 310                 315                 320
Gln Arg Leu Leu Leu Gly Leu Leu Glu Ala Pro Pro Ser Trp Ala Pro
                325                 330                 335
Asp Ala Leu Asp Ala Ala Val Gln Leu Val Glu Leu Leu Arg Ala Ala
                340                 345                 350
Glu Asp Tyr Ala Ser Gly Val Arg Leu Pro Arg Asn Trp Met His Leu
            355                 360                 365
His Phe Leu Arg Ala Ile Gly Ile Ala Met Ser Met Arg Ala Gly Val
        370                 375                 380
Ala Ala Asp Ala Ala Ala Leu Leu Phe Arg Ile Leu Ser Gln Pro
385                 390                 395                 400
Ala Leu Leu Phe Pro Pro Leu Ser Gln Val Glu Gly Val Glu Ile Gln
                405                 410                 415
His Ala Pro Ile Gly Gly Tyr Ser Ser Asn Tyr Arg Lys Gln Ile Glu
                420                 425                 430
Val Pro Ala Ala Glu Ala Thr Ile Glu Ala Thr Ala Gln Gly Ile Ala
                435                 440                 445
Ser Met Leu Cys Ala His Gly Pro Glu Val Glu Trp Arg Ile Cys Thr
                450                 455                 460
Ile Trp Glu Ala Ala Tyr Gly Leu Ile Pro Leu Asn Ser Ser Ala Val
465                 470                 475                 480
Asp Leu Pro Glu Ile Ile Val Ala Thr Pro Leu Gln Pro Pro Ile Leu
                485                 490                 495
Ser Trp Asn Leu Tyr Ile Pro Leu Leu Lys Val Leu Glu Tyr Leu Pro
                500                 505                 510
Arg Gly Ser Pro Ser Glu Ala Cys Leu Met Lys Ile Phe Val Ala Thr
            515                 520                 525
Val Glu Thr Ile Leu Ser Arg Thr Phe Pro Pro Glu Ser Ser Arg Glu
            530                 535                 540
Leu Thr Arg Lys Ala Arg Ser Ser Phe Thr Thr Arg Ser Ala Thr Lys
545                 550                 555                 560
Asn Leu Ala Met Ser Glu Leu Arg Ala Met Val His Ala Leu Phe Leu
                565                 570                 575
Glu Ser Cys Ala Gly Val Glu Leu Ala Ser Arg Leu Leu Phe Val Val
                580                 585                 590
```

```
Leu Thr Val Cys Val Ser His Glu Ala Gln Ser Ser Gly Ser Lys Arg
        595                 600                 605
Pro Arg Ser Glu Tyr Ala Ser Thr Thr Glu Asn Ile Glu Ala Asn Gln
        610                 615                 620
Pro Val Ser Asn Asn Gln Thr Ala Asn Arg Lys Ser Arg Asn Val Lys
625                 630                 635                 640
Gly Gln Gly Pro Val Ala Ala Phe Asp Ser Tyr Val Leu Ala Ala Val
            645                 650                 655
Cys Ala Leu Ala Cys Glu Val Gln Leu Tyr Pro Met Ile Ser Gly Gly
        660                 665                 670
Gly Asn Phe Ser Asn Ser Ala Val Ala Gly Thr Ile Thr Lys Pro Val
        675                 680                 685
Lys Ile Asn Gly Ser Ser Lys Glu Tyr Gly Ala Gly Ile Asp Ser Ala
        690                 695                 700
Ile Ser His Thr Arg Arg Ile Leu Ala Ile Leu Glu Ala Leu Phe Ser
705                 710                 715                 720
Leu Lys Pro Ser Ser Val Gly Thr Pro Trp Ser Tyr Ser Ser Ser Glu
            725                 730                 735
Ile Val Ala Ala Ala Met Val Ala Ala His Ile Ser Glu Leu Phe Arg
        740                 745                 750
Arg Ser Lys Ala Leu Thr His Ala Leu Ser Gly Leu Met Arg Cys Lys
        755                 760                 765
Trp Asp Lys Glu Ile His Lys Arg Ala Ser Ser Leu Tyr Asn Leu Ile
        770                 775                 780
Asp Val His Ser Lys Val Val Ala Ser Ile Val Asp Lys Ala Glu Pro
785                 790                 795                 800
Leu Glu Ala Tyr Leu Lys Asn Thr Pro Val Gln Lys Asp Ser Val Thr
            805                 810                 815
Cys Leu Asn Trp Lys Gln Glu Asn Thr Cys Ala Ser Thr Thr Cys Phe
        820                 825                 830
Asp Thr Ala Val Thr Ser Ala Ser Arg Thr Glu Met Asn Pro Arg Gly
        835                 840                 845
Asn His Lys Tyr Ala Arg His Ser Asp Glu Gly Ser Gly Arg Pro Ser
850                 855                 860
Glu Lys Gly Ile Lys Asp Phe Leu Leu Asp Ala Ser Asp Leu Ala Asn
865                 870                 875                 880
Phe Leu Thr Ala Asp Arg Leu Ala Gly Phe Tyr Cys Gly Thr Gln Lys
            885                 890                 895
Leu Leu Arg Ser Val Leu Ala Glu Lys Pro Glu Leu Ser Phe Ser Val
                900                 905                 910
Val Ser Leu Leu Trp His Lys Leu Ile Ala Ala Pro Glu Ile Gln Pro
        915                 920                 925
Thr Ala Glu Ser Thr Ser Ala Gln Gln Gly Trp Arg Gln Val Val Asp
        930                 935                 940
Ala Leu Cys Asn Val Val Ser Ala Thr Pro Ala Lys Ala Ala Ala
945                 950                 955                 960
Val Val Leu Gln Ala Glu Arg Glu Leu Gln Pro Trp Ile Ala Lys Asp
            965                 970                 975
Asp Glu Glu Gly Gln Lys Met Trp Lys Ile Asn Gln Arg Ile Val Lys
                980                 985                 990
Val Leu Val Glu Leu Met Arg Asn His Asp Arg Pro Glu Ser Leu Val
        995                 1000                1005
```

```
Ile Leu Ala Ser Ala Ser Asp Leu Leu Leu Arg Ala Thr Asp Gly
    1010            1015                1020

Met Leu Val Asp Gly Glu Ala Cys Thr Leu Pro Gln Leu Glu Leu
    1025            1030                1035

Leu Glu Ala Thr Ala Arg Ala Ile Gln Pro Val Leu Ala Trp Gly
    1040            1045                1050

Pro Ser Gly Leu Ala Val Val Asp Gly Leu Ser Asn Leu Leu Lys
    1055            1060                1065

Cys Arg Leu Pro Ala Thr Ile Arg Cys Leu Ser His Pro Ser Ala
    1070            1075                1080

His Val Arg Ala Leu Ser Thr Ser Val Leu Arg Asp Ile Met Asn
    1085            1090                1095

Gln Ser Ser Ile Pro Ile Lys Val Thr Pro Lys Leu Pro Thr Thr
    1100            1105                1110

Glu Lys Asn Gly Met Asn Ser Pro Ser Tyr Arg Phe Phe Asn Ala
    1115            1120                1125

Ala Ser Ile Asp Trp Lys Ala Asp Ile Gln Asn Cys Leu Asn Trp
    1130            1135                1140

Glu Ala His Ser Leu Leu Ser Thr Thr Met Pro Thr Gln Phe Leu
    1145            1150                1155

Asp Thr Ala Ala Arg Glu Leu Gly Cys Thr Ile Ser Leu Ser Gln
    1160            1165                1170
```

<210> SEQ ID NO 10
<211> LENGTH: 19
<212> TYPE: DNA
<213> ORGANISM: ARTIFICIAL
<220> FEATURE:
<223> OTHER INFORMATION: Made in Laboratory

<400> SEQUENCE: 10
agctggtaca ttgccgtag                                              19

<210> SEQ ID NO 11
<211> LENGTH: 22
<212> TYPE: DNA
<213> ORGANISM: Artificial
<220> FEATURE:
<223> OTHER INFORMATION: Made in Laboratory

<400> SEQUENCE: 11
tttttgcttg gactataata cc                                          22

<210> SEQ ID NO 12
<211> LENGTH: 22
<212> TYPE: DNA
<213> ORGANISM: Artificial
<220> FEATURE:
<223> OTHER INFORMATION: Made in Laboratory

<400> SEQUENCE: 12
tagatgaaag actgagtgcg at                                          22

<210> SEQ ID NO 13
<211> LENGTH: 22
<212> TYPE: DNA
<213> ORGANISM: Artificial
<220> FEATURE:
<223> OTHER INFORMATION: Made in Laboratory

<400> SEQUENCE: 13

-continued ctacaaattg cctttctta tc                                              22

<210> SEQ ID NO 14
<211> LENGTH: 18
<212> TYPE: DNA
<213> ORGANISM: Artificial
<220> FEATURE:
<223> OTHER INFORMATION: Made in Laboratory

<400> SEQUENCE: 14
gttcagacgt tcaaaggc                                                  18

<210> SEQ ID NO 15
<211> LENGTH: 18
<212> TYPE: DNA
<213> ORGANISM: Artificial
<220> FEATURE:
<223> OTHER INFORMATION: Made in Laboratory

<400> SEQUENCE: 15
aactccaatc ccaaaacc                                                  18

<210> SEQ ID NO 16
<211> LENGTH: 18
<212> TYPE: DNA
<213> ORGANISM: Artificial
<220> FEATURE:
<223> OTHER INFORMATION: Made in Laboratory

<400> SEQUENCE: 16
ttcggttcct ggatggct                                                  18

<210> SEQ ID NO 17
<211> LENGTH: 18
<212> TYPE: DNA
<213> ORGANISM: Artificial
<220> FEATURE:
<223> OTHER INFORMATION: Made in Laboratory

<400> SEQUENCE: 17
tggttcaaga gctggaag                                                  18

<210> SEQ ID NO 18
<211> LENGTH: 24
<212> TYPE: DNA
<213> ORGANISM: Artificial
<220> FEATURE:
<223> OTHER INFORMATION: Made in Laboratory

<400> SEQUENCE: 18
tggagagctc aagccgccaa ccat                                           24

<210> SEQ ID NO 19
<211> LENGTH: 26
<212> TYPE: DNA
<213> ORGANISM: Artificial
<220> FEATURE:
<223> OTHER INFORMATION: Made in Laboratory

<400> SEQUENCE: 19
ctcttgctac cactagactg tgcttc                                         26

<210> SEQ ID NO 20
<211> LENGTH: 22
<212> TYPE: DNA
<213> ORGANISM: Artificial

```
<220> FEATURE:
<223> OTHER INFORMATION: Made in Laboratory

<400> SEQUENCE: 20
cacagtctag tggtagcaag ag                                              22

<210> SEQ ID NO 21
<211> LENGTH: 18
<212> TYPE: DNA
<213> ORGANISM: Artificial
<220> FEATURE:
<223> OTHER INFORMATION: Made in Laboratory

<400> SEQUENCE: 21
gtgggtgctc gttattgg                                                   18

<210> SEQ ID NO 22
<211> LENGTH: 17
<212> TYPE: DNA
<213> ORGANISM: Artificial
<220> FEATURE:
<223> OTHER INFORMATION: Made in Laboratory

<400> SEQUENCE: 22
aatacgactc actatag                                                    17

<210> SEQ ID NO 23
<211> LENGTH: 17
<212> TYPE: DNA
<213> ORGANISM: Artificial
<220> FEATURE:
<223> OTHER INFORMATION: Made in Laboratory

<400> SEQUENCE: 23
gtaaaacgac ggccagt                                                    17

<210> SEQ ID NO 24
<211> LENGTH: 16
<212> TYPE: DNA
<213> ORGANISM: Artificial
<220> FEATURE:
<223> OTHER INFORMATION: Made in Laboratory

<400> SEQUENCE: 24
aacagctatg accatg                                                     16

<210> SEQ ID NO 25
<211> LENGTH: 21
<212> TYPE: DNA
<213> ORGANISM: Artificial
<220> FEATURE:
<223> OTHER INFORMATION: Made in Laboratory

<400> SEQUENCE: 25
cccacaactt atgccatcca c                                               21

<210> SEQ ID NO 26
<211> LENGTH: 21
<212> TYPE: DNA
<213> ORGANISM: Artificial
<220> FEATURE:
<223> OTHER INFORMATION: Made in Laboratory

<400> SEQUENCE: 26
cctcagagga atgattatca c                                               21
```

```
<210> SEQ ID NO 27
<211> LENGTH: 21
<212> TYPE: DNA
<213> ORGANISM: Artificial
<220> FEATURE:
<223> OTHER INFORMATION: Made in Laboratory

<400> SEQUENCE: 27
gccatgctta aatgcactgt c                                              21

<210> SEQ ID NO 28
<211> LENGTH: 19
<212> TYPE: DNA
<213> ORGANISM: Artificial
<220> FEATURE:
<223> OTHER INFORMATION: Made in Laboratory

<400> SEQUENCE: 28
ttgtcagcaa gtgagtggg                                                 19

<210> SEQ ID NO 29
<211> LENGTH: 21
<212> TYPE: DNA
<213> ORGANISM: Artificial
<220> FEATURE:
<223> OTHER INFORMATION: Made in Laboratory

<400> SEQUENCE: 29
cagatgcact tgatgcagca g                                              21

<210> SEQ ID NO 30
<211> LENGTH: 21
<212> TYPE: DNA
<213> ORGANISM: Artificial
<220> FEATURE:
<223> OTHER INFORMATION: Made in Laboratory

<400> SEQUENCE: 30
agcagctaca acaatttcag c                                              21

<210> SEQ ID NO 31
<211> LENGTH: 19
<212> TYPE: DNA
<213> ORGANISM: Artificial
<220> FEATURE:
<223> OTHER INFORMATION: Made in Laboratory

<400> SEQUENCE: 31
gtcagaagca ggagctatg                                                 19

<210> SEQ ID NO 32
<211> LENGTH: 21
<212> TYPE: DNA
<213> ORGANISM: Artificial
<220> FEATURE:
<223> OTHER INFORMATION: Made in Laboratory

<400> SEQUENCE: 32
ttcaccatca acaagcattc c                                              21

<210> SEQ ID NO 33
<211> LENGTH: 14
<212> TYPE: DNA
<213> ORGANISM: Artificial
<220> FEATURE:
<223> OTHER INFORMATION: Made in Laboratory
```

```
<400> SEQUENCE: 33
ccttgtctct tctt                                                      14

<210> SEQ ID NO 34
<211> LENGTH: 19
<212> TYPE: DNA
<213> ORGANISM: Artificial
<220> FEATURE:
<223> OTHER INFORMATION: Made in Laboratory

<400> SEQUENCE: 34
ctctgttctc cttgaagcc                                                 19

<210> SEQ ID NO 35
<211> LENGTH: 20
<212> TYPE: DNA
<213> ORGANISM: Artificial
<220> FEATURE:
<223> OTHER INFORMATION: Made in Laboratory

<400> SEQUENCE: 35
cttctaatac ccagaggtgc                                                20

<210> SEQ ID NO 36
<211> LENGTH: 22
<212> TYPE: DNA
<213> ORGANISM: Artificial
<220> FEATURE:
<223> OTHER INFORMATION: Made in Laboratory

<400> SEQUENCE: 36
gcaatatgtc tgtgatccaa gg                                             22

<210> SEQ ID NO 37
<211> LENGTH: 21
<212> TYPE: PRT
<213> ORGANISM: Artificial
<220> FEATURE:
<223> OTHER INFORMATION: Made in Laboratory

<400> SEQUENCE: 37

Thr Pro Lys Leu Pro Thr Thr Glu Lys Asn Gly Met Asn Ser Pro Ser
1               5                   10                  15

Tyr Arg Phe Phe Asn
            20

<210> SEQ ID NO 38
<211> LENGTH: 20
<212> TYPE: PRT
<213> ORGANISM: Artificial
<220> FEATURE:
<223> OTHER INFORMATION: Made in Laboratory

<400> SEQUENCE: 38

Glu Arg Glu Leu Gln Pro Trp Ile Ala Lys Asp Asp Glu Glu Gly Gln
1               5                   10                  15

Lys Met Trp Lys
            20

<210> SEQ ID NO 39
<211> LENGTH: 377
<212> TYPE: DNA
<213> ORGANISM: Arabidopsis sp.
<220> FEATURE:
```

```
<221> NAME/KEY: misc_feature
<222> LOCATION: (23)..(23)
<223> OTHER INFORMATION: Unsure (n = a, g, c, or t)
<220> FEATURE:
<221> NAME/KEY: misc_feature
<222> LOCATION: (59)..(59)
<223> OTHER INFORMATION: Unsure (n = a, g, c, or t)
<220> FEATURE:
<221> NAME/KEY: misc_feature
<222> LOCATION: (125)..(125)
<223> OTHER INFORMATION: Unsure (n = a, g, c, or t)
<220> FEATURE:
<221> NAME/KEY: misc_feature
<222> LOCATION: (150)..(150)
<223> OTHER INFORMATION: Unsure (n = a, g, c, or t)
<220> FEATURE:
<221> NAME/KEY: misc_feature
<222> LOCATION: (196)..(196)
<223> OTHER INFORMATION: Unsure (n = a, g, c, or t)

<400> SEQUENCE: 39
ttaaagtaga ttttaaaatt agntcatggt taaaaataga cagaattttg gagtaaatnt      60
gagtttaaca aaatttattt attagggatt aaaattaatt aacttaaatt ggcaaacatt     120
ttttnttggt gattgtaaca tacaatatan gaatttgaat tcggaattgt gattccaaaa     180
caacactaac ataaantacc agtaaacttt tttaaaataa aattttgtat atatatgctt     240
aaaaaatgta acaaaaatat ggtaaatttt ttaaccatgg tatgggtgga gatgtatgtg     300
ggatgatgat ggttatatgg taatggcgca taaaggtggt ggcaaaggca aggaaatatc     360
gatgacacgt aagcaga                                                    377

<210> SEQ ID NO 40
<211> LENGTH: 200
<212> TYPE: PRT
<213> ORGANISM: Rice

<400> SEQUENCE: 40

Gln Ala Ser Ser Cys Glu Ser Met Glu Lys Arg Ala Asn Gly Ser Pro
1               5                   10                  15

Arg Asn Glu Pro Asp Arg Lys Pro Leu Arg Pro Leu Ser Pro Trp Ile
            20                  25                  30

Thr Asp Ile Leu Leu Ala Ala Pro Leu Gly Ile Arg Ser Asp Tyr Phe
        35                  40                  45

Arg Trp Lys Ala Thr Thr Ser Gly Ser Pro Thr Ser Glu Pro Lys Ala
    50                  55                  60

Gly Ser Pro Thr Gln His Glu Arg Lys Pro Leu Arg Pro Leu Ser Pro
65                  70                  75                  80

Trp Ile Ser Asp Ile Leu Leu Ala Ala Pro Leu Gly Ile Arg Ser Asp
                85                  90                  95

Tyr Phe Arg Trp Cys Gly Gly Val Met Gly Lys Tyr Ala Ala Gly Gly
            100                 105                 110

Glu Leu Lys Pro Pro Thr Thr Ala Tyr Ser Arg Gly Gly Lys His
        115                 120                 125

Pro Gln Leu Met Pro Ser Thr Pro Arg Trp Ala Val Ala Asn Gly Ala
    130                 135                 140

Gly Val Ile Leu Ser Val Cys Ser Gly Val Met Gly Lys Tyr Ala Ala
145                 150                 155                 160

Gly Glu Leu Lys Pro Pro Thr Ile Glu His Pro Gln Leu Met Pro Ser
                165                 170                 175

Thr Pro Arg Trp Ala Val Ala Asn Gly Ala Gly Val Ile Leu Ser Val
            180                 185                 190
```

Cys Asp Glu Glu Val Pro Arg Tyr
          195                 200

<210> SEQ ID NO 41
<211> LENGTH: 305
<212> TYPE: PRT
<213> ORGANISM: Rice

<400> SEQUENCE: 41

Val Ser His Gln Ala Leu Pro Gly Gly Ser Lys Arg Pro Thr Gly Ser
1               5                   10                  15

Asp Asn His Ser Ser Glu Val Thr Asn Asp Ser Arg Leu Thr Asn
            20                  25                  30

Gly Arg Asn Arg Cys Lys Lys Arg Gln Gly Pro Val Ala Val Ser His
            35                  40                  45

Glu Ala Gln Ser Ser Gly Ser Lys Arg Pro Arg Ser Glu Tyr Ala Ser
        50                  55                  60

Thr Thr Glu Asn Ile Glu Ala Asn Gln Pro Val Ser Asn Asn Gln Thr
65                  70                  75                  80

Ala Asn Arg Lys Ser Arg Asn Val Lys Gly Gln Gly Pro Val Ala Thr
                85                  90                  95

Glu Asp Ser Tyr Val Leu Ala Ala Val Cys Ala Leu Ser Cys Glu Leu
            100                 105                 110

Gln Leu Phe Pro Phe Ile Ser Lys Asn Gly Asn His Asn His Ser Asn
        115                 120                 125

Leu Lys Asp Ser Ile Lys Ile Val Ile Pro Gly Lys Thr Thr Gly Ile
    130                 135                 140

Ser Asn Glu Ala Phe Asp Ser Tyr Val Leu Ala Ala Val Cys Ala Leu
145                 150                 155                 160

Ala Cys Glu Val Gln Leu Tyr Pro Met Ile Ser Gly Gly Asn Phe
                165                 170                 175

Ser Asn Ser Ala Val Ala Gly Thr Ile Thr Lys Pro Val Lys Ile Asn
            180                 185                 190

Gly Ser Ser Lys Glu Leu His Asn Ser Ile Ser Ser Ala Ile Leu His
        195                 200                 205

Thr Arg Arg Ile Leu Gly Ile Leu Glu Ala Leu Phe Ser Leu Lys Pro
    210                 215                 220

Ser Ser Val Gly Thr Ser Trp Ser Tyr Ser Ser Asn Glu Ile Val Ala
225                 230                 235                 240

Ala Ala Met Val Ala Ala His Tyr Gly Ala Gly Ile Asp Ser Ala Ile
                245                 250                 255

Ser His Thr Arg Arg Ile Leu Ala Ile Leu Glu Ala Leu Phe Ser Leu
            260                 265                 270

Lys Pro Ser Ser Val Gly Thr Pro Trp Ser Tyr Ser Ser Ser Glu Ile
        275                 280                 285

Val Ala Ala Ala Met Val Ala Ala His Val Ser Glu Leu Phe Arg Arg
    290                 295                 300

Ser
305

<210> SEQ ID NO 42
<211> LENGTH: 216
<212> TYPE: PRT
<213> ORGANISM: Rice

<400> SEQUENCE: 42

```
Gln Ala Glu Lys Asp Leu Gln Pro Trp Ile Ala Arg Asp Asp Glu Gln
1               5                   10                  15

Gly Gln Lys Met Trp Arg Val Asn Gln Arg Ile Val Lys Leu Ile Ala
            20                  25                  30

Glu Leu Met Arg Asn His Asp Ser Pro Glu Ala Leu Val Ile Leu Ala
        35                  40                  45

Ser Ala Gln Ala Glu Arg Glu Leu Gln Pro Trp Ile Ala Lys Asp Asp
    50                  55                  60

Glu Glu Gly Gln Lys Met Trp Lys Ile Asn Gln Arg Ile Val Lys Val
65              70                  75                  80

Leu Val Glu Leu Met Arg Asn His Asp Arg Pro Glu Ser Leu Val Ile
                85                  90                  95

Leu Ala Ser Ala Ser Asp Leu Leu Leu Arg Ala Thr Asp Gly Met Leu
            100                 105                 110

Val Asp Gly Glu Ala Cys Thr Leu Pro Gln Leu Glu Leu Leu Glu Val
            115                 120                 125

Thr Ala Arg Ala Val His Leu Ile Val Glu Trp Gly Asp Ser Gly Val
130                 135                 140

Ser Val Ala Asp Gly Leu Ser Asp Leu Leu Leu Arg Ala Thr Asp Gly
145             150                 155                 160

Met Leu Val Asp Gly Glu Ala Cys Thr Leu Pro Gln Leu Glu Leu Leu
                165                 170                 175

Glu Ala Thr Ala Arg Ala Ile Gln Pro Val Leu Ala Trp Gly Pro Ser
            180                 185                 190

Gly Leu Ala Val Val Asp Gly Leu Ser Asn Leu Leu Lys Cys Arg Leu
            195                 200                 205

Ser Thr Thr Ile Arg Cys Leu Ser
    210                 215

<210> SEQ ID NO 43
<211> LENGTH: 372
<212> TYPE: DNA
<213> ORGANISM: Arabidopsis thaliana
<220> FEATURE:
<221> NAME/KEY: misc_feature
<222> LOCATION: (1)..(372)
<223> OTHER INFORMATION: Correspond to nucleotides 14482 to 14853 of
      Genbank Accession No. Y12227

<400> SEQUENCE: 43
tttaagtaga ttttaaactt agctcatggt taaaaataga cagaattttg gagtaaatct    60
gagtttacaa aatttattta ttaggattaa aattaattac ttaaattggc aaacattttt   120
cttggtgatt gtaacataca atatacgaat ttgaattcgc attgtgattc caaaacaaca   180
ctaacataaa ctaccagtaa aattttttaa aataaaattt catatatata tgcttaaaaa   240
atgtaacaaa aatatggtaa atttttttaac catggtatgg gtggagatgt atgtgggatg   300
atgatggtta tatggtaatg gcgcataaag gtggtggcaa aggcaaggaa atatcgatga   360
cacgtaagca ga                                                       372
```